US011155578B2

(12) United States Patent
Michaeli et al.

(10) Patent No.: US 11,155,578 B2
(45) Date of Patent: Oct. 26, 2021

(54) PEPTIDE AGONISTS AND ANTAGONISTS OF TLR4 ACTIVATION

(71) Applicant: PEPTICOM LTD, Jerusalem (IL)

(72) Inventors: Amit Michaeli, Jerusalem (IL);
Immanuel Lerner, Jerusalem (IL);
Anke Burger-Kentischer, Stuttgart (DE); Steffen Rupp, Stuttgart (DE)

(73) Assignee: PEPTICOM LTD., Jerusalem (IL)

( * ) Notice: Subject to any disclaimer, the term of this patent is extended or adjusted under 35 U.S.C. 154(b) by 168 days.

(21) Appl. No.: 15/998,974

(22) PCT Filed: Feb. 16, 2017

(86) PCT No.: PCT/IL2017/050203
§ 371 (c)(1),
(2) Date: Aug. 17, 2018

(87) PCT Pub. No.: WO2017/141248
PCT Pub. Date: Aug. 24, 2017

(65) Prior Publication Data
US 2020/0247849 A1 Aug. 6, 2020

Related U.S. Application Data

(60) Provisional application No. 62/296,187, filed on Feb. 17, 2016.

(51) Int. Cl.
| *C07K 7/06* | (2006.01) |
| *C07K 7/08* | (2006.01) |
| *C07K 7/64* | (2006.01) |
| *C07K 14/71* | (2006.01) |
| *A61K 39/39* | (2006.01) |
| *A61K 38/04* | (2006.01) |
| *A61K 38/08* | (2019.01) |
| *A61K 38/10* | (2006.01) |
| *A61K 38/12* | (2006.01) |

(52) U.S. Cl.
CPC ............... *C07K 7/06* (2013.01); *A61K 39/39* (2013.01); *C07K 7/08* (2013.01); *C07K 7/64* (2013.01); *C07K 14/71* (2013.01); *A61K 38/04* (2013.01); *A61K 38/08* (2013.01); *A61K 38/10* (2013.01); *A61K 38/12* (2013.01)

(58) Field of Classification Search
CPC ...... A61K 38/04; A61K 38/12; C07K 14/705; C07K 14/70596; C07K 7/06; C07K 7/08
See application file for complete search history.

(56) References Cited

U.S. PATENT DOCUMENTS

| 7,629,444 B1 * | 12/2009 | Goldman | C07K 14/24 536/23.1 |
| 9,029,636 B2 * | 5/2015 | Wu | A01H 5/10 800/285 |
| 2004/0031072 A1 * | 2/2004 | La Rosa | C07H 21/04 800/278 |
| 2009/0327170 A1 | 12/2009 | Donati et al. | |
| 2013/0332133 A1 | 12/2013 | Horn et al. | |
| 2013/0333068 A1 | 12/2013 | Coffin | |
| 2014/0220074 A1 | 8/2014 | Shai et al. | |
| 2014/0356389 A1 | 12/2014 | Masignani et al. | |

FOREIGN PATENT DOCUMENTS

| CN | 101245098 A | 8/2008 |
| CN | 101805392 A | 8/2010 |
| WO | WO-200181581 A2 * | 11/2001 |
| WO | 2007053455 A2 | 5/2007 |
| WO | 2013120073 A1 | 8/2013 |

OTHER PUBLICATIONS

Huntley et al. Genbank Accession No. AGC48490, Jan. 16, 2015.*
Jinkerson et al. GenBank Accession No. JAC67988.1, Jun. 12, 2014.*
Shrivastava et al. Genbank Accession No. EEP55647.1, Aug. 20, 2020.*
Cornell et al., (1995) A Second Generation Force Field for the Simulation of Proteins, Nucleic Acids, and Organic Molecules. J Am Chem Soc 117(19): 5179-5197.
Gao et al., (2014) Rationally Designed Macrocyclic Peptides as Synergistic Agonists of LPS-Induced Inflammatory Response. Tetrahedron; Accepted manuscript; 5 pages. Published in final edited form as: Tetrahedron 70(42): 7664-7668.
Nishitani et al., (2006) Toll-like receptor 4 region Glu24-Lys47 is a site for MD-2 binding: importance of CYS29 and CYS40. J Biol Chem 281(50): 38322-38329.
Shanmugam et al., (2012) Synthetic Toll like receptor-4 (TLR-4) agonist peptides as a novel class of adjuvants. PLoS One 7(2): e30839; 10 pages.
Slivka et al., (2009) A peptide antagonist of the TLR4-MD2 interaction. Chembiochem 10(4): 645-649.
Kumar et al., Pathogen recognition by the innate immune system, International reviews of immunology, 2011, pp. 16-34.

(Continued)

*Primary Examiner* — Bridget E Bunner
(74) *Attorney, Agent, or Firm* — J.A. Lindeman & Co., PLLC

(57) ABSTRACT

A group of peptides is provided which activate or inhibit toll-like receptor 4 (TLR4) and may be used to modulate inflammatory signaling and host defense pathways. The peptides were derived in silico and tested in vitro in cell cultures. These peptides may be used in the preparation of immunomodulatory compositions such as vaccine adjuvants and in pharmaceutical compositions for immunomodulation of the innate immune system such as vaccine adjuvants. The peptides may also be used in the preparation of TLR4 activators, TLR4 inhibitors and MD2 labels, e.g., for research purposes.

10 Claims, 74 Drawing Sheets
Specification includes a Sequence Listing.

(56) References Cited

OTHER PUBLICATIONS

Tang et al., PAMPs and DAMPs: signals that spur autophagy and immunity, Immunological reviews, Sep. 2012, pp. 158-175.
Peri et al., Toll-like receptor 4 (TLR4) modulation by synthetic and natural compounds: an update, J Med Chem., May 8, 2014, pp. 3612-3622.
Simmons et al., Monocyte antigen CD14 is a phospholipid anchored membrane protein, Blood, Jan. 1989, pp. 284-289, vol. 73 No. 1.
Shimazu et al., MD-2, a molecule that confers lipopolysaccharide responsiveness on Toll-like receptor 4, J Exp Med, Jun. 7, 1999, pp. 1777-1782, vol. 189(11).
Cornell et al., A Second Generation Force Field for the Simulation of Proteins, Nucleic Acids, and Organic Molecules, Journal of the American Chemical Society, Nov. 10, 1994, pp. 5179-5197, vol. 117 No. 19.
Froese et al., Structural basis of glycogen branching enzyme deficiency and pharmacologic rescue by rational peptide design, Human Molecular Genetics, Apr. 2, 2015, pp. 5667-5676, vol. 24, No. 20.
Burger-Kentischer et al., A new cell-based innate immune receptor assay for the examination of receptor activity, ligand specificity, signaling pathways and the detection of pyrogens, J Immunol Methods, Oct. 12, 2009, pp. 93-103, 358(1-2).
Lerner et al., Heparanase powers a chronic inflammatory circuit that promotes colitis-associated tumorigenesis in mice, J Clin Invest, 2011, pp. 1709-1721, 121(5).
Michaeli et al., (2018) Computationally Designed Bispecific MD2/CD14 Binding Peptides Show TLR4 Agonist Activity. J Immunol 201(11):3383-3391.

\* cited by examiner

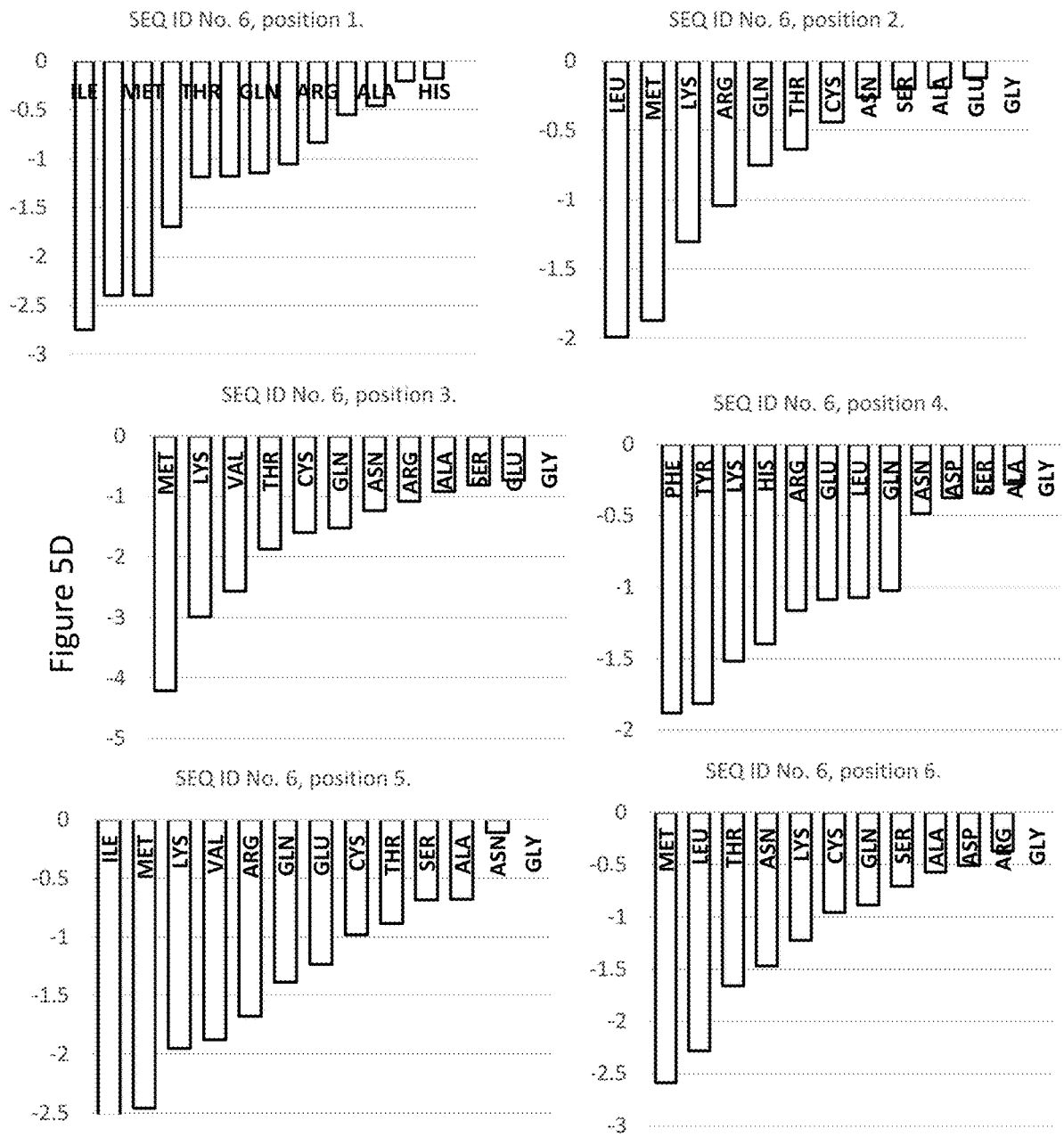

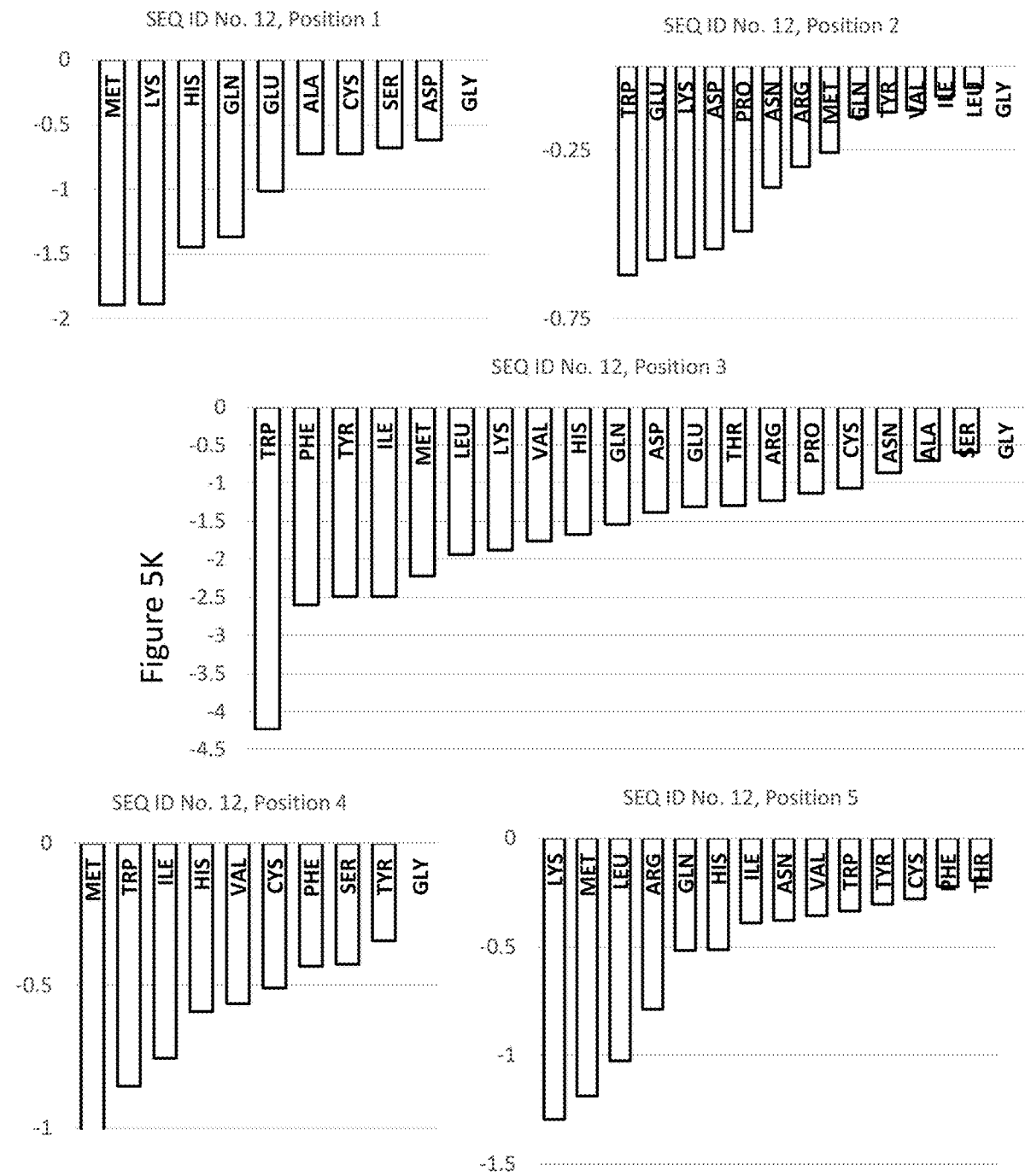

SEQ ID No. 1 (M1)

EC50 = 27.12 μM

EC50 = 10.19 μM

SEQ ID No. 1 (M3)

EC50 = 22.32 µM

EC50 = 6.56 µM

SEQ ID No. 1 (M1)

SEQ ID No. 1 (M2)

EC50 = 3,19 µM

EC50 = 2,29 µM

SEQ ID No. 1 (M3)

SEQ ID No. 2

SEQ ID No. 4

SEQ ID No. 5

SEQ ID No. 6

SEQ ID No. 7

SEQ ID No. 8

SEQ ID No. 9

SEQ ID No. 10

SEQ ID No. 11

SEQ ID No. 14

SEQ ID No. 16

SEQ ID No. 17

EC50 = 44,30 µM    IC50 > 100 µM

SEQ ID No. 18

EC50 = 29,19 µM

SEQ ID No. 19

SEQ ID No. 21

SEQ ID No. 22

SEQ ID No. 9

PEPTIDE AGONISTS AND ANTAGONISTS OF TLR4 ACTIVATION

TECHNICAL FIELD

The present invention relates to the field of immunomodulation, and more particularly, to peptides that modify the activation of toll-like receptor 4 (TLR4).

BACKGROUND OF THE INVENTION

Toll-like receptors (TLRs) play a critical role in the early innate immunity and the subsequent activation of the adaptive immune response by recognizing highly conserved structural motifs (Kumar et al. 2011, Pathogen recognition by the innate immune system. *International reviews of immunology* 30, 16-34), the pathogen-associated molecular patterns (PAMPs) or Danger Associated Molecular Patterns (DAMPs) (Tang et al. 2012, PAMPs and DAMPs: signals that spur autophagy and immunity. *Immunological reviews* 249, 158-75). As the main sensors of the innate immune system and key sensors of microbial infection in mammals, TLRs modulate the induction of hundreds of host genes through a complex network of signaling that allows for an appropriate response to a given microbial pathogen. TLR4 is one of the best characterized and clinically important members of the TLR family, the central ligand for TLR4 is lipopolysaccharide (LPS) derived from Gram-negative bacteria cell wall, with other natural and synthetic activators discovered as well (Peri and Calabrese 2014, Toll-like receptor 4 (TLR4) modulation by synthetic and natural compounds: an update. *J Med Chem.*, 3612-3622).

TLR4 activation by LPS is mediated by either cluster of differentiation-14 (CD14) (Simmons et al. 1989, Monocyte antigen CD14 is a phospholipid anchored membrane protein. *Blood* 73, 284-9) and/or myeloid differentiation factor 2 (MD2) (Shimazu et al. 1999, MD-2, a molecule that confers lipopolysaccharide responsiveness on Toll-like receptor 4. *J Exp Med.* 189(11):, 1777-1782) co-receptors, this activation initiates a signaling cascade that involves a number of proteins finally leading to the activation of the transcription factor NF-κB which induces the secretion of proinflammatory cytokines and effector cytokines that direct the adaptive immune response. This type of activation is also utilized by some vaccine adjuvants such as E6020 developed by Eisai and Monophosphoryl Lipid A (MPL).

WIPO Publication No. 2013120073, which is incorporated herein by reference in its entirety, discloses immunological adjuvants which specifically bind to an anti-lipopolysaccharide (LPS) antibody or antigen binding fragment thereof, and activates NF-κ in a cell, wherein activation of NF-κB identifies the peptide as an immunological adjuvant.

U.S. Patent Application Publication No. 20140220074, which is incorporated herein by reference in its entirety, discloses peptides including an amino acid sequence of a fragment of mammalian TLR-4, namely $TIIX_1VX_2VLX_3VLVVX_4V$ ($X_1$ is selected from the group consisting of Gly, Ser, Gln and Ala; $X_2$, $X_3$ and $X_4$ are each independently selected from the group consisting of Ser, Gln and Ala), derived using the ToxR-TM-MalE (ToxR transmembrane maltose binding protein) chimeric protein.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a peptide that binds TLR4 with at least one of co-receptors myeloid differentiation factor 2 (MD2) and cluster of differentiation 14 (CD14), the peptide comprising a sequence selected from the group consisting of SEQ ID No. 1-30.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 5A-5L illustrate substitution variation ranges for all amino acid positions in SEQ ID Nos. 4-6, 8, 9 and 12 peptides, according to some embodiments of the invention.

Figure 10:
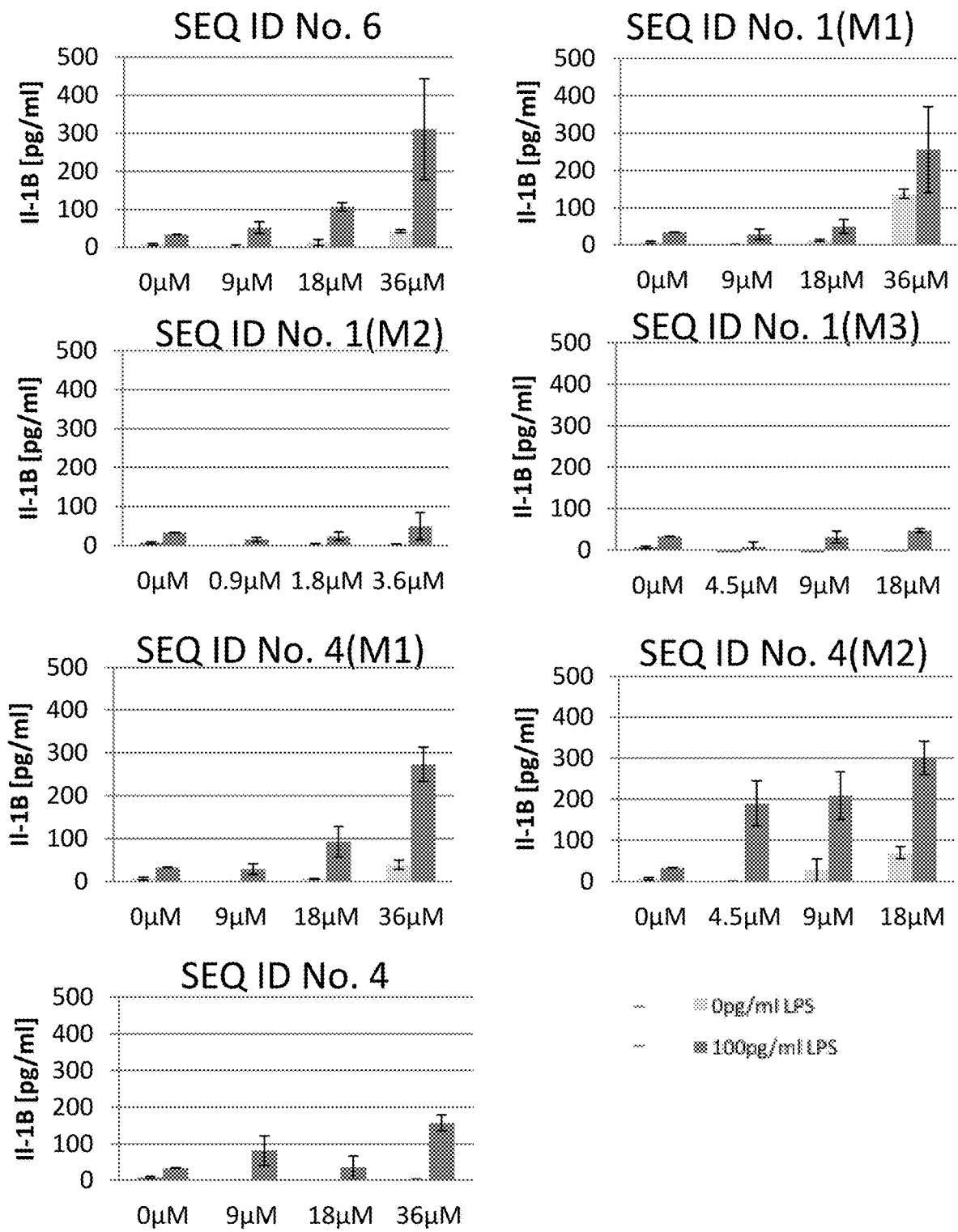

FIG. 10 presents the release of Interleukin-1β from Human whole blood samples in response to peptide of SEQ ID No. (1M1,1M2,1M3), 4 and (M1,M2), 6 alone or in combination with LPS.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Peptides which activate or inhibit toll-like receptor 4 (TLR4) and methods of using the peptides in the modification of inflammatory signaling and host defense pathways are provided. The peptides were derived in silico and tested in vitro in cell cultures and whole blood.

The peptides were computationally designed to bind TLR4 with at least one of the co-receptors myeloid differentiation factor 2 (MD2) and cluster of differentiation 14 (CD14), and comprise a sequence selected from the group consisting of SEQ ID Nos. 1-21, presented in Table 1. All the peptides listed in Table 1 were predicted to bind TLR4, either as is, as a partial peptide, or as part of a larger polypeptide. TLR4 activator peptides lead to an independent activation of TLR4 downstream signaling and TLR4 inhibitors peptides lead to suppression of TLR4 downstream signaling in the presence of LPS, the peptides may also act synergistically with other TLR4 modulating molecules. These peptides are shown for the first time to activate/inhibit TLR4 via CD14 and/or MD2 co-receptors (as indicated in Table 1), with the activation being independent of other activator molecules and occurring in a dose dependent manner. SEQ ID Nos. 23-30 represent exemplary peptide generalizations of SEQ ID Nos. 4, 5 and 9 (SEQ ID No. 23); 6 (SEQ ID Nos. 24 and 25); 8 (SEQ ID Nos. 26 and 27); and 12 (SEQ ID No. 28) respectively, and are considered to be referred to when the respective parent peptides are discussed in the following.

TABLE 1

FASTA sequences (N-terminus → C-terminus, c[..] indicating cyclic peptides) of TLR4-MD2 activating peptides (peptide SEQ ID Nos. 1-8, 16-19, 21-22), and inhibitory peptides (SEQ ID Nos. 9-15, 20), as well as exemplary peptide generalizations (SEQ ID Nos. 23-30).

| SEQ ID No. | FASTA Sequence | Activity | Co-Receptor/s |
|---|---|---|---|
| 1 | RYETMSIMIKSGGKG | Activator | MD2/CD14 |
| 1 (M1) | RYETMSIMIKSGGKY | Activator | MD2/CD14 |
| 1 (M2) | RYETMSIMIKSGGKY- (methyl group replacing C-terminus) | Activator | MD2/CD14 |
| 1 (M3) | RYETMSIMIKSGGKG- (methyl group replacing C-terminus) | Activator | MD2/CD14 |
| 2 | EWGWRMII | Activator | MD2/CD14 |
| 2 (M1) | (N') 1(S)Glu-2(S)Trp-3Gly-4(S)Trp-5(S)Arg-6(S)Met-7(R, S)Ile-8Bzl(Gly) (C') | Activator | MD2/CD14 |
| 3 | PLWMMIKSMGSMMEMKK | Activator | MD2 |
| 4 [23] | ILYMSLKWM | Activator | MD2/CD14 |
| 4 (M1) | 1(N') Ava-OH-2Leu-3Tyr-4Met-5Ser-6Leu-7Lys-8Trp-9Met (C') | Activator | MD2/CD14 |
| 4 (M2) | (N') Chg-2Leu-3Tyr-4Met-5Ser-6Leu-7Lys-8Trp-9Met (C') | Activator | MD2/CD14 |
| 5 [23] | ILYKSLKWM | Activator | MD2/CD14 |
| 6 [24,25] | c[MLSFRM] | Activator | MD2/CD14 |
| 7 | c[WMLGMESI] | Activator | CD14 |
| 8 [26,27] | c[IGFMMMKKEF] | Activator | MD2/CD14 |
| 9 [23] | ILFMGMKWL | Inhibitor | MD2 |
| 10 | MIPYGMRMM | Inhibitor | MD2 |
| 11 | LAWYFGRKIKE | Inhibitor | MD2 |
| 12 [28] | KKLMLII (at the C-terminus $CH_3$ replace COOH) | Inhibitor | MD2/CD14 |
| 13 | c[SWEFLW] | Inhibitor | MD2/CD14 |
| 14 | c[SIWDTMW] | Inhibitor | MD2 |
| 15 | c[IWSRSW] | Inhibitor | MD2 |
| 16 | rmmmw (all D-amino acids, $CH_3$ group replaces C-term) | Activator | MD2/CD14 |

TABLE 1-continued

FASTA sequences (N-terminus → C-terminus, c[..] indicating cyclic peptides) of TLR4-MD2 activating peptides (peptide SEQ ID Nos. 1-8, 16-19, 21-22), and inhibitory peptides (SEQ ID Nos. 9-15, 20), as well as exemplary peptide generalizations (SEQ ID Nos. 23-30).

| SEQ ID No. | FASTA Sequence | Activity | Co-Receptor/s |
|---|---|---|---|
| 17 | wwikd (all D-amino acids, both isoleucine chiral centers in D-enantiomer) | Activator | MD2/CD14 |
| 18 | tiymmmtmkg (all D-amino acids, both isoleucine chiral centers in D-enantiomer) | Activator | CD14 |
| 19[(29)] | c[gwlwrsl] (all D-amino acids) | Activator | MD2/CD14 |
| 20[(29)] | c[gwwwral] (all D-amino acids) | Inhibitor | MD2/CD14 |
| 21 | c[geldkftm] (all D-amino acids) | Activator | MD2/CD14 |
| 22 | c[gfwseeeksl] (all D-amino acids) | Activator | MD2/CD14 |
| 23* | $X_1X_2X_3X_4X_5X_6X_7X_8X_9$ | Activator or Inhibitor | MD2/CD14 |
| 24* | $c[X_1X_2X_3X_4X_5X_6]$ | Activator | MD2 |
| 25* | $c[X_1X_2X_3X_4X_5X_6]$ | Activator | CD14 |
| 26* | $c[X_1X_2X_3X_4X_5X_6X_7X_8X_9X_{10}]$ | Activator | MD2 |
| 27* | $c[X_1X_2X_3X_4X_5X_6X_7X_8X_9X_{10}]$ | Activator | CD14 |
| 28* | $X_1X_2X_3X_4X_5X_6X_7$ | Inhibitor | MD2/CD14 |
| 29* | $c[X_1X_2X_3X_4X_5X_6X_7]$ | Activator or Inhibitor | MD2/CD14 |
| 30* | $c[X_1X_2X_3X_4X_5X_6X_7X_8X_9X_{10}]$ | Activator | MD2/CD14 |

*SEQ ID Nos. 23-30 represent exemplary peptide generalizations of SEQ ID Nos. 4, 5 and 9 (SEQ ID No. 23); 6 (SEQ ID Nos. 24 and 25); 8 (SEQ ID No. 26 and 27); 12 (SEQ ID No. 28); 19, 20 (SEQ ID No. 29); and 22 (SEQ ID No. 30) respectively. The identities of amino acids $X_i$, with i being the representative amino acid number in the sequence, individual substitution options are defined below.

These peptides may be used in the preparation of immunomodulatory compositions such as vaccine adjuvants and in pharmaceutical compositions for immunomodulation of the innate immune system. The peptides may also be used in the preparation of TLR4 activators, TLR4 inhibitors and MD2 labels, e.g., for research purposes. Specifically, one or more peptides including SEQ ID Nos. 1-30 may also be part of peptide assemblies capable of blocking the activation of TLR4 by an activator molecule (e.g., LPS) or independently activate TLR4.

For all peptides, except the peptides with cyclic backbones (SEQ ID Nos. 6, 7, 8, 13, 14, 15, 19, 20, 21 and 22), there are termini additions that are compatible with the CD14 and/or MD2 binding mode. SEQ ID Nos. 1, 2 and 12 can be compatible with binding MD2 when additional atoms (including but not limited to, amino acids) added to their N-terminus. SEQ ID Nos. 1, 3, 4, 5, 9 and 11 can be compatible with binding MD2 when additional atoms (including but not limited to, amino acids) added to their C-terminus. For binding CD14, SEQ ID Nos. 1, 2 and 12 allow N-terminus additions. C-terminal modifications are compatible with SEQ ID Nos. 4 and 5. Both SEQ ID No. 10 and SEQ ID No. 11 can only accommodate additional atoms at the C-terminus. The additions to the respective termini may be large as these termini face the external solution. Additions may be used to modify and enhance the biological deliverability, and may comprise e.g., peptides or proteins. Specifically, the additions to peptides SEQ ID Nos. 1-5 and 9-12 at the above-specified termini, as well as to peptides SEQ ID Nos. 16 and 21 presented below (at the N-termini) may comprise antigens selected to target specific antibodies. Some of these binding mode compatible modifications were demonstrated for SEQ ID No. 1, with RYETM-SIMIKSGGKY—hereby SEQ ID No. 1 (M1), RYETM-SIMIKSGGKY-(methyl group replacing C-terminus)—hereby SEQ ID No. 1 (M2), and RYETMSIMIKSGGKG-(methyl group replacing C-terminus)—hereby SEQ ID No. 1 (M3). Also demonstrated was a modification for SEQ ID No. 2, (N') 1 (S)Glu-2(S)Trp-3Gly-4(S)Trp-5(S)Arg-6(S)Met-7(R,S)Ile-8Bzl(Gly) (C'), hereby SEQ ID No. 2 (M1). Modifications were also demonstrated for SEQ ID No. 4, with 1(N) Ava-OH-2Leu-3Tyr-4Met-5Ser-6Leu-7Lys-8Trp-9Met (C')—hereby SEQ ID No. 4 (M1) and (N') Chg-2Leu-3Tyr-4Met-5Ser-6Leu-7Lys-8Trp-9Met (C') hereby SEQ ID No. 4 (M2). Any of these modifications and additions is considered to be part of the present invention as a molecular derivative of the respective peptide.

FIGS. 1A-1H present predicted binding energy contributions for each amino acid in the peptides of SEQ ID Nos. 1-15, calculated for binding via MD2, according to some embodiments of the invention. The lower the individual amino acid binding energy contribution is, the more cardinal it is for the peptide binding (the efficiency of which is determined by the sum of the binding energy contributions). The binding energy contributions were calculated using an ab initio algorithm that takes into account molecular mechanics force-fields in three dimensions (3D) and at a 1 Å resolution. The binding energy contributions were calculated using the Assisted Model Building with Energy Refinement (AMBER) (Cornell 1995, A Second Generation Force Field for the Simulation of Proteins, Nucleic Acids, and Organic Molecules. *Journal of the American Chemical Society* 117, 5179-5197) force-field with the Generalized-Born/Surface Area (GB/SA) solvation model, and was already effectively applied to other fields as well (Froese et al. 2015, Structural basis of glycogen branching enzyme deficiency and pharmacologic rescue by rational peptide design. *Hum Mol Genet.* 24(20), 5667-5676). The energies shown are to the most potent TLR4/co-receptor pair observed during the experimental validation. These data can be used to design modified peptides, e.g., incorporate SEQ ID Nos. 1-30 into larger peptides or modify the sequences while maintaining the overall negative binding energy, as well as to design peptide mimetics and/or small molecules.

The peptides provided in Table 1 demonstrate, in a non-limiting manner, the different sizes, components and types (linear and cyclic peptides) which effective peptides may take while forming a similar interaction pattern with the receptor residues. In the following it is shown how other peptides may be derived from the binding energy calculations and generalized effective peptides are defined. It was found that the primary calculated binding energy component in all but one modelled peptides comes from interactions with the CD14 and/or MD2 co-receptors, with one peptide, SEQ ID No. 3, also having a substantial binding energy component with TLR4 itself.

Figure 1A:
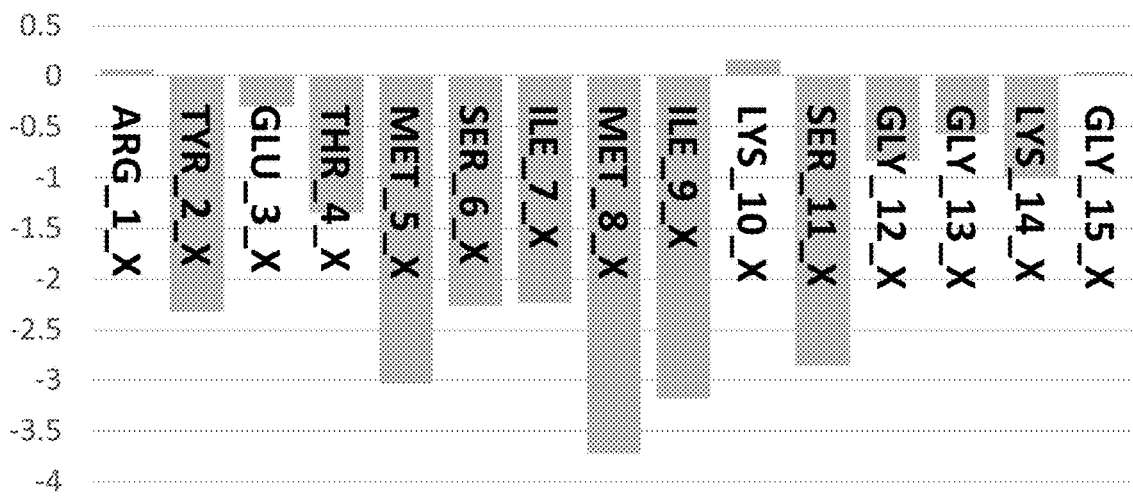
FIGS. 1A-1K present predicted TLR4-MD2 binding energy contributions for each amino acid in the peptides of SEQ ID Nos. 1-22, according to some embodiments of the invention.
Figure 1A:
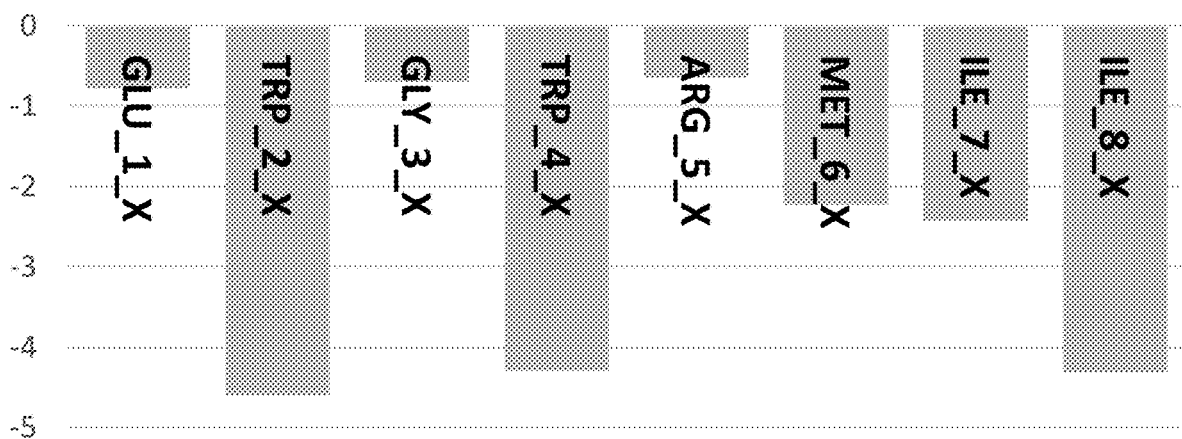
Figure 1B:
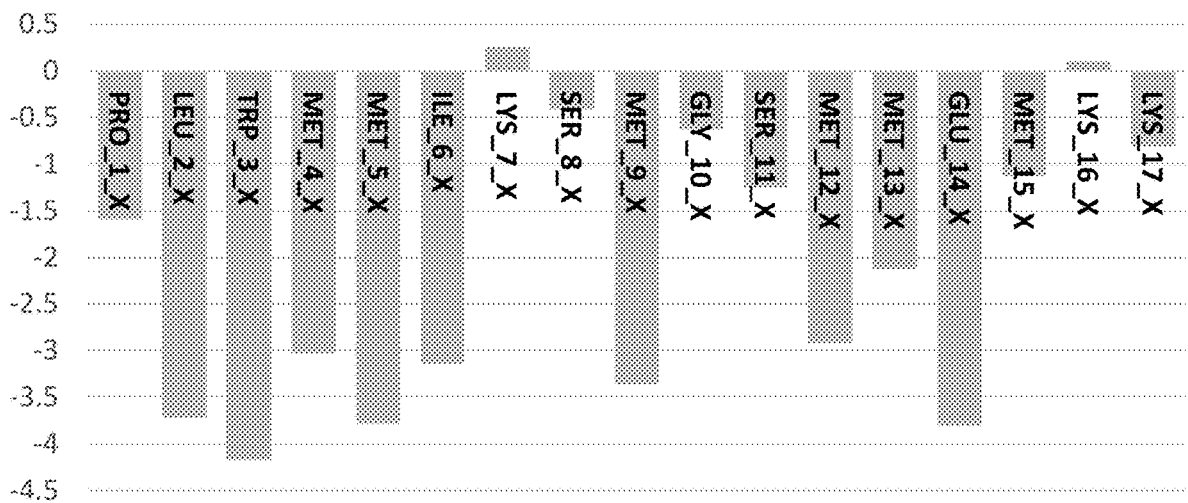
Figure 1B:
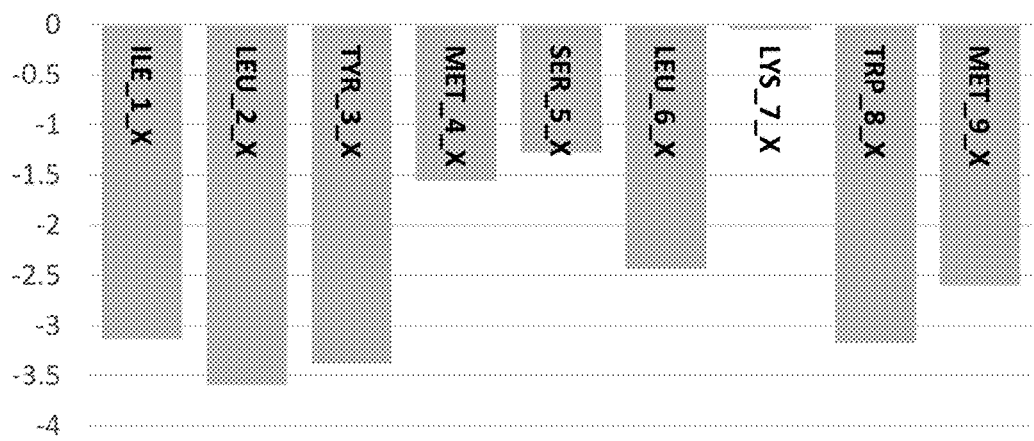
Figure 1C:
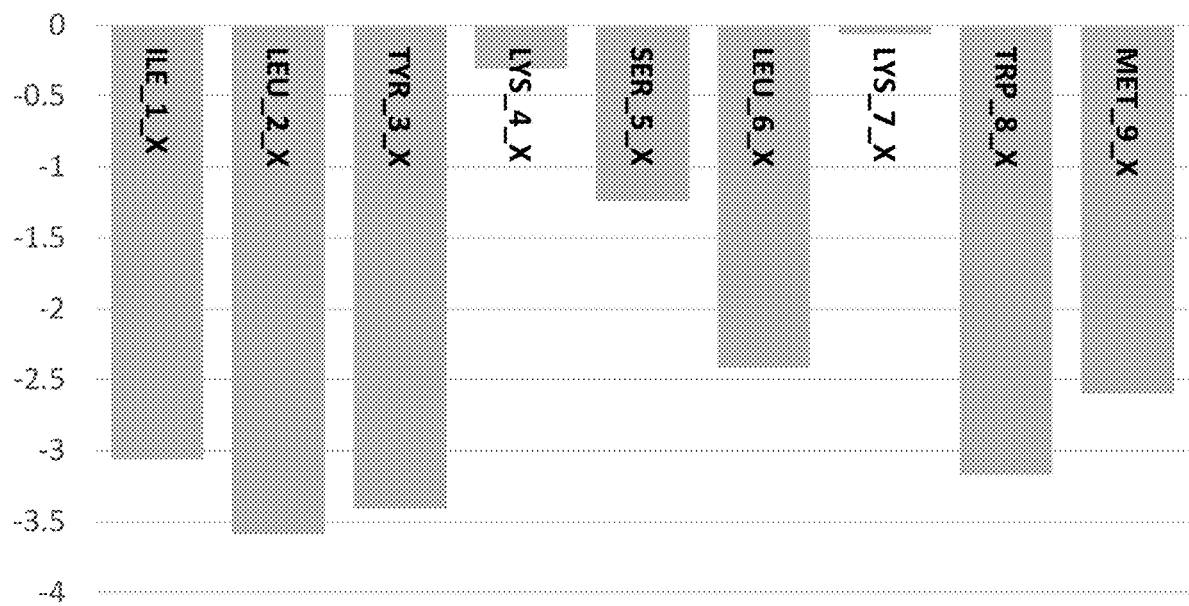
Figure 1C:
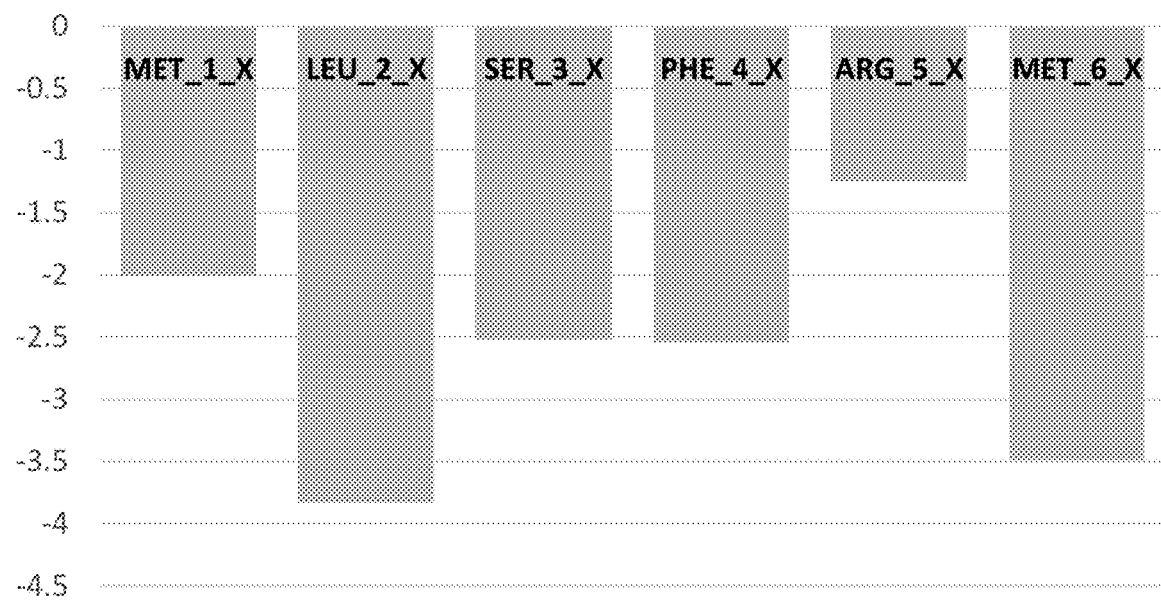
Figure 1D:
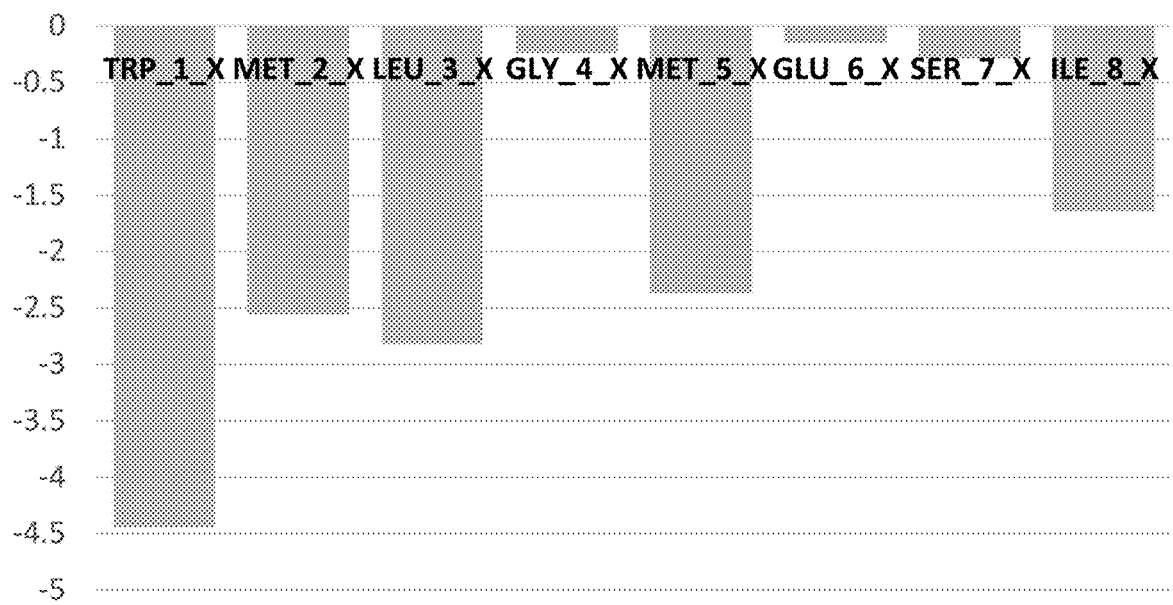
Figure 1D:
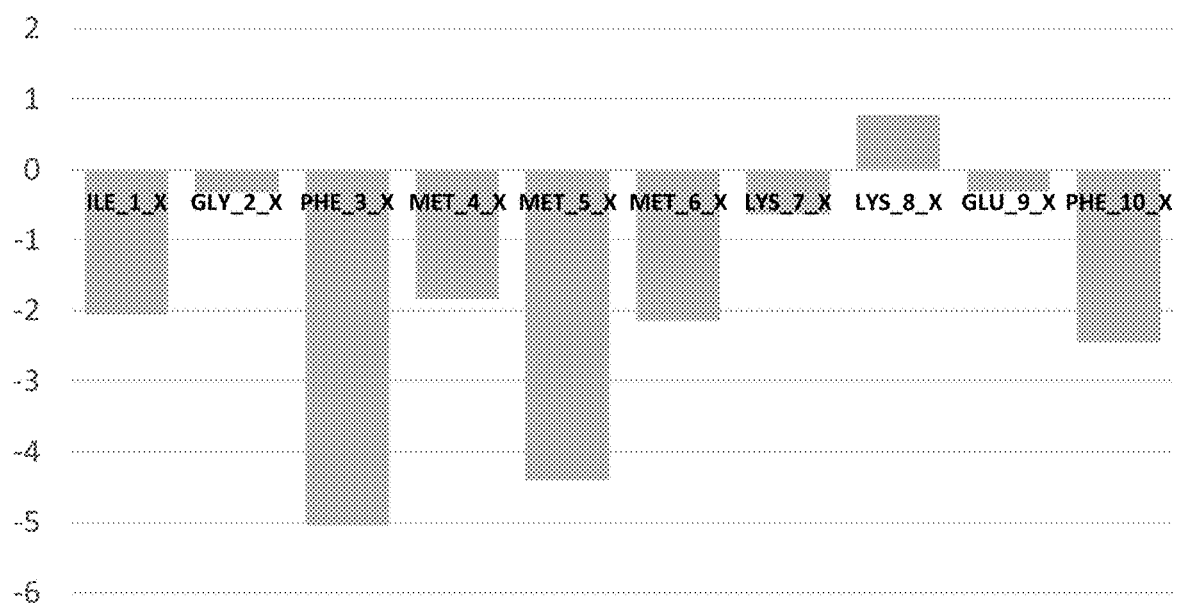
Figure 1E:
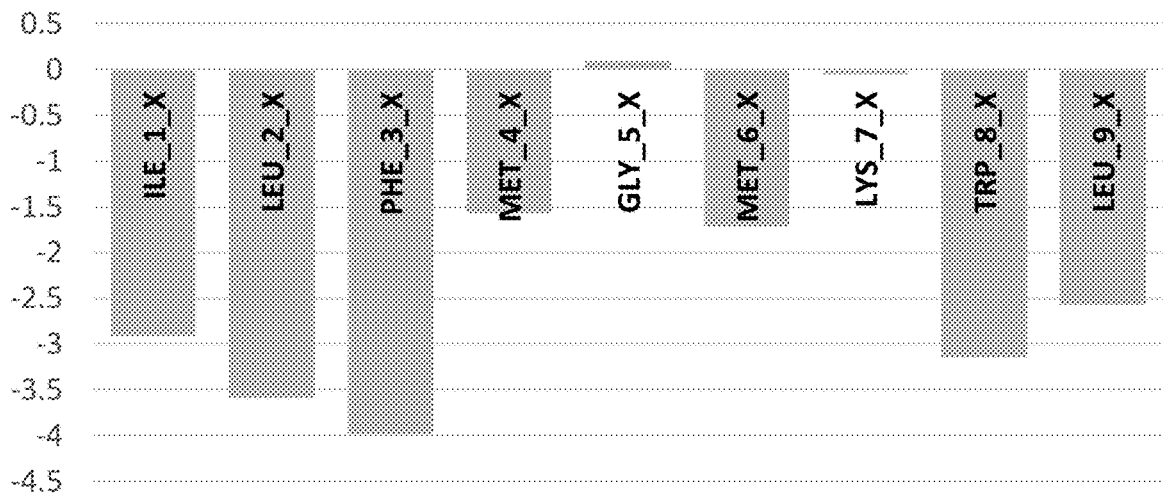
Figure 1E:
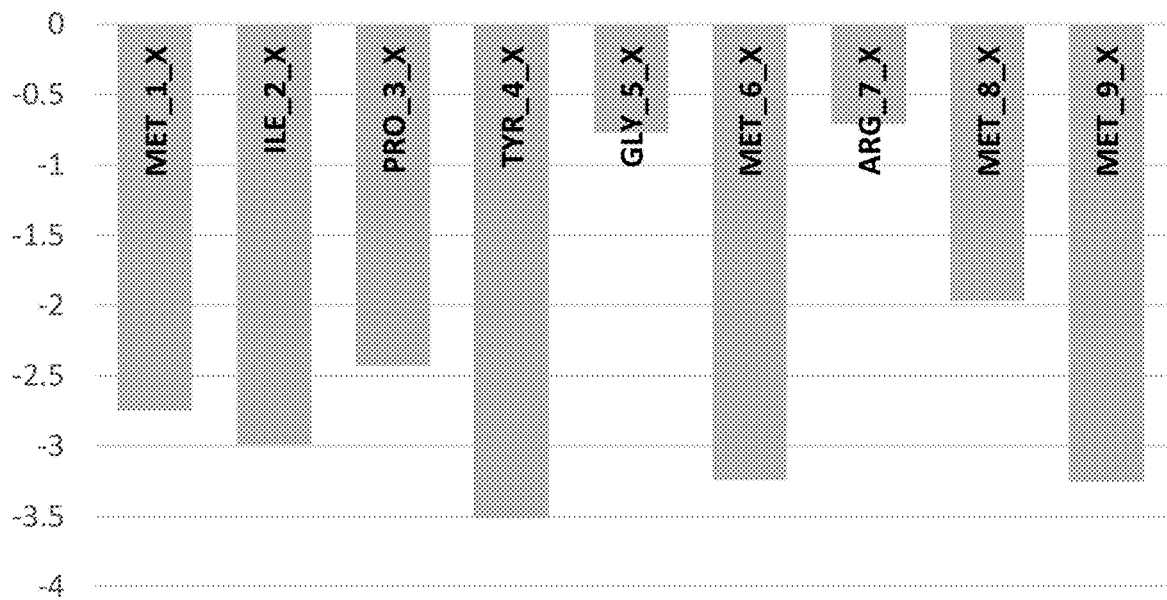
Figure 1F:
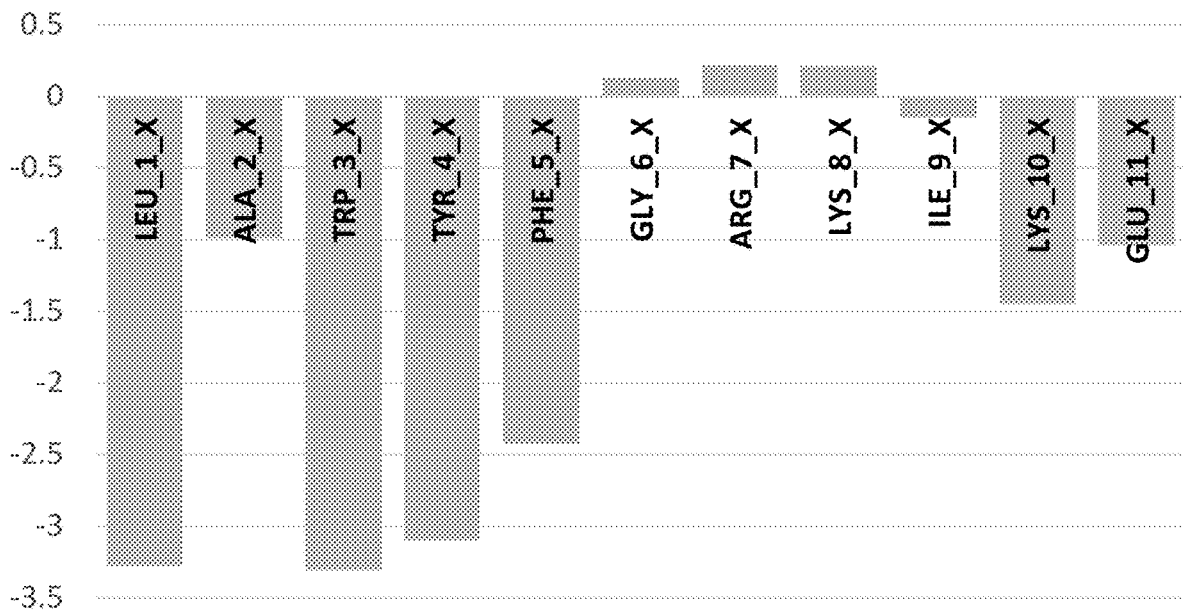
Figure 1F:
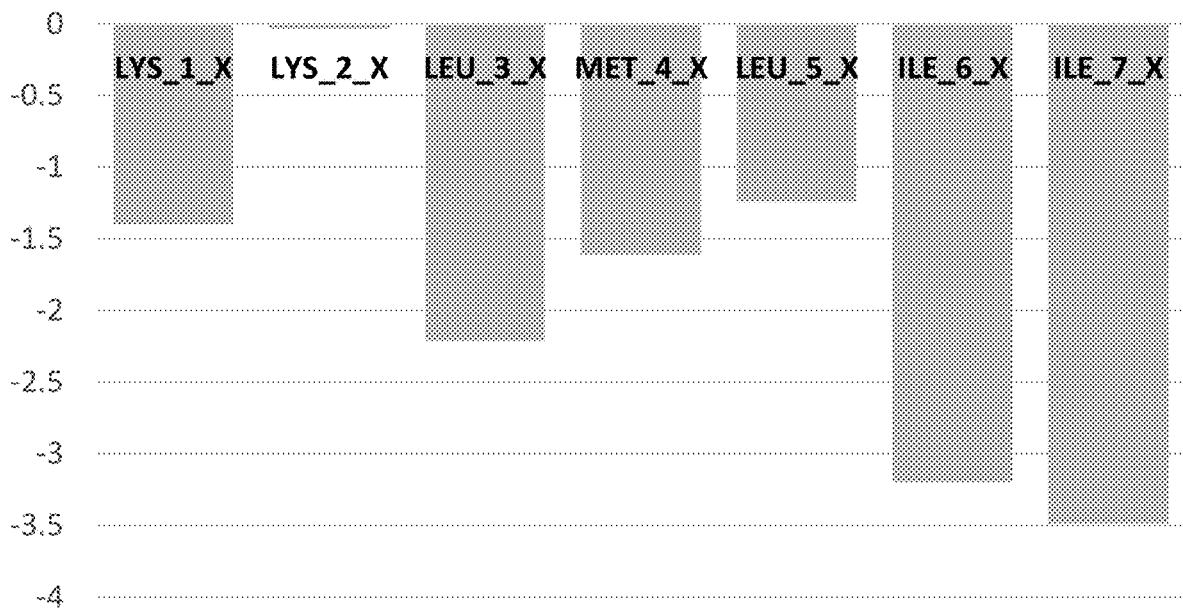
Figure 1G:
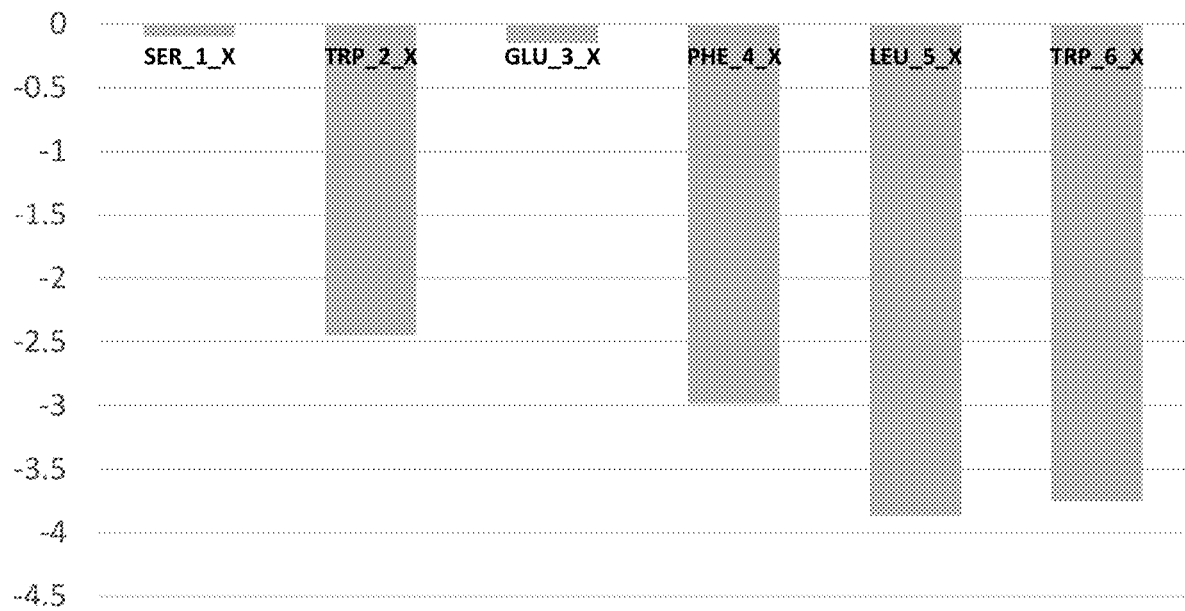
Figure 1G:
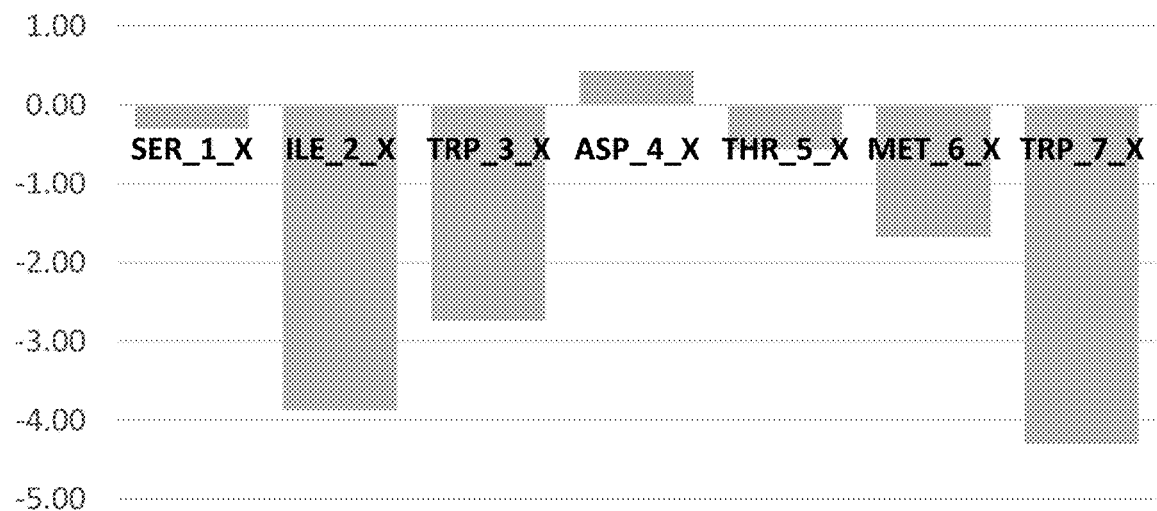
Figure 1H:
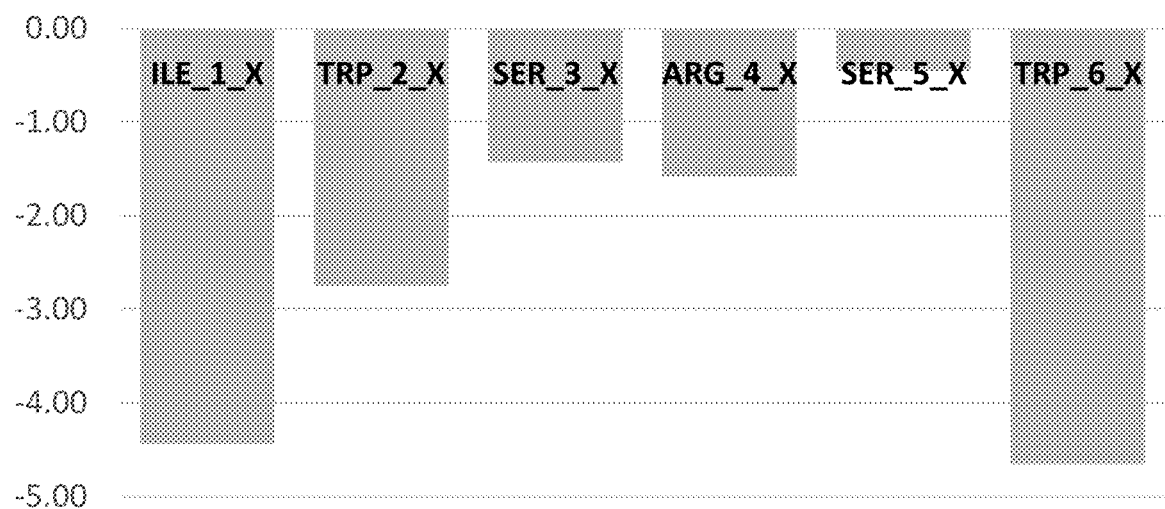
Figure 1H:
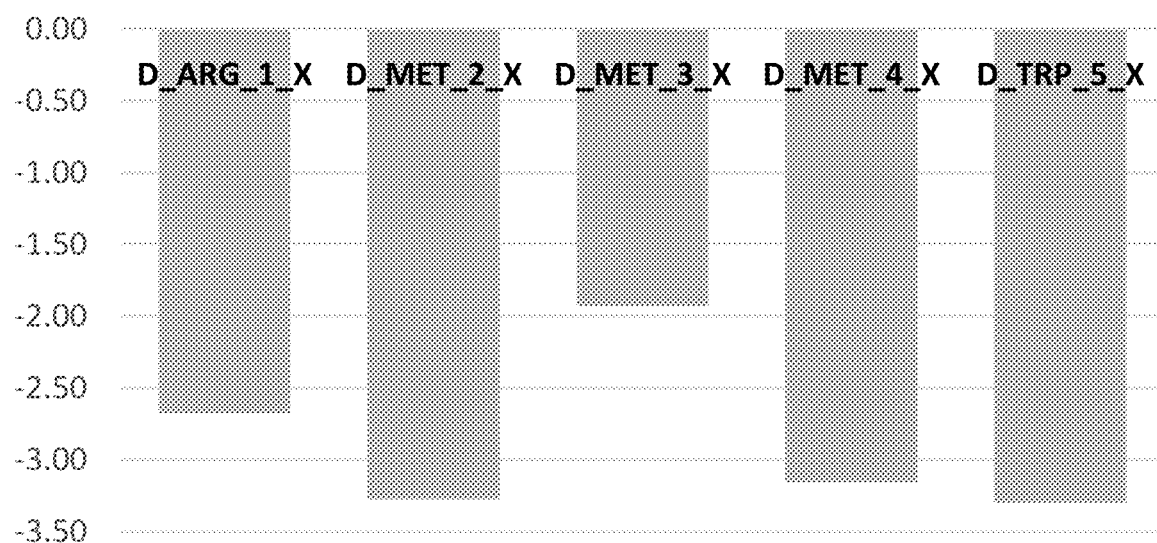
Figure 1I:
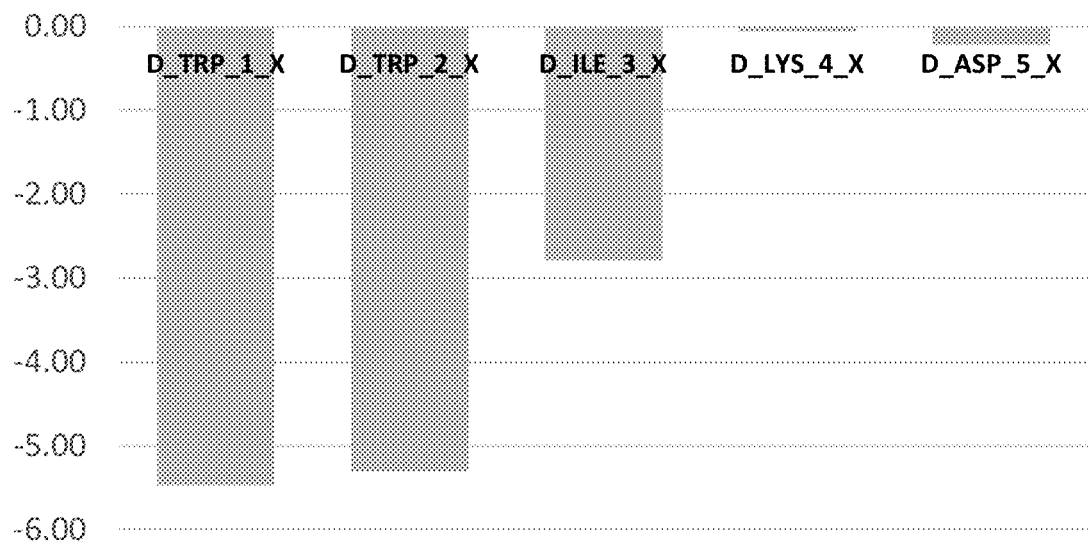
Figure 1I:
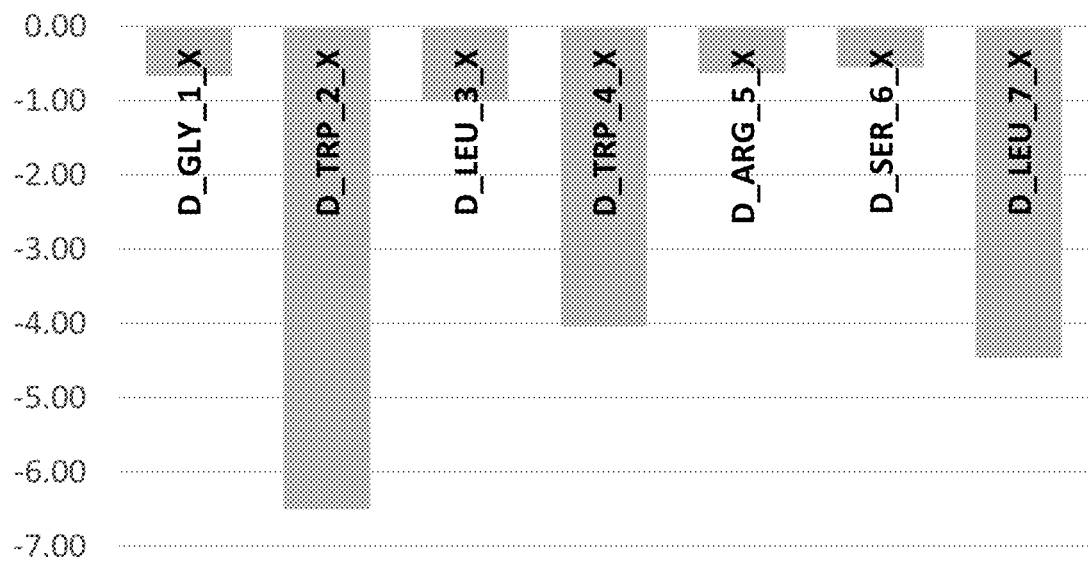
Figure 1J:
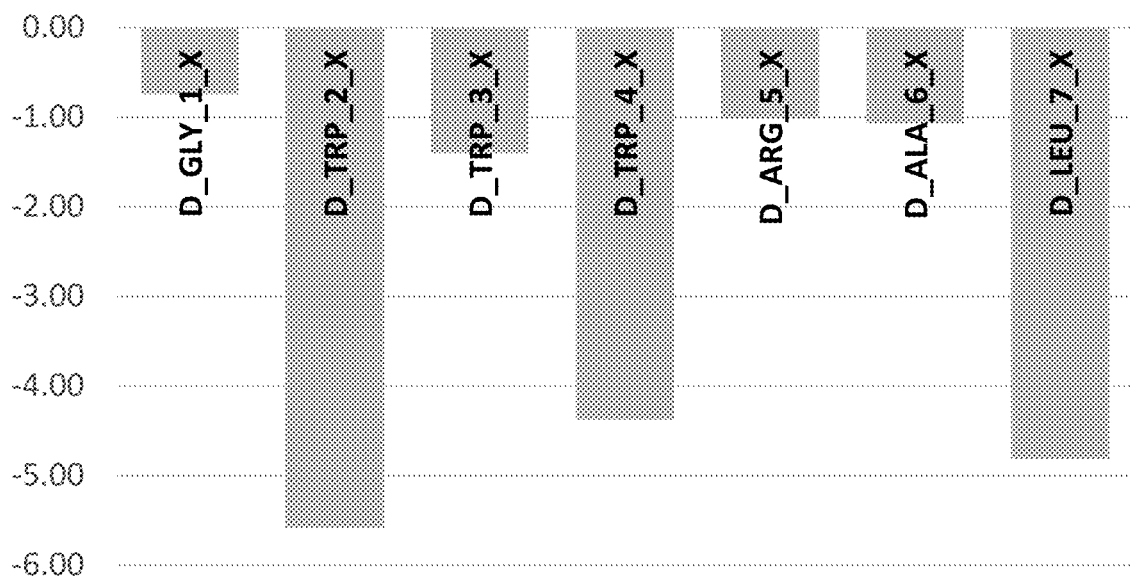
Figure 1J:
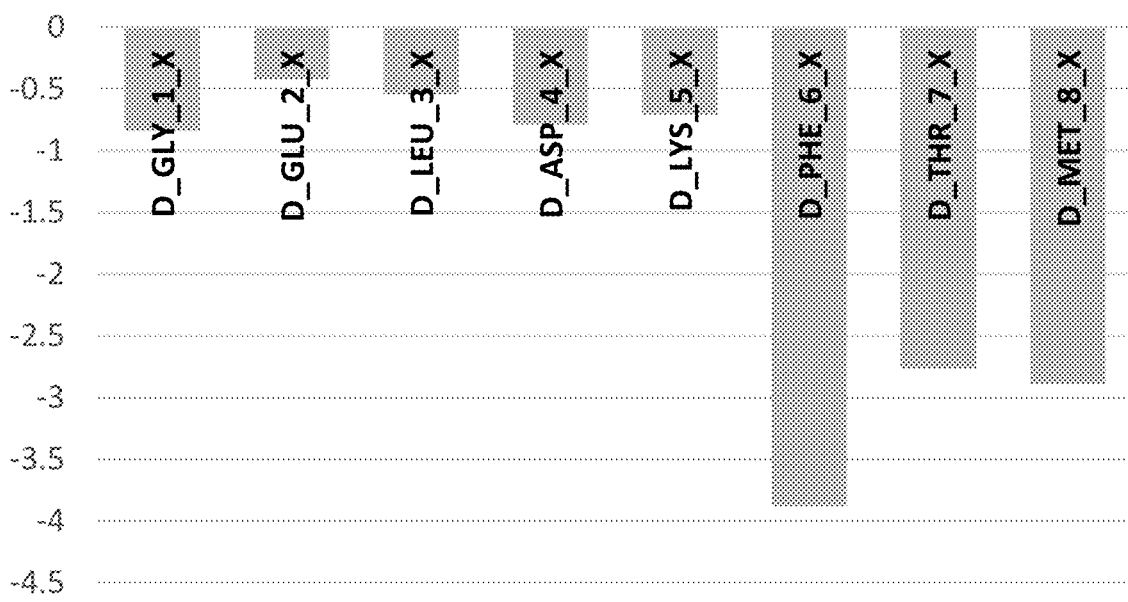
Figure 1K:
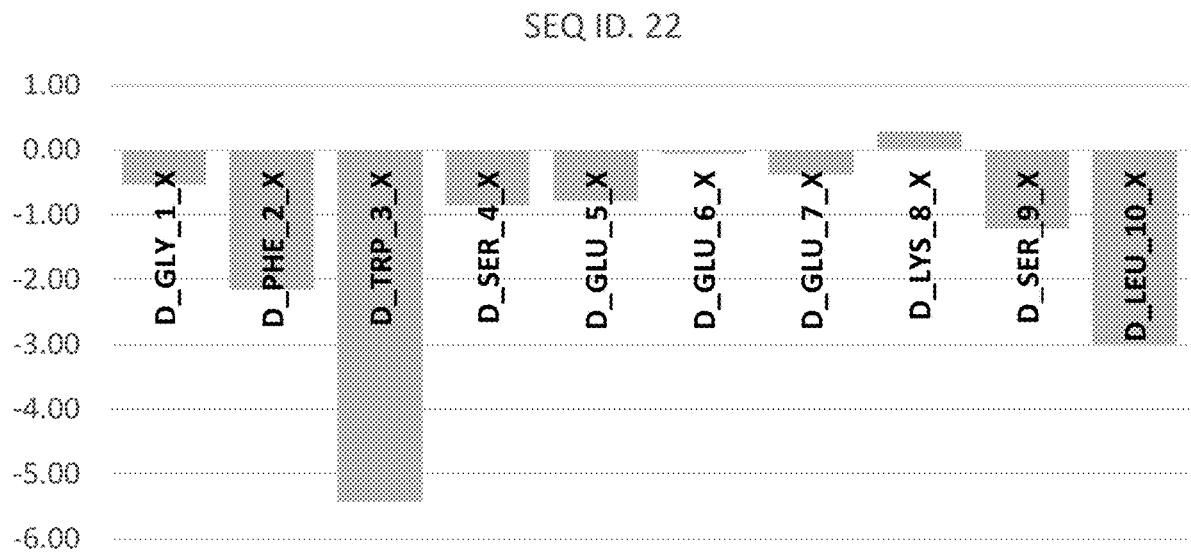
Figure 1L:
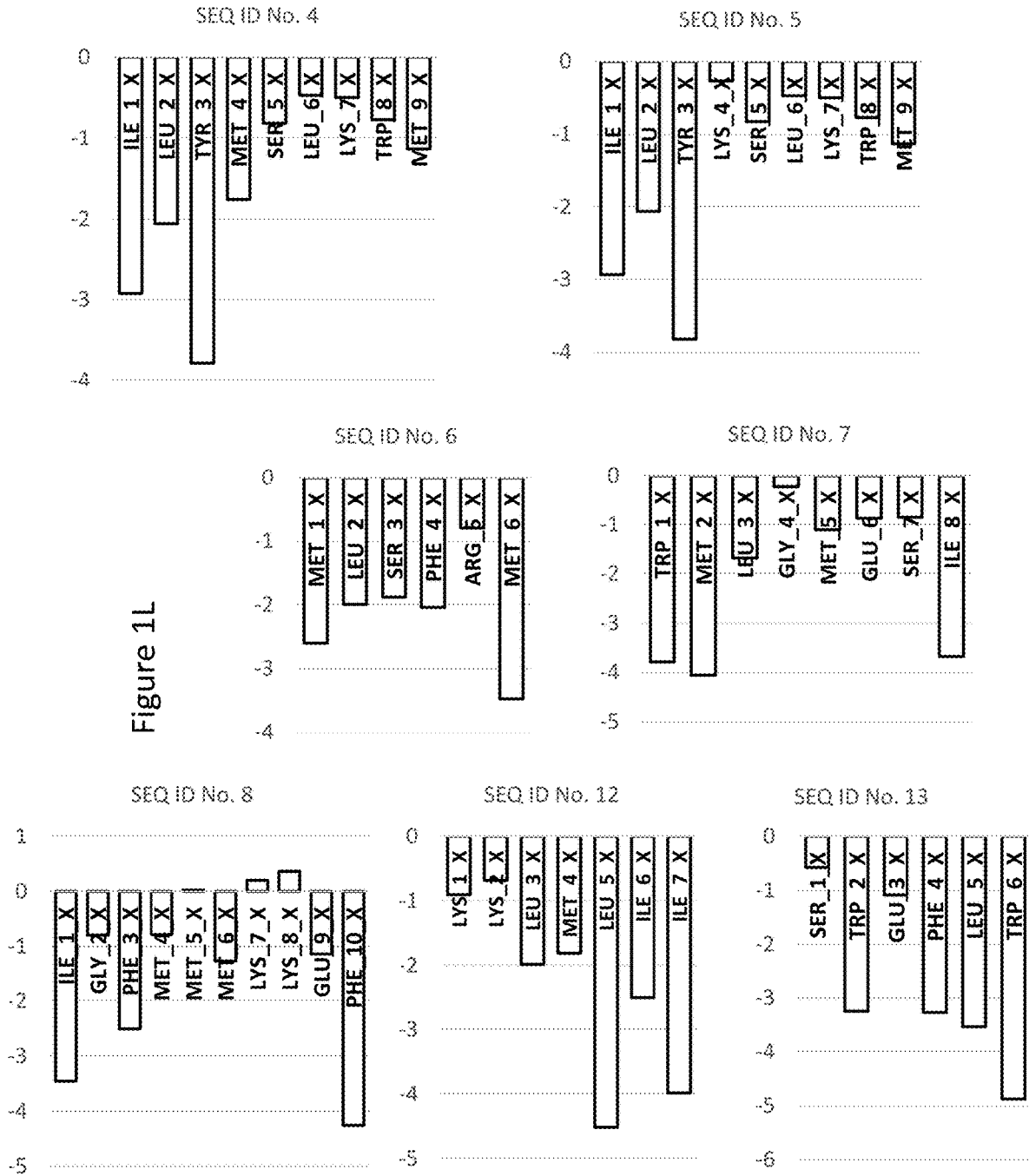
FIG. 1L presents the individual residue contributions of SEQ ID Nos. 4-8, 12 and 13 (which appear on both the CD14 and MD2 peptide design outputs) to the interaction with CD14, according to some embodiments of the invention.
Figure 2A:
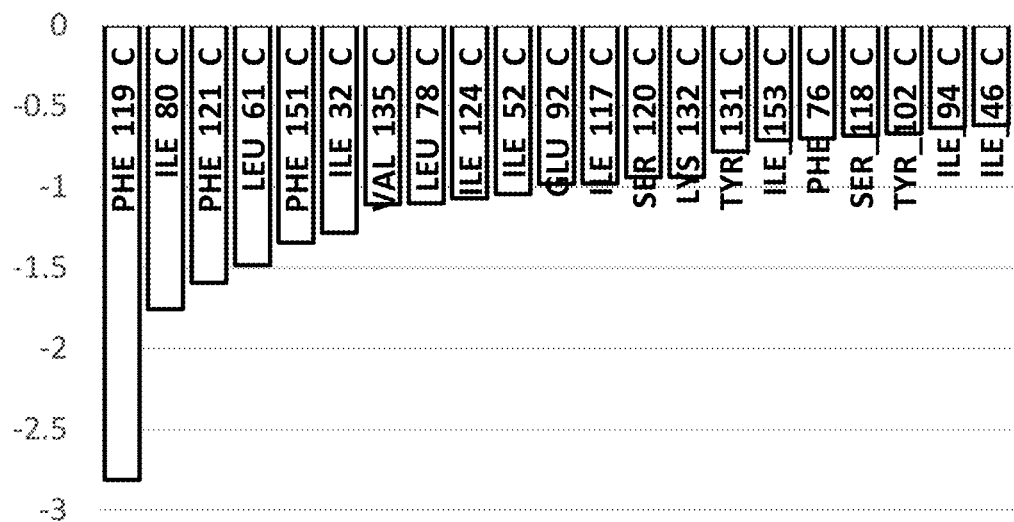
FIGS. 2A-2K present MD2 co-receptor calculated binding energies for each peptide of SEQ ID Nos. 1-22, according to some embodiments of the invention.
Figure 2A:
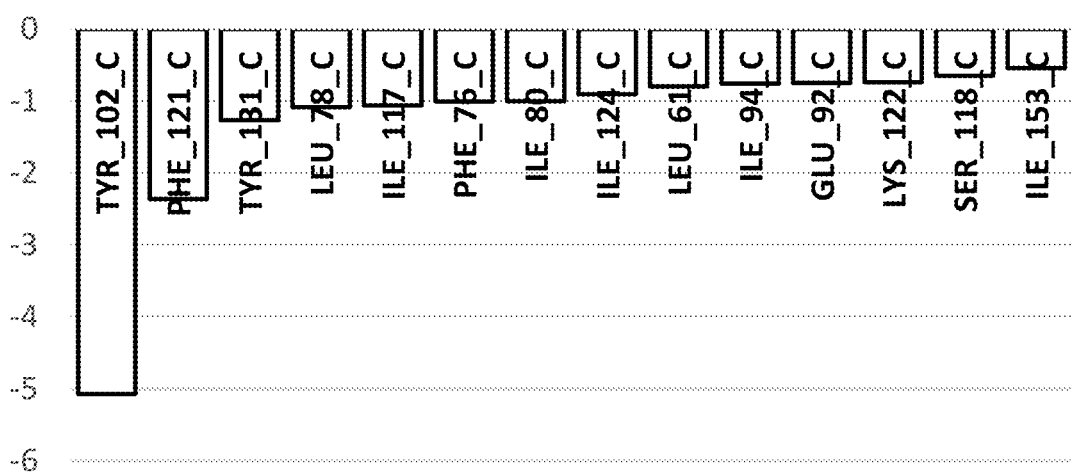
Figure 2B:
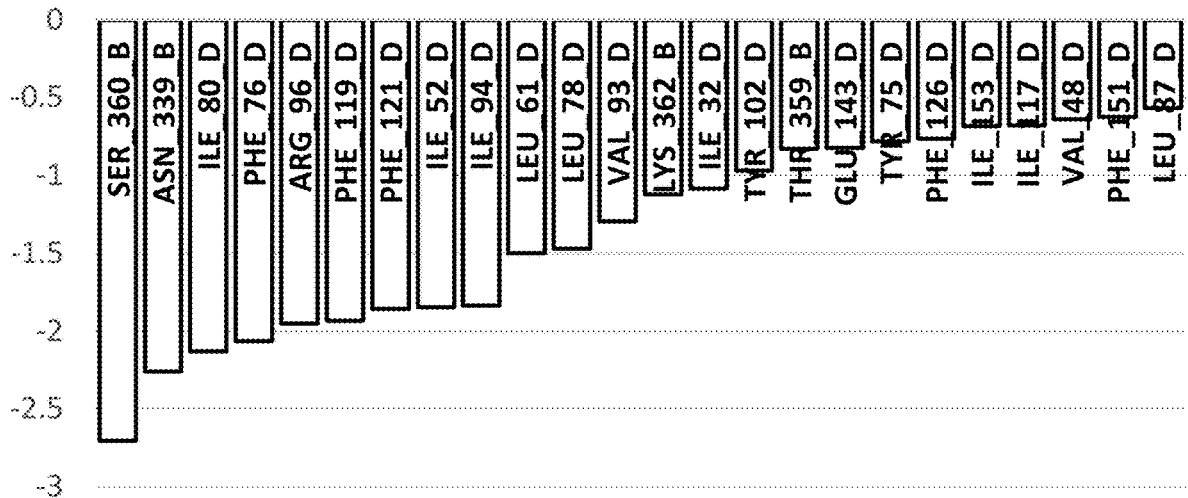
Figure 2B:
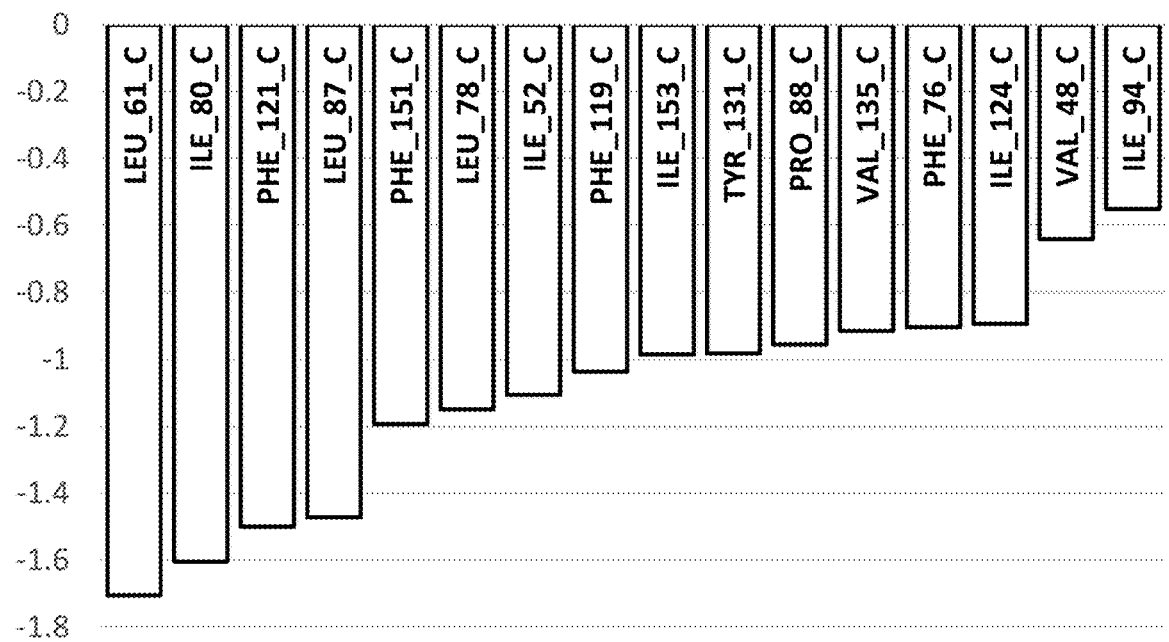
Figure 2C:
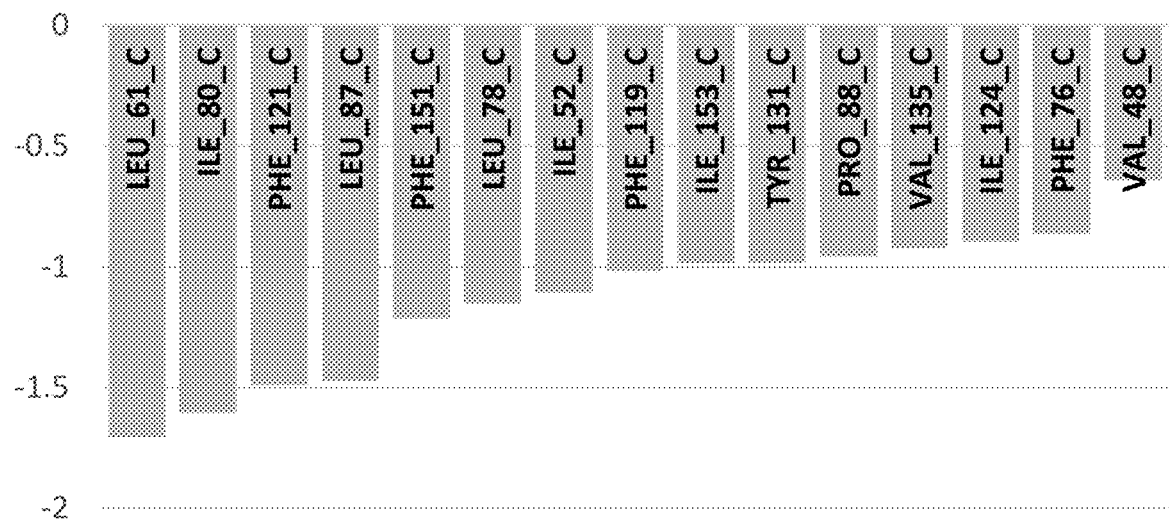
Figure 2C:
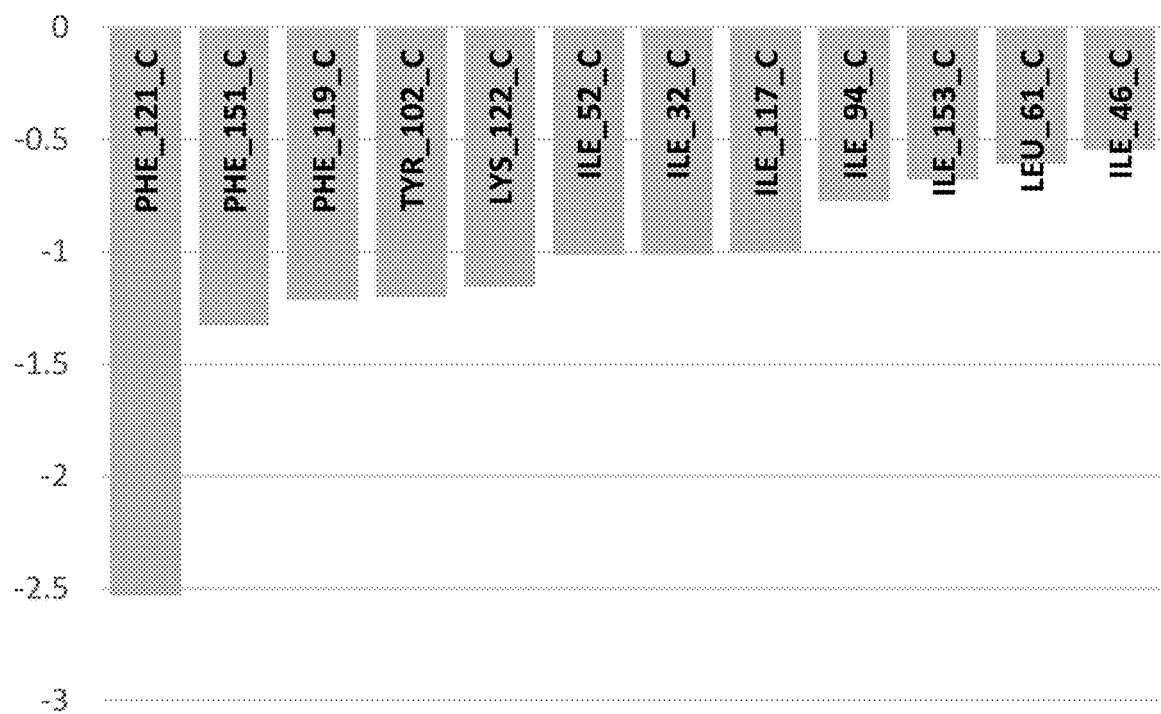
Figure 2D:
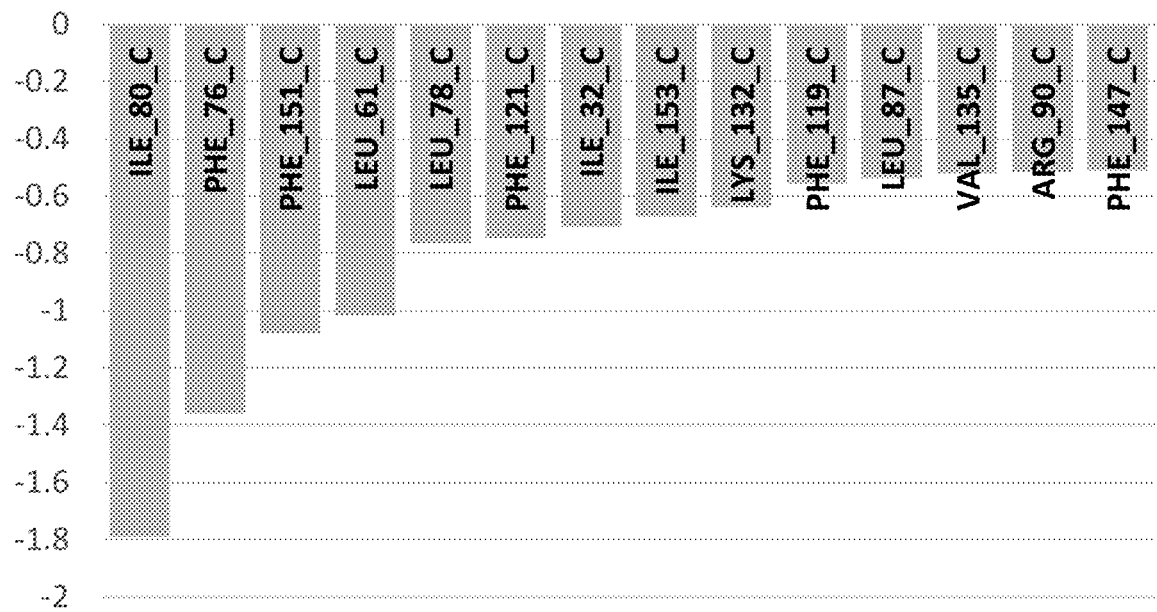
Figure 2D:
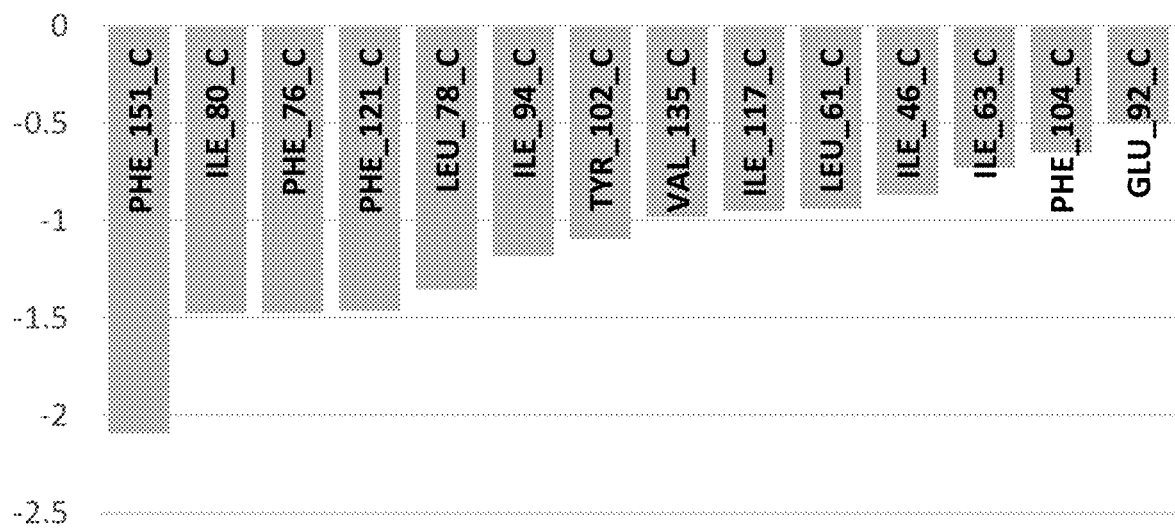
Figure 2E:
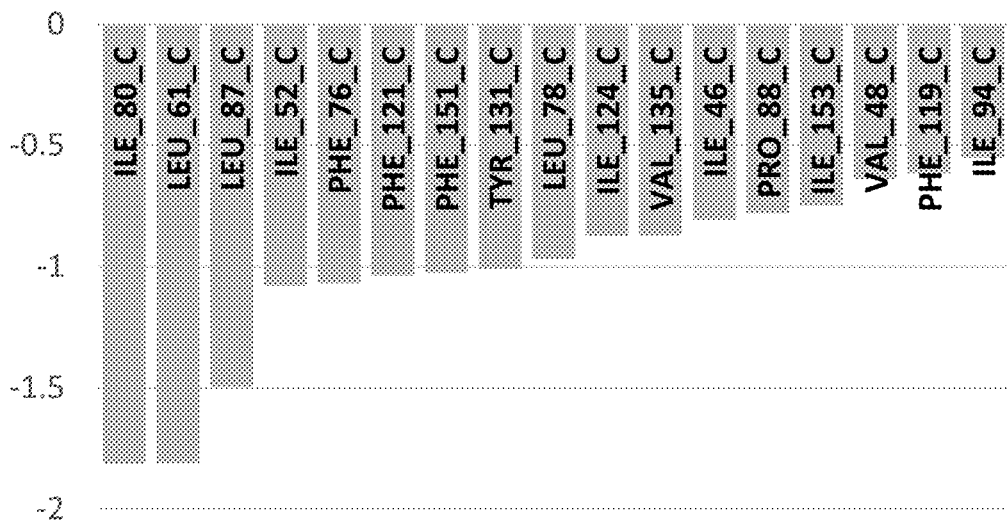
Figure 2E:
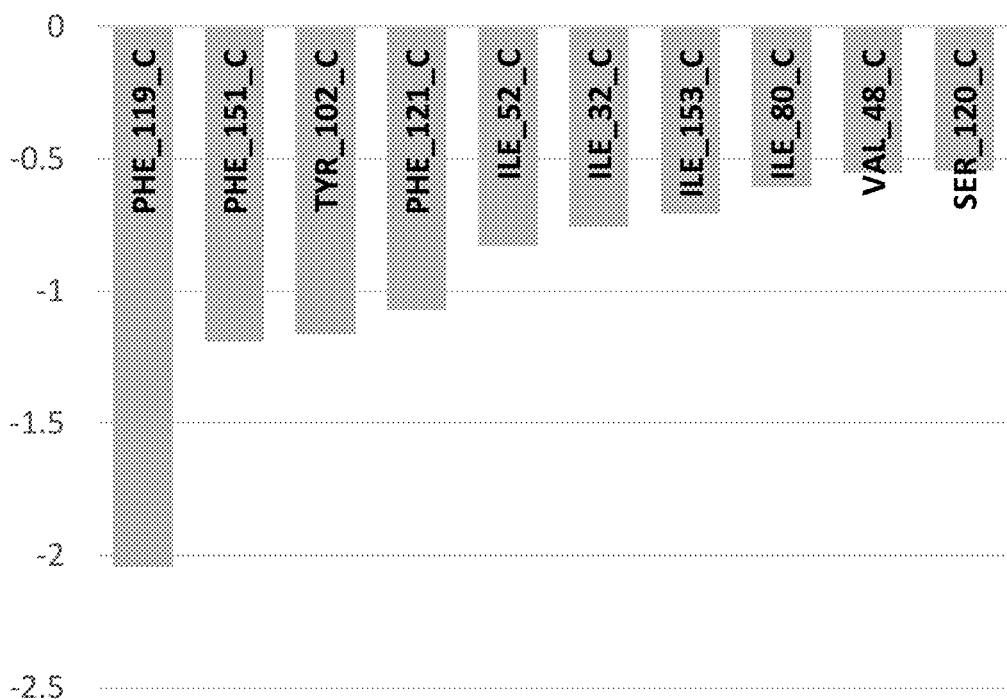
Figure 2F:
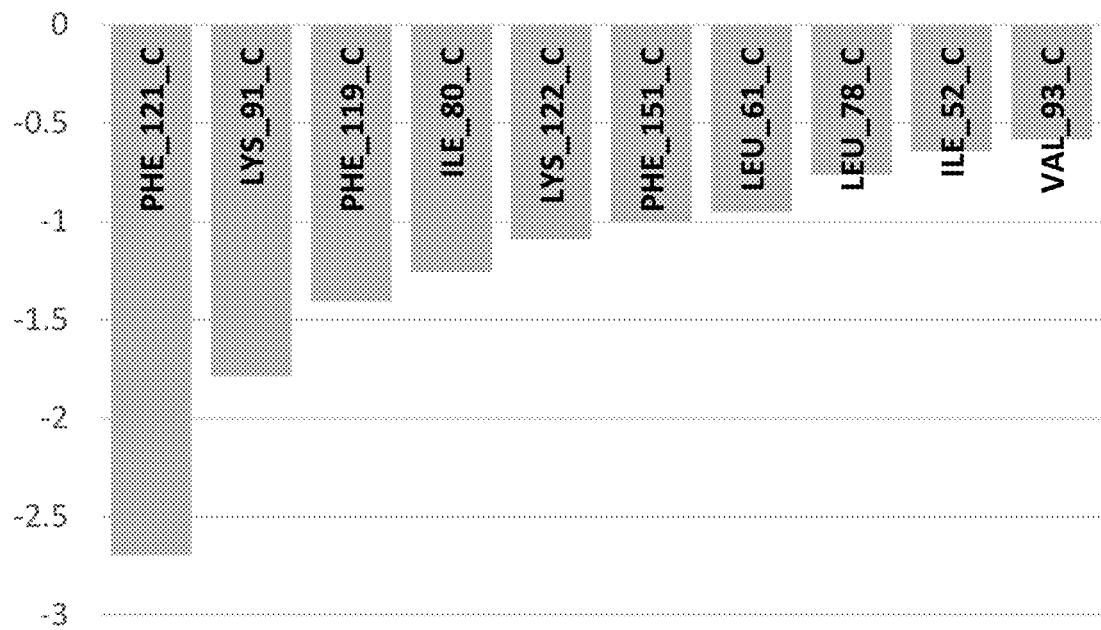
Figure 2F:
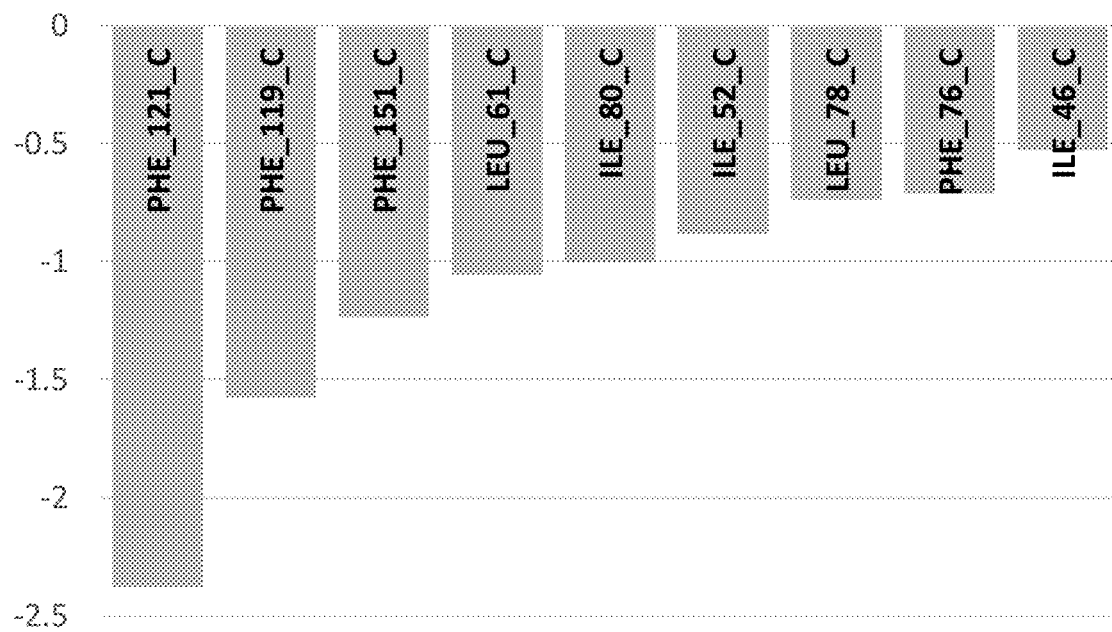
Figure 2G:
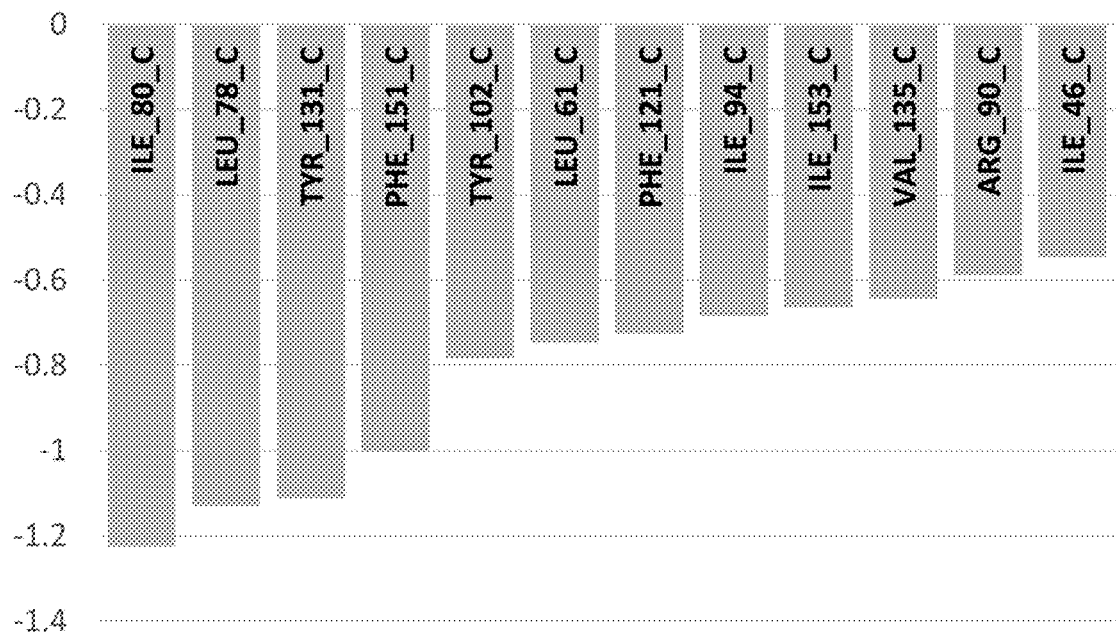
Figure 2G:
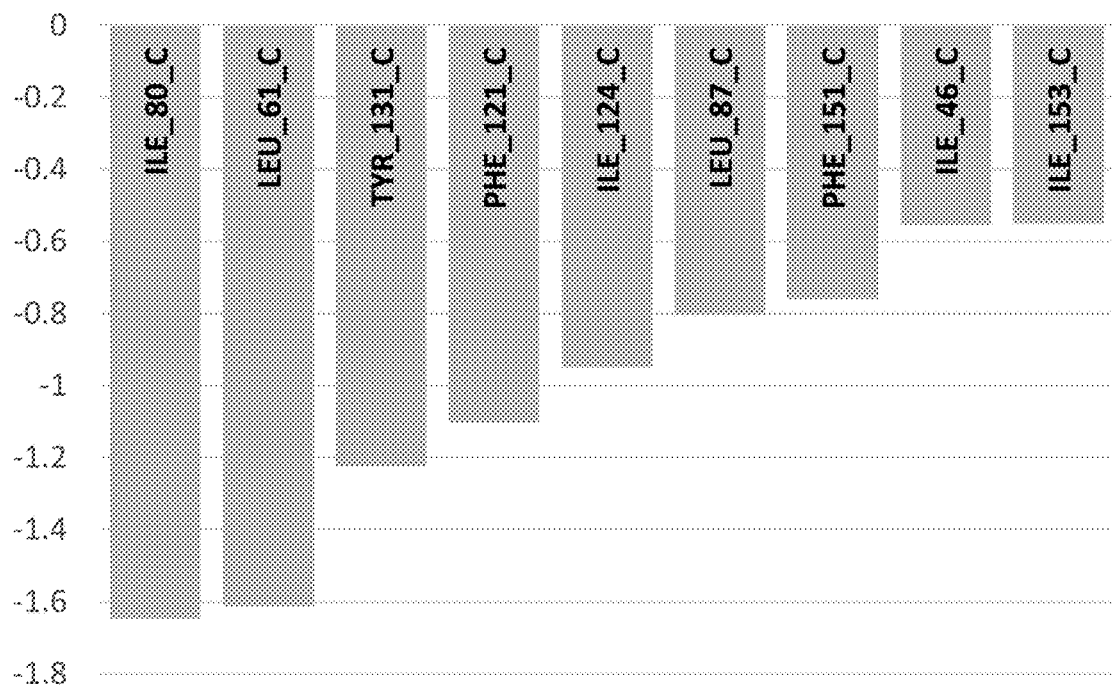
Figure 2H:
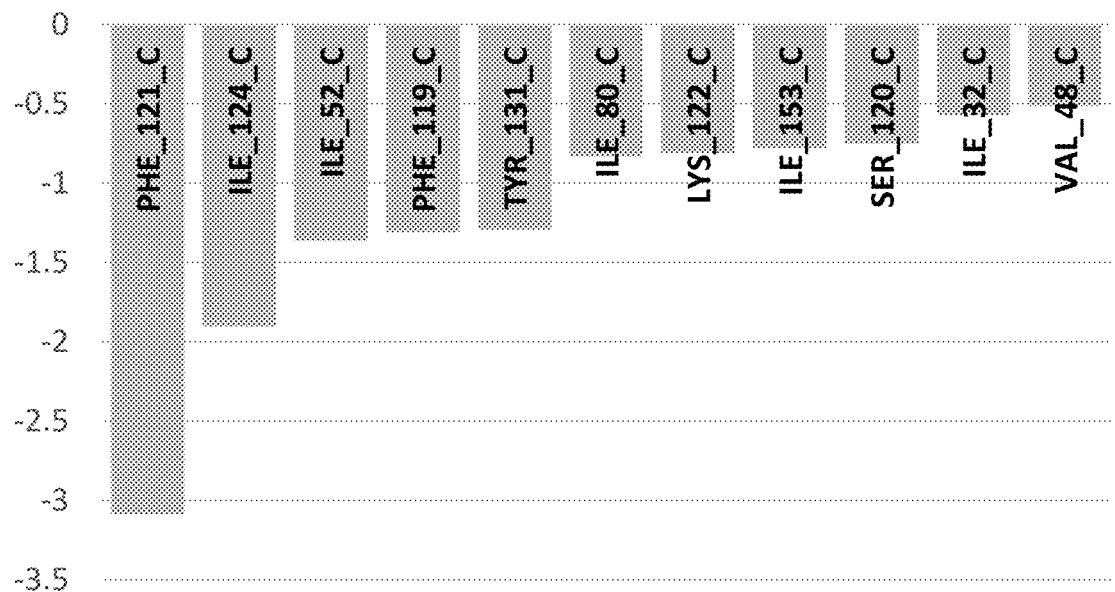
Figure 2H:
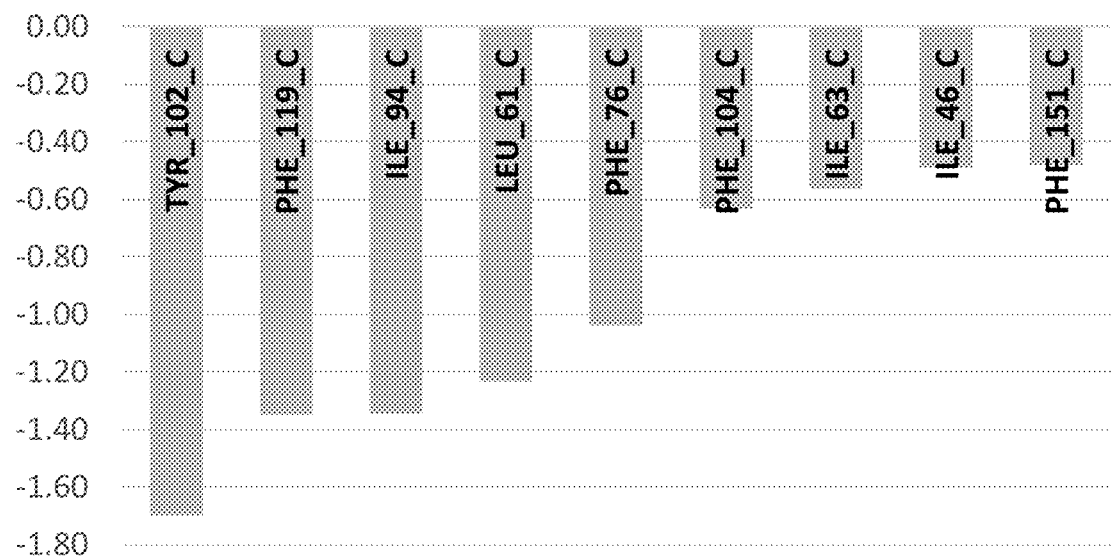
Figure 2I:
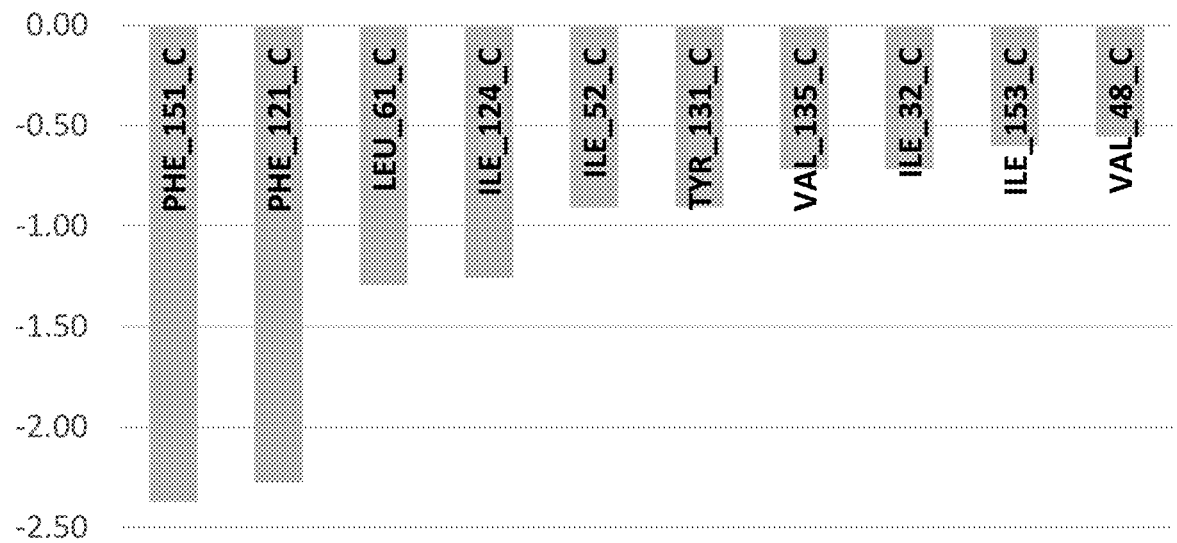
Figure 2I:
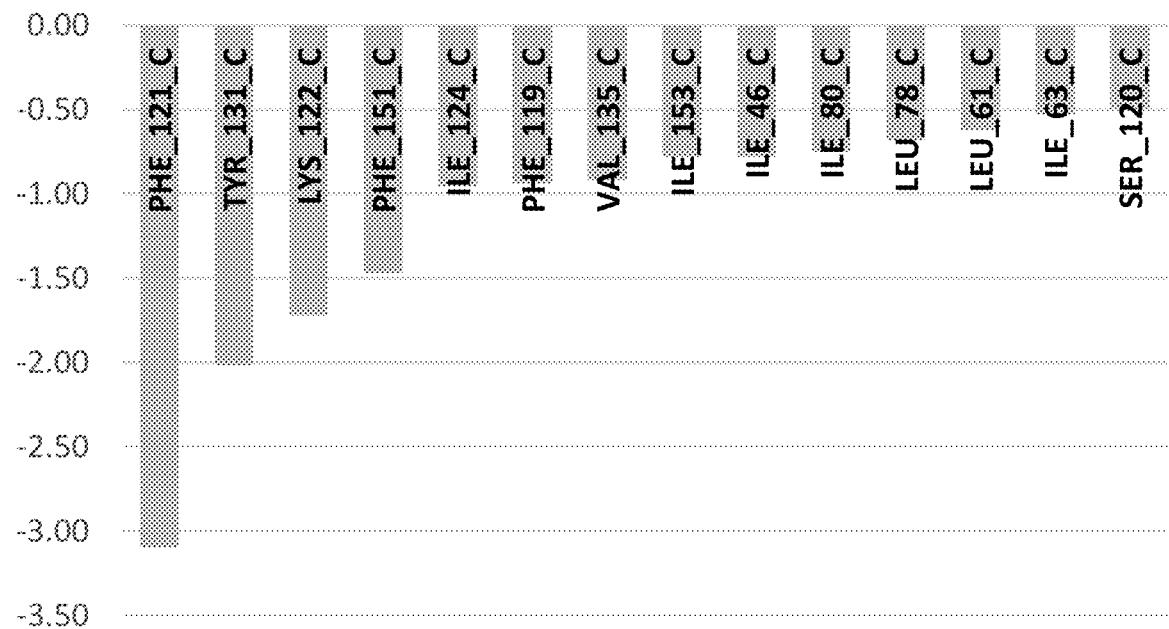
Figure 2J:
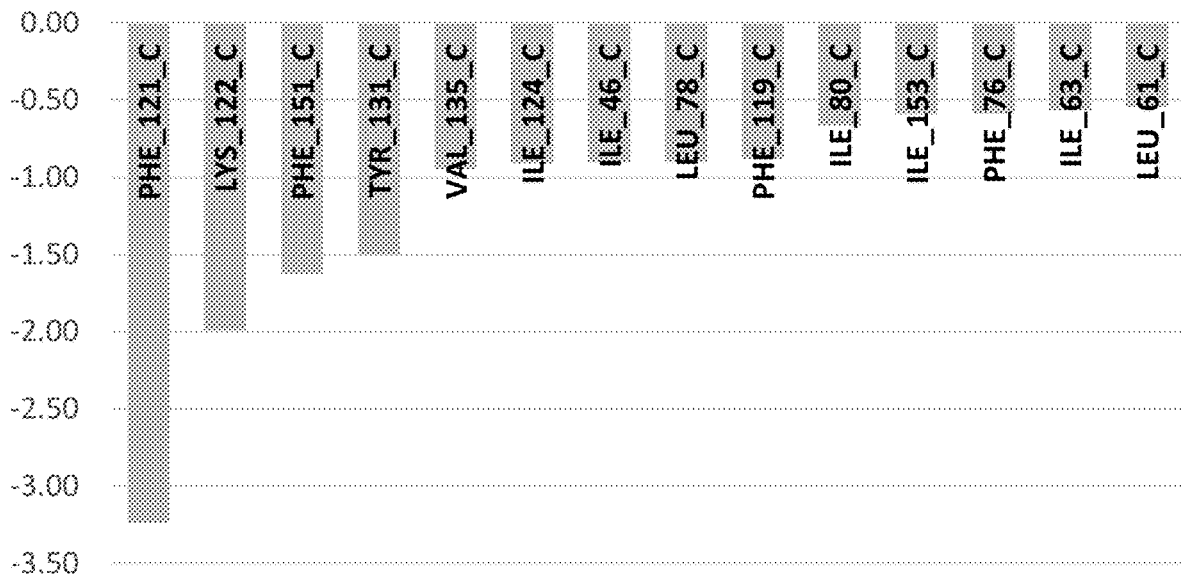
Figure 2J:
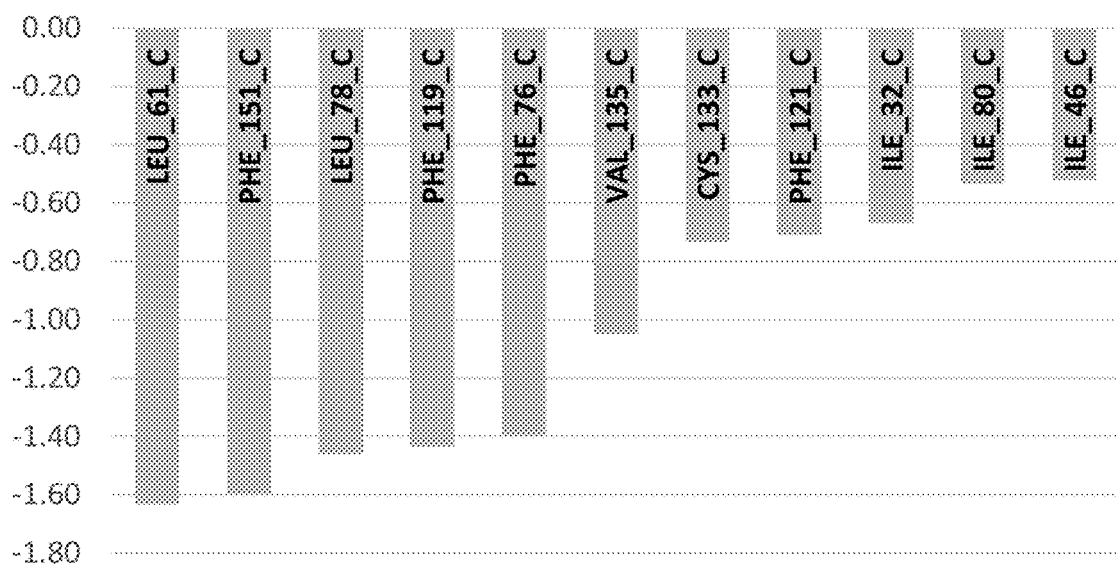
Figure 2K:
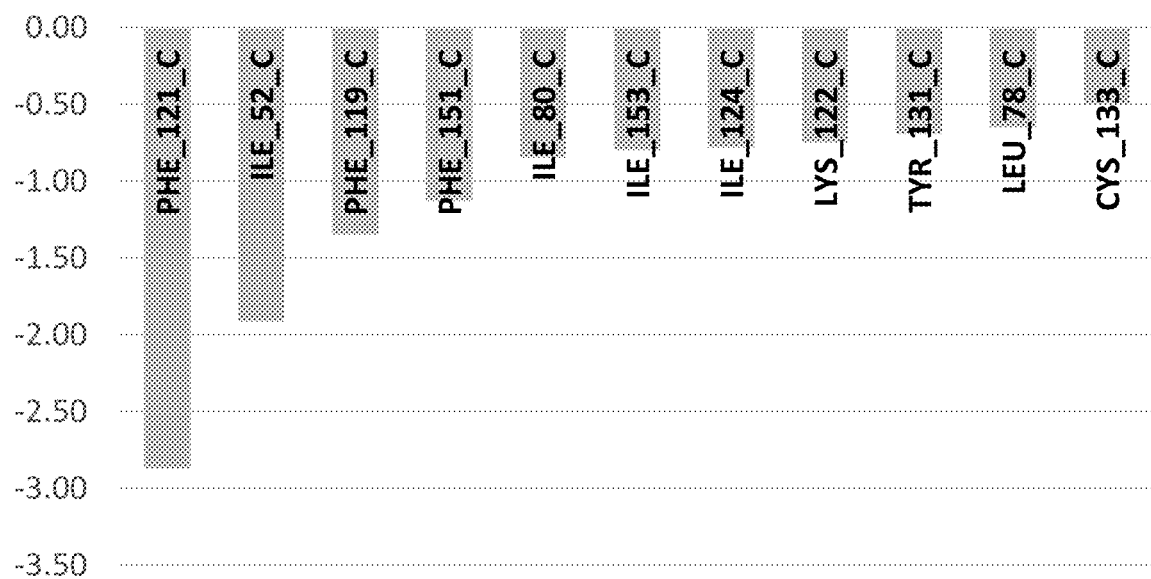

FIG. 1L presents the individual residue contributions of SEQ ID Nos. 4-8, 12 and 13 (which appear on both the CD14 and MD2 peptide design outputs) to the interaction with CD14, according to some embodiments of the invention. The MD2 individual residue contributions of these SEQ ID Nos. are presented on FIGS. 1B-1D and 1F-1G.

FIGS. 2A-2K presents MD2 co-receptor calculated binding energies for each peptide of SEQ ID Nos. 1-22, according to some embodiments of the invention. Only contributions more significant than −0.5 kcal/mol are shown. Activation interactions (in SEQ ID Nos. 1-8, 16-19, 21, 22) are shown in FIGS. 2A-2D, 2H (bottom), 2I, 2J (bottom) and 2K, whereas inhibitory interactions (in SEQ ID Nos. 9-15 and 20) are shown in FIGS. 2E-2G, 2H (top) and 2J (top). In cases where the interactions are weak, the receptor residues are shown in faint colours (SEQ ID Nos. 7 and 8). The vertical axis lists the amino acid's binding free energy contribution in Kcal/mol and the horizontal axis lists the amino acid type number and chain.

It is evident from FIGS. 1A-1L and 2A-2K that in case of all peptides, mostly hydrophobic residues (mainly Phe, Leu, Ile, Trp, Met) of the peptides and hydrophobic residues of the co-receptor interact and provide the majority of the binding energy contributions. It is noted that the numeration of the MD2 amino acids in FIGS. 2A-2K is consistent with the numeration of the Protein Data Bank (PDB) entry 2Z65, with chain C designating the MD2 co-receptor for SEQ ID Nos. 1, 2 and 4-22. In SEQ ID No. 3, the B chain designates TLR4 while the D chain designates MD2. In all cases MD2 residues have the same numeration.

Specifically, FIGS. 2A-2K show the following amino acids of the MD2 co-receptor to prevail in the interaction with the peptides of Table 1:

The phenylalanine residue number 121 is significantly involved in all activator/inhibitor interactions (SEQ ID Nos. 1-22).

The interaction with phenylalanine 119 is a major binding energy contributor in SEQ ID Nos. 1, 3, 4, 5, 6, 7, 9, 11, 12, 15, 16, 19, 20, 21 and 22. (It is noted that SEQ ID No. 7, listed above as an activator with respect to CD14 is also a weak activator with respect to MD2.)

Phenylalanine 151 is a major binding energy contributor in SEQ ID Nos. 1, 3, 4, 5, 6, 7, 8, 9, 11, 12, 13, 14, 16, 17, 19, 20, 21 and 22.

Phenylalanine 76 is a major binding free energy contributor in SEQ ID Nos. 1, 2, 3, 4, 5, 7, 8, 9 12, 20 and 21, making it more prevalent in TLR4 activators (7/14) than inhibitors (3/8).

Tyrosine 102 is a significant binding free energy contributor in SEQ ID Nos. 1, 2, 3, 6, 8, 13 and 16, showing a higher prevalence in activators (6/14) than inhibitors (1/8).

Tyrosine 131 is a significant binding free energy contributor in SEQ ID Nos. 1, 2, 4, 5, 9, 13, 14, 15, 17, 19, 20 and 22. with a similar prevalence in inhibitors (5/8) and activators (7/14).

Isoleucine 80 is a significant binding free energy contributor in SEQ ID Nos. 1, 2, 3, 4, 5, 7, 8, 9, 11, 12, 13, 14, 15, 19, 20, 21 and 22.

Isoleucine 32 is a significant binding free energy contributor in SEQ ID Nos. 1, 3, 6, 7, 15 and 21, showing a higher prevalence in activators (4/8), than inhibitors (1/7).

Isoleucine 46 is a significant binding free energy contributor in SEQ ID Nos. 1, 6, 8, 9, 12, 13, 14, 16 and 19, showing a slightly higher prevalence in inhibitors (4/8) than activators (5/14).

Isoleucine 153 is a significant binding free energy contributor in SEQ ID Nos. 1, 2, 3, 4, 5, 6, 7, 9, 13, 14, 15, 16, 17, 19, 20 and 22.

Isoleucine 52 is a significant binding free energy contributor in SEQ ID Nos. 1, 3, 4, 5, 6, 9, 11, 12, 15 and 22.

Leucine 61 is a significant binding free energy contributor in SEQ ID Nos. 1, 2, 3, 4, 5, 6, 7, 8, 9, 11, 12, 13, 14, 16, 17, 19 and 20.

Leucine 78 is a significant binding free energy contributor in SEQ ID Nos. 1, 2, 3, 4, 5, 7, 8, 9, 11, 12, 13, 19, 20 and 22, showing a similar prevalence in activators (9/14) than inhibitors (5/8).

Lysine 122 is a significant binding free energy contributor in SEQ ID Nos. 20 and 22.

These residues thus define a hydrophobic pocket (see FIGS. 4A and 4B below) within MD2, to which the peptides bind. Hence, any peptide binding to this pocket may interact with the TLR4-MD2 complex as activator or inhibitor. Since the MD2 pocket permits multiple backbone conformation arrangements there are multiple discrete patterns for the peptides. It is noted that Table 1 presents both examples for such multiple different patterns, as well as examples for peptides having a common backbone, such as SEQ ID Nos. 4, 5 and 9, as well as example non-natural peptide derivatives on that backbone; ID Nos. 4 (M1) and 4(M2). FIGS. 5A-5L below demonstrate for some of the peptides, namely SEQ ID Nos. 4-6, 8, 9 and 12 the range of possible sequence variations with respect to their specific backbones. It is emphasized that all modifications which provide a significant binding energy are candidates as effectors of TLR4, as discussed below.

Figure 3A:
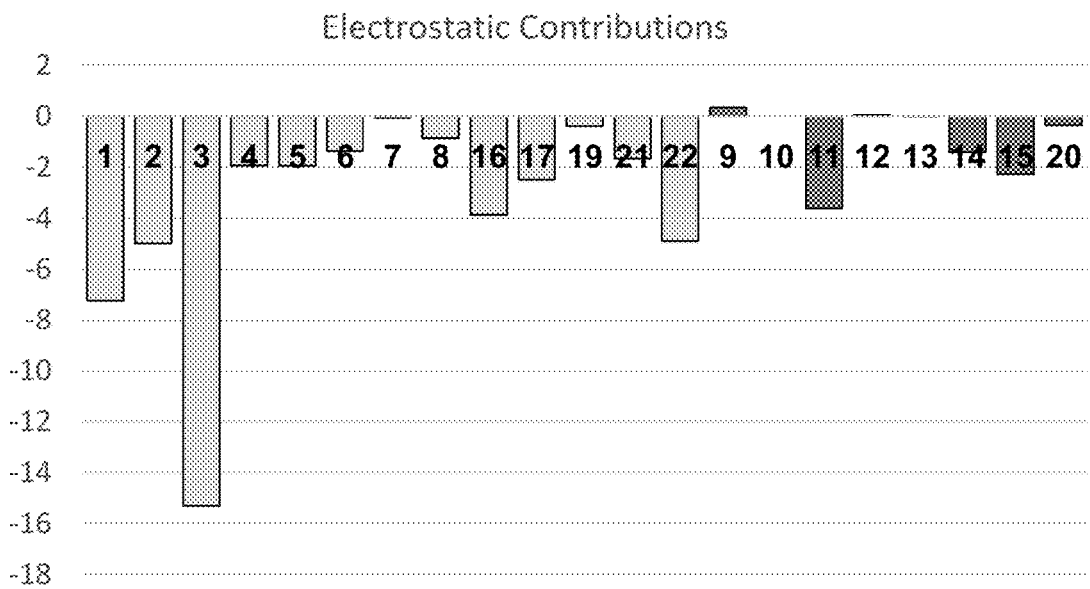
FIG. 3A presents a calculated electrostatic binding energy component for each peptide of SEQ ID Nos. 1-22 binding to the TLR4/MD2 complex, according to some embodiments of the invention.

FIG. 3A presents a calculated electrostatic binding energy component for each peptide of SEQ ID Nos. 1-22 binding to the TLR4/MD2 complex, according to some embodiments of the invention. The vertical axis lists the electrostatic contributions in Kcal/mol and the horizontal axis lists the peptide SEQ ID Nos., including activators (SEQ ID Nos. 1-8, 16, 17, 19, 21 and 22; left) and inhibitors (SEQ ID Nos. 9-15, 20; right). The relatively minor electrostatic binding free energy contributions were more prevalent in the activators (average=−4.2 Kcal/mol) than in the inhibitors (average=−1.1 Kcal/mol), although not statistically significant (two tailed T-Test P-Value of 0.18).

Figure 3B:
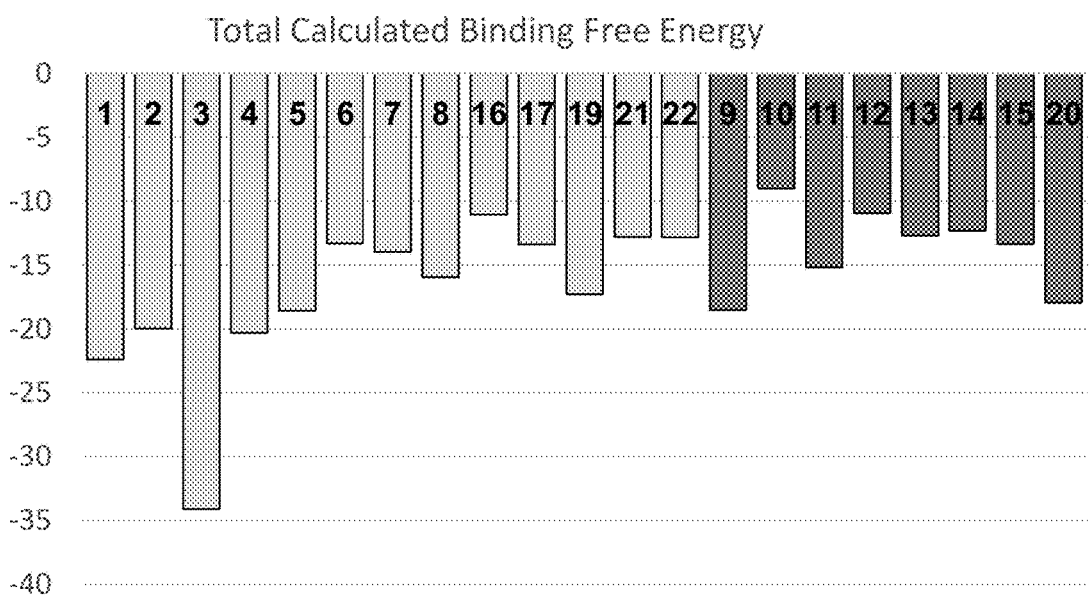
FIG. 3B presents a calculated total binding free energy for each peptide of SEQ ID Nos. 1-22 binding to the TLR4/MD2 complex, according to some embodiments of the invention.

FIG. 3B presents a calculated total binding free energy for each peptide of SEQ ID Nos. 1-22 binding to the TLR4/MD2 complex, according to some embodiments of the invention. The vertical axis lists the free energy of binding in Kcal/mol (1 calculated Kcal~0.5 real Kcal) and the horizontal axis lists the peptide SEQ ID Nos., including activators (SEQ ID Nos. 1-8, 16, 17, 19, 21 and 22; left) and inhibitors (SEQ ID Nos. 9-15, 20; right). The total calculated binding free energy was insignificantly lower for the activators (average=−17.4 Kcal/mol) than inhibitors (average=−13.7 Kcal/mol) (two tailed T-Test P-Value of 0.14). The overall electrostatic binding free energy contribution as a percentage of the total binding free energy was higher in the activators (average=19%) than inhibitors (average=6% Kcal/mol), statistically significant (two tailed T-Test P-Value of 0.05). These differences should be taken with caution, as there is a small, uneven number of molecules compared.

To conclude, FIGS. 3A and 3B illustrate that the activator peptides (SEQ ID Nos. 1-8, 16, 17, 21 and 22) show slightly lower calculated binding free energies, with a larger occupied volume in the MD2 pocket, with a larger electrostatic component than inhibitor peptides (SEQ ID Nos. 9-15 and 20).

Figure 4A:
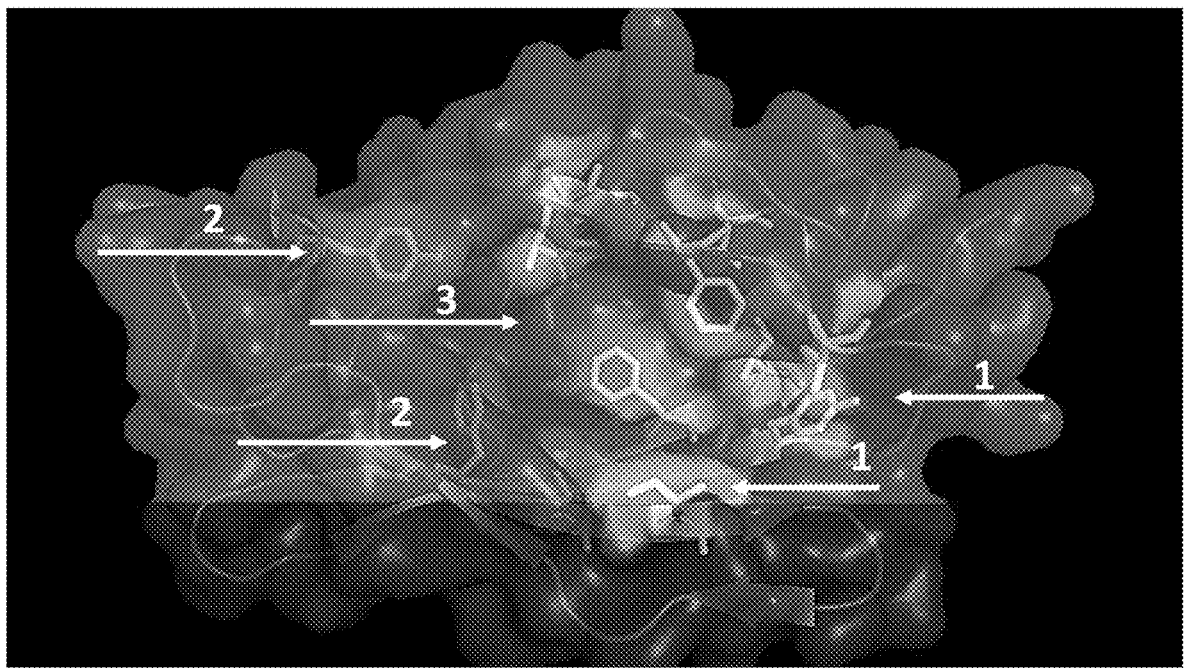
FIG. 4A schematically illustrates critical binding areas in the MD2 co-receptor, with proposed activator/inhibitor prevalence, according to some embodiments of the invention.
Figure 4B:
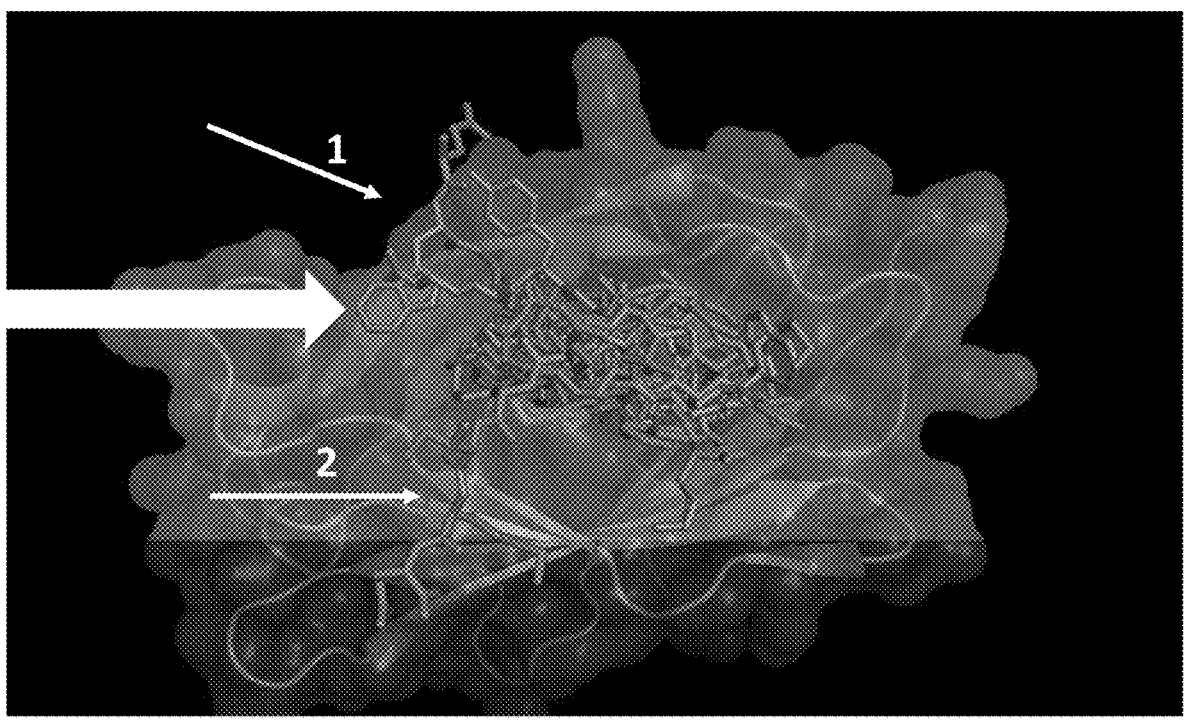
FIG. 4B schematically illustrates binding modes of activators/inhibitors in the MD2 co-receptor, according to some embodiments of the invention.

FIGS. 4A and 4B illustrate comparisons between regions bound by the activator population and regions bound by the inhibitor population.

FIG. 4A schematically illustrates critical binding areas in the MD2 co-receptor, with proposed activator/inhibitor prevalence, according to some embodiments of the invention. The MD2 solvent-accessible surface area is displayed in grey. Areas that were found to be critical for the binding of both activators and inhibitors are marked with arrows numbered 1, areas which were found to be more critical for activator binding are marked with arrows numbered 2, and areas which were found to be more critical for inhibitor binding are marked with arrow numbered 3 (see the list above).

FIG. 4B schematically illustrates binding modes of activators/inhibitors in the MD2 co-receptor, according to some embodiments of the invention. The binding modes of TLR4 activators (SEQ ID Nos. 1-8, 16, 17, 19, 21 and 22) are marked with arrows numbered 1and are compared to the binding modes of TLR4 inhibitors (SEQ ID Nos. 9-15, 20) which are marked with arrows numbered 2. FIG. 4B illustrates a tendency for the activators to interact with the area marked by the thickarrow (although not all activators interact in this manner). These calculations, presenting binding energy data and spatial binding constraints, suggest a range of peptides that may be used to bind and affect the MD2 co-receptor and the TLR4 binding complex. Such peptides are characterized by a wide range of possible position replacements for each peptide backbone.

Figure 5A:
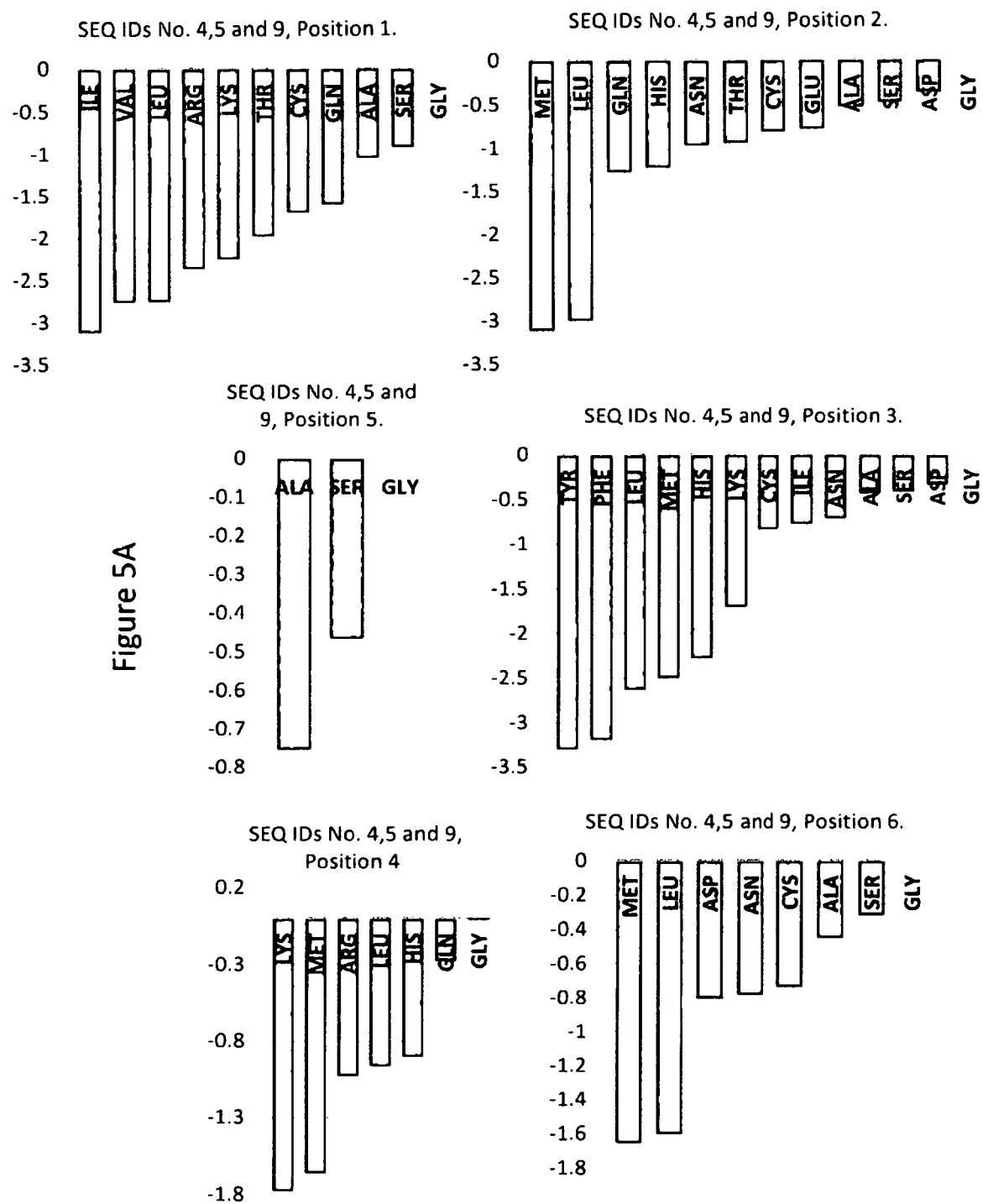
Figure 5B:
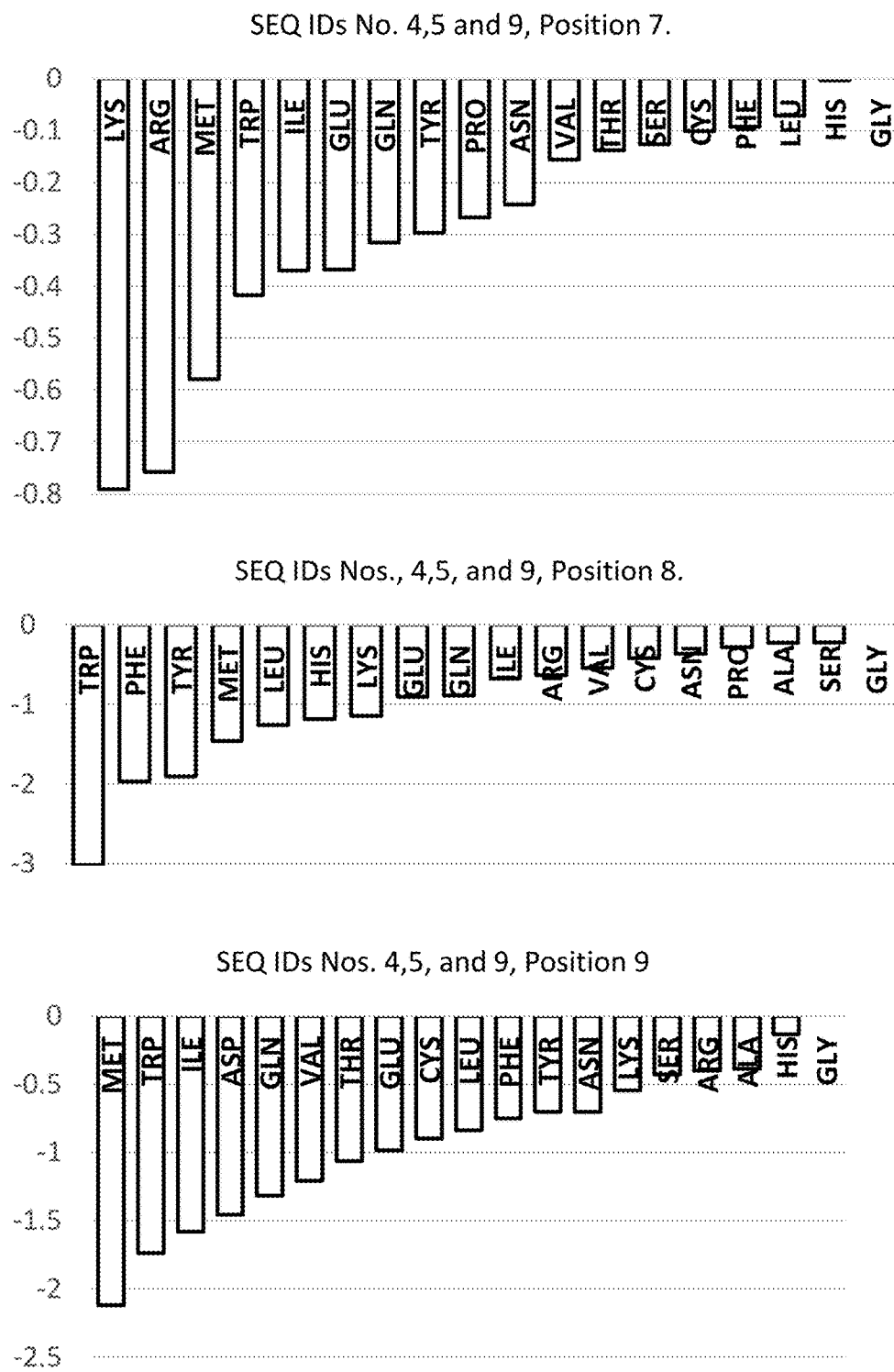

FIGS. 5A-5L illustrate substitution variation ranges for all amino acid positions in SEQ ID Nos. 4-6, 8, 9 and 12 peptides, according to some embodiments of the invention. While the bioactivity of the peptides SEQ ID Nos. 1-22 is shown below in FIGS. 6A-6D and 7A-7X, the bioactivity of the peptides resulting from substitutions to one or more positions in these peptides according to FIGS. 5A-5L was not tested (with the exception of the example variants shown in Table 1) and it is hence not proven that substituted peptides retain the respective peptide's bioactivity. Nevertheless, substituted peptides according to the data presented in FIGS. 5A-5L are considered plausible candidates as TLR4 effectors, and are considered part of the present disclosure FIGS. 5A and 5B show the residues that can be incorporated in each position, and the individual binding energy contribution for every possible amino-acid incorporated in the relevant position, with respect to peptides SEQ ID Nos. 4, 5 and 9 which are rich in MD2 binding "hot-spots" and share the same backbone model. Interestingly, SEQ ID Nos. 4 and 5 shared a backbone conformation in binding CD14 that differs from the one used to bind MD2, and is incompatible with the sequence of peptide SEQ ID No. 9. It is noted that SEQ ID Nos. 4 and 5 incorporate more hydrogen bond donors/acceptors and act as activators whereas SEQ ID No. 9 incorporates more hydrophobic residues. As can be seen in FIGS. 5A and 5B, some positions allow diverse amino-acid substitutions, while retaining a significant binding energy contribution while position 5 allows for only the incorporation of the small volume residues glycine, alanine and serine, all with minor binding energy contribution. As shown with SEQ ID Nos. 4, 5 and 9, numerous residue substitutions can be made while maintaining an overall similar total calculated binding energy to MD2 (shown in FIG. 3B).

The data presented in FIGS. 5A and 5B suggest the peptide having SEQ ID No. 23, i.e., $X_1X_2X_3X_4X_5X_6X_7X_8X_9$, with $X_1$=I, V, L, R, K, T, C, Q, A, N, S or G, $X_2$=M, L, Q, H, N, T, C, E, A, S, D or G, $X_3$=Y, F, L, M, H, K, C, I, N, A, S, D or G, $X_4$=K, M, R, L, H, Q or G, $X_5$=A, S or G, $X_6$=M, L, D, N, C, A, S or G, $X_7$=K, R, M, W, I, E, Q, Y, P, N, V, T, S, C, F, L, H or G, $X_8$=W, F, Y, M, L, H, K, E, Q, I, R, V, C, N, P, A, S, or G and $X_9$=M, W, I, D, Q, V, T, E, C, L, P, Y, N, K, S, R, A, H, or G—as binding to TLR4. Any of these combinations may be considered a candidate for a TLR4 binding peptide. It is noted that the specific combinations may be selected with respect to delivery considerations of the peptide to the target tissue, e.g., with respect to the peptide's solubility and biological interactions that may be determined experimentally along the lines exemplified herein for specific peptide examples.

Figure 5C:
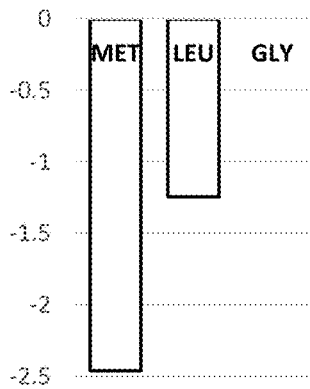
Figure 5C:
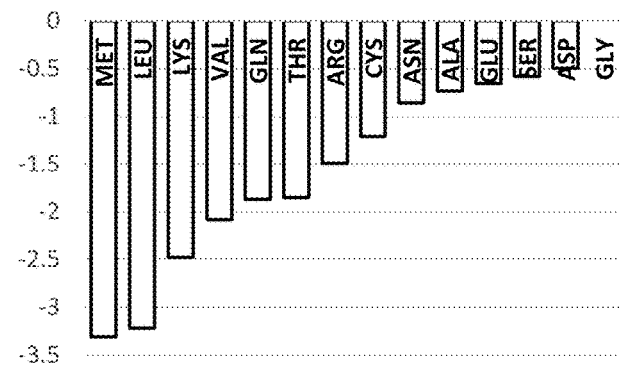
Figure 5C:
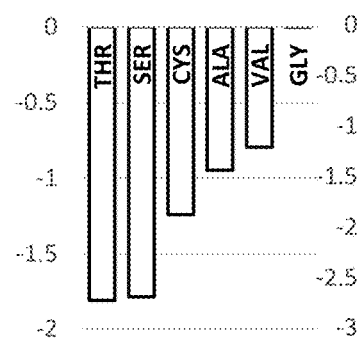
Figure 5C:
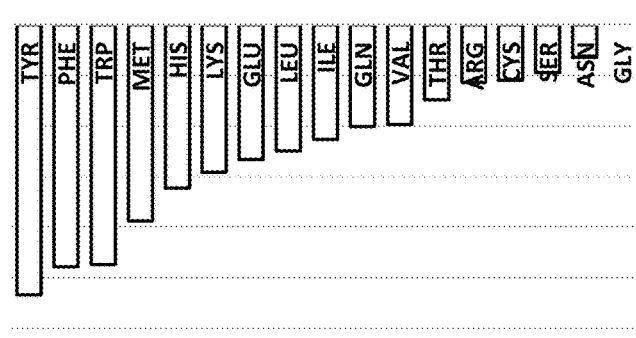
Figure 5C:
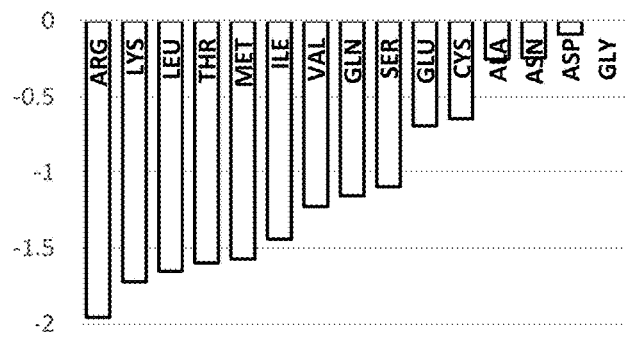
Figure 5C:
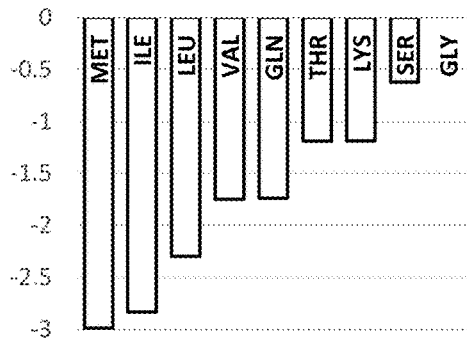
Figure 5E:
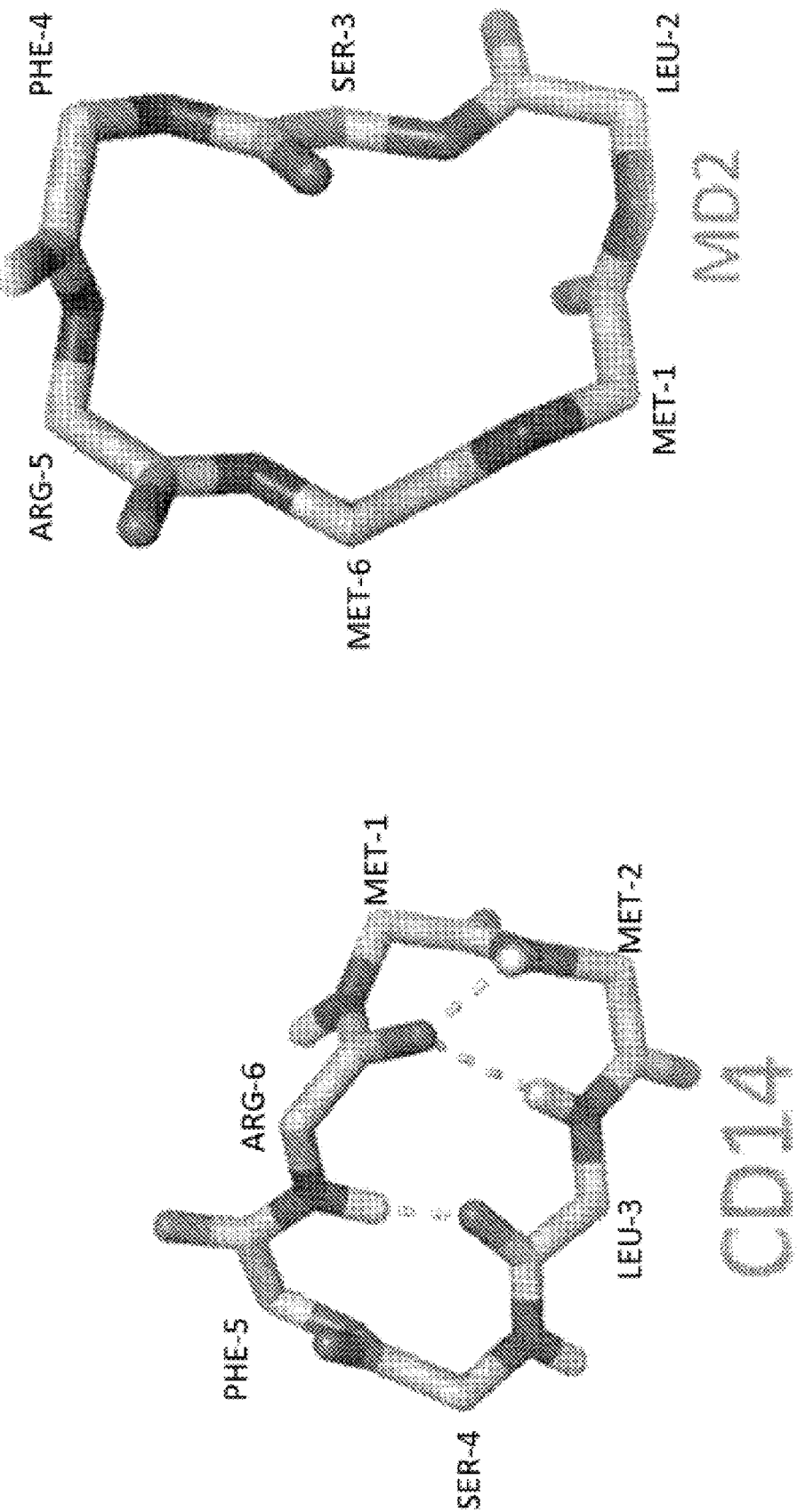
Figure 5F:
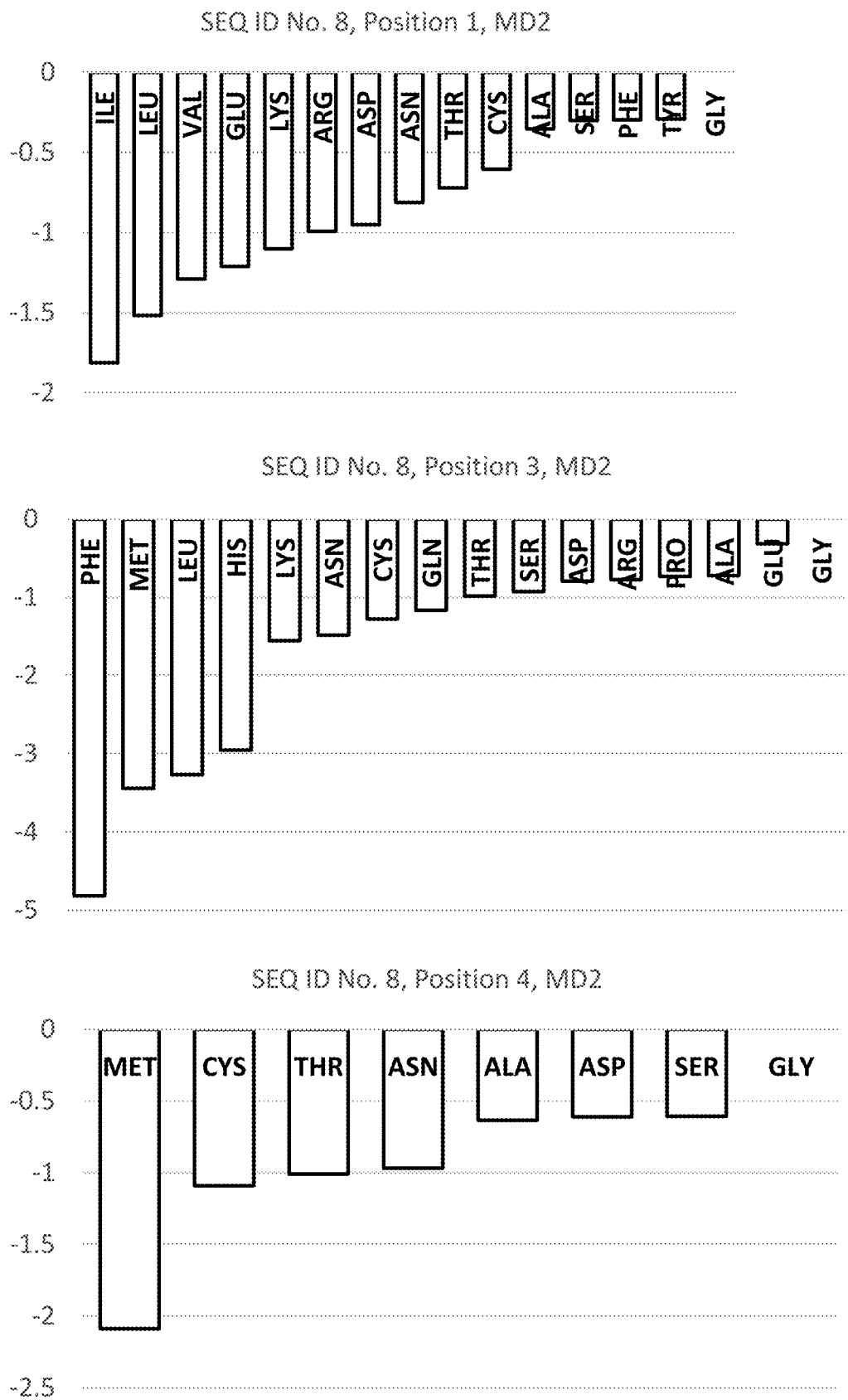
Figure 5G:
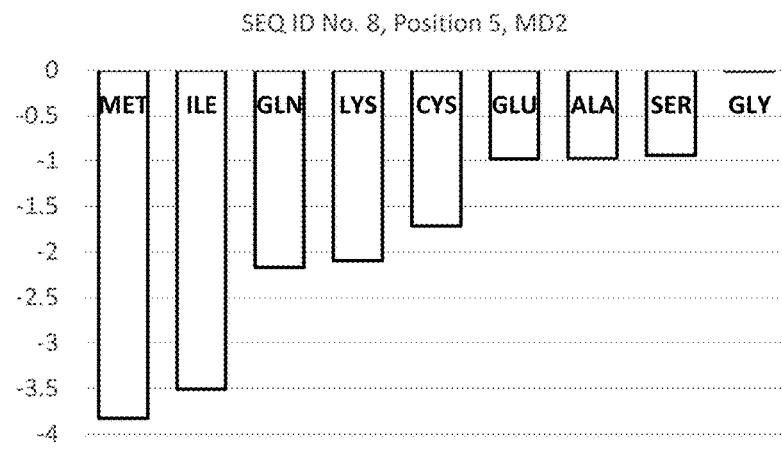
Figure 5G:
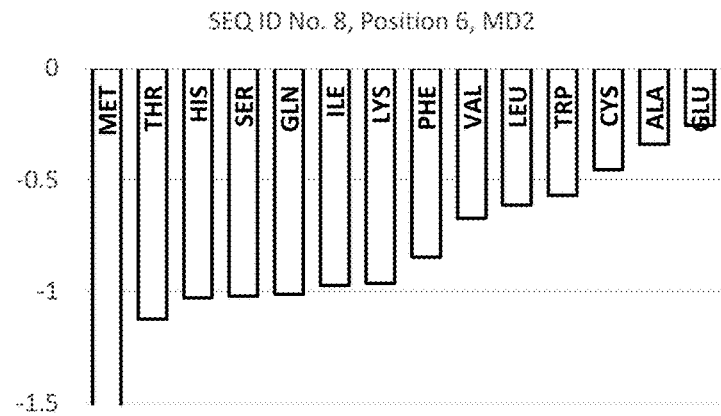
Figure 5G:
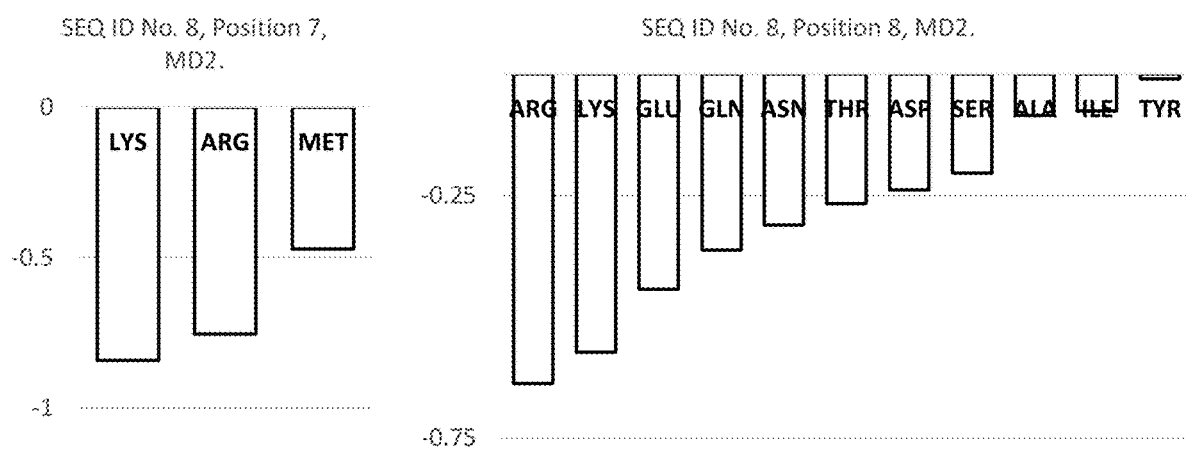
Figure 5H:
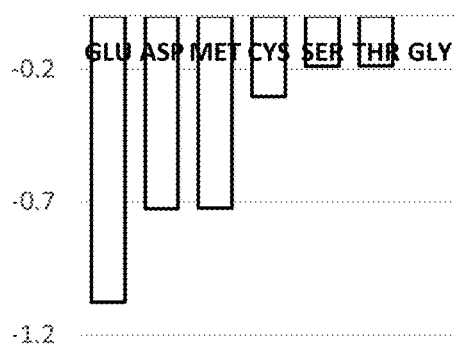
Figure 5H:
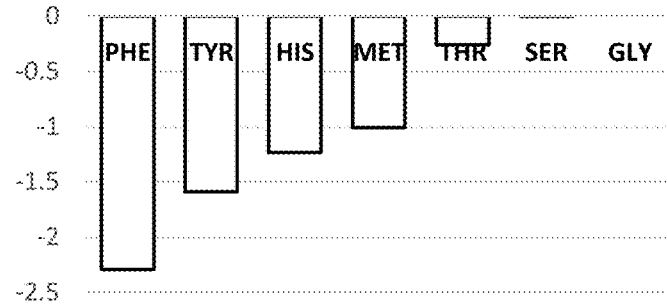
Figure 5H:
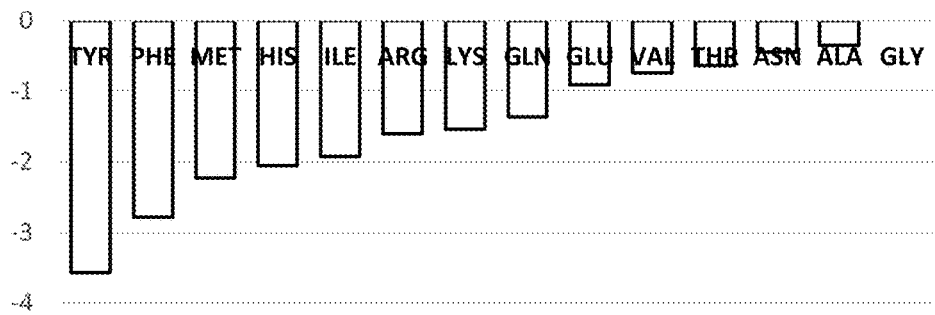
Figure 5H:
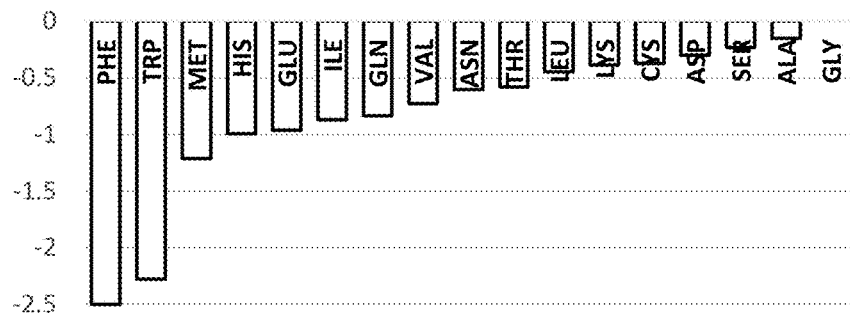
Figure 5H:
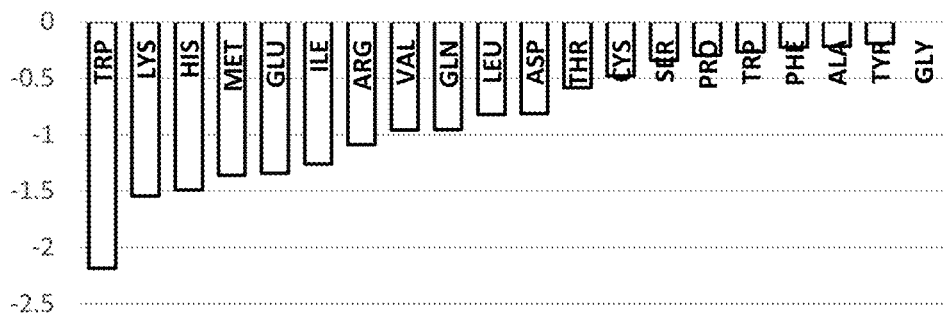
Figure 5I:
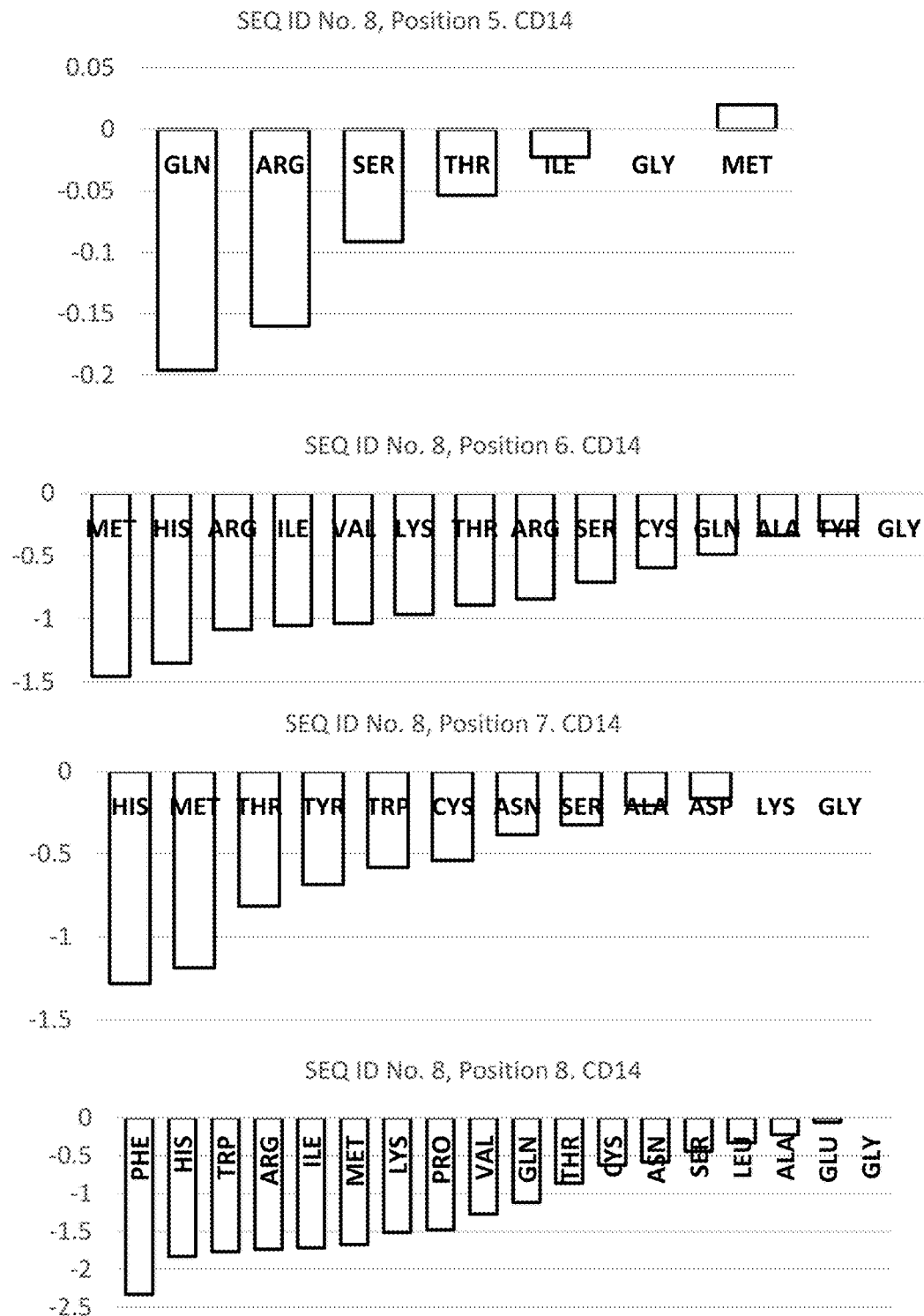
Figure 5J:
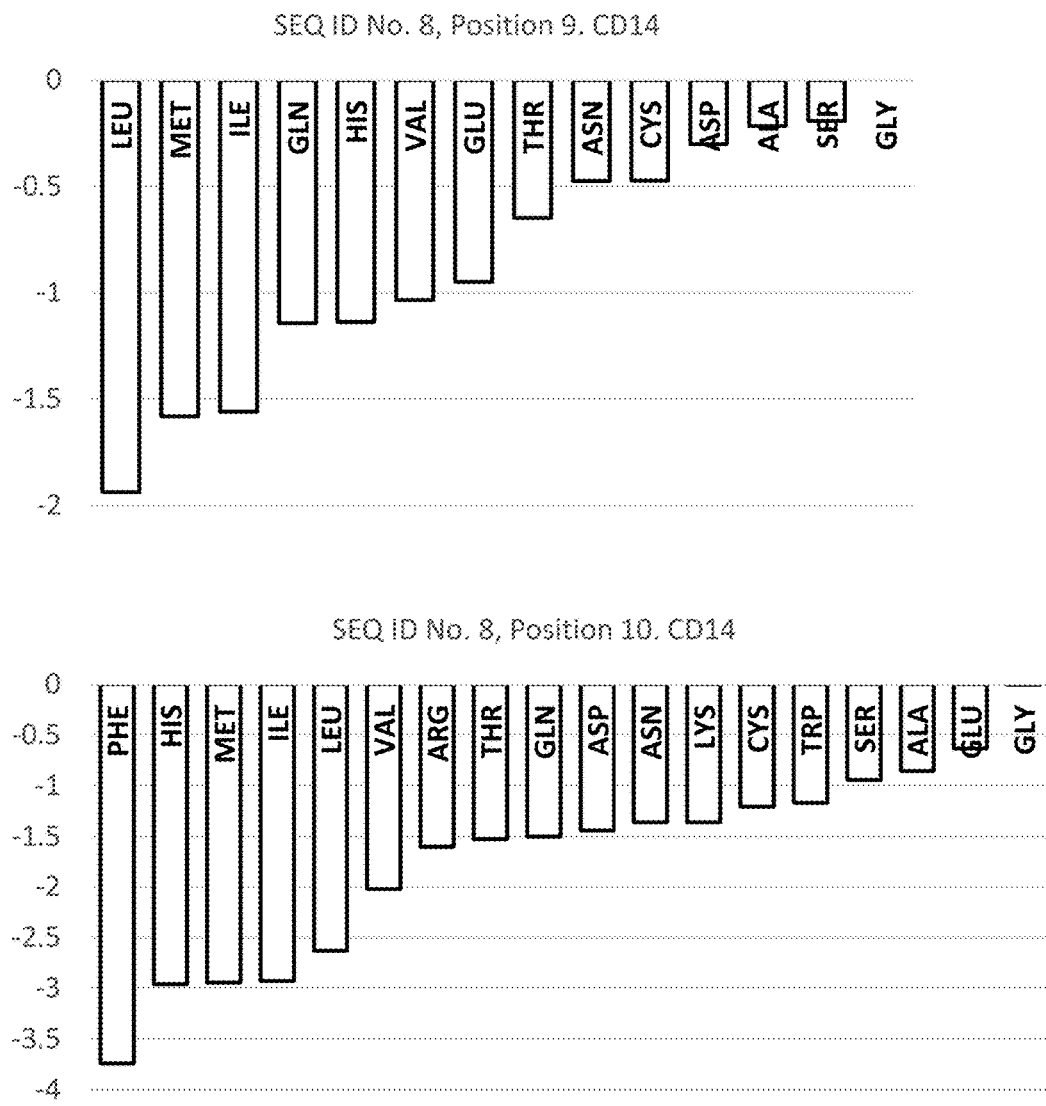
Figure 5L:
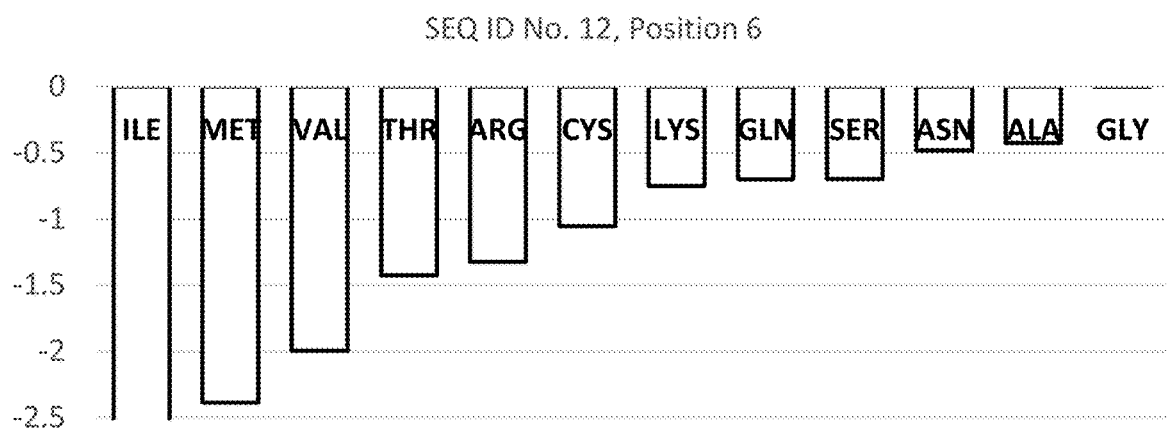
Figure 5L:
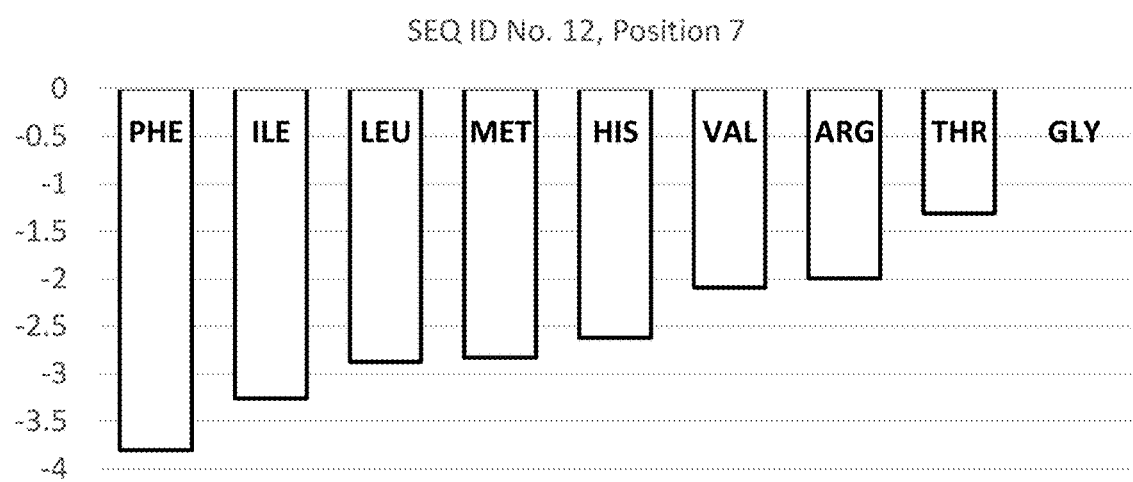
Figure 6A:
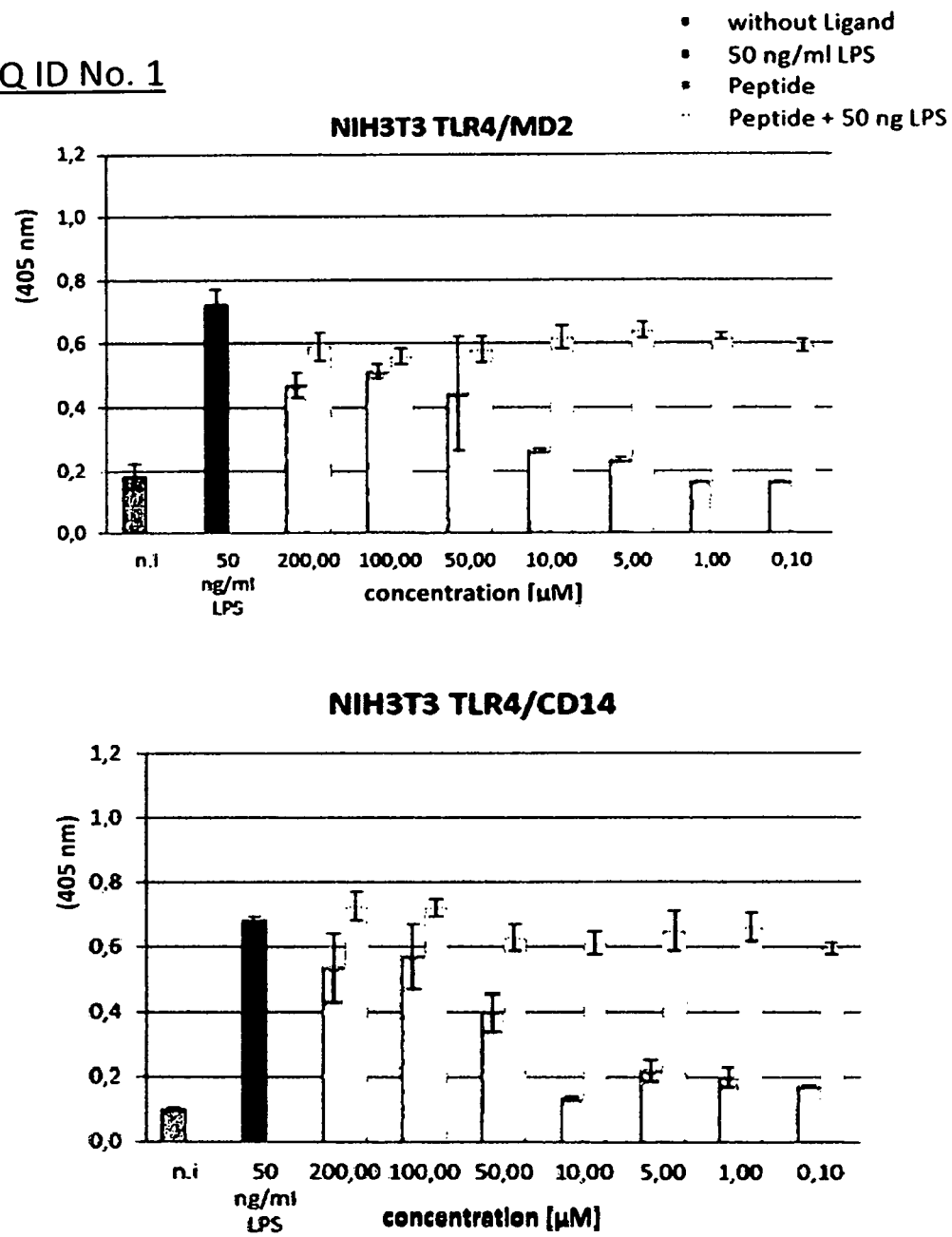
FIGS. 6A-6D present peptide activity using NIH3T3 cells that express TLR4, with either the MD2 co-receptor (top) or CD14 co-receptor (bottom), for peptides of SEQ ID Nos. 1, 1(M1), 1(M2) and 1(M3), respectively, according to some embodiments of the invention.
Figure 6A:
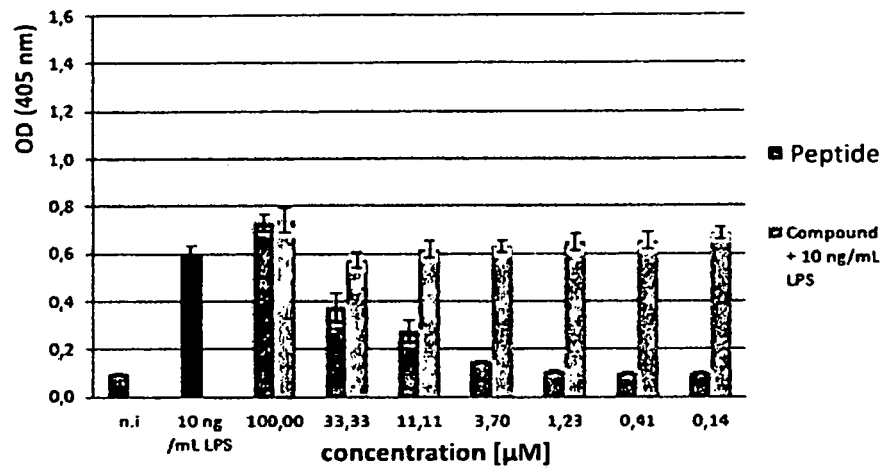
Figure 6A:
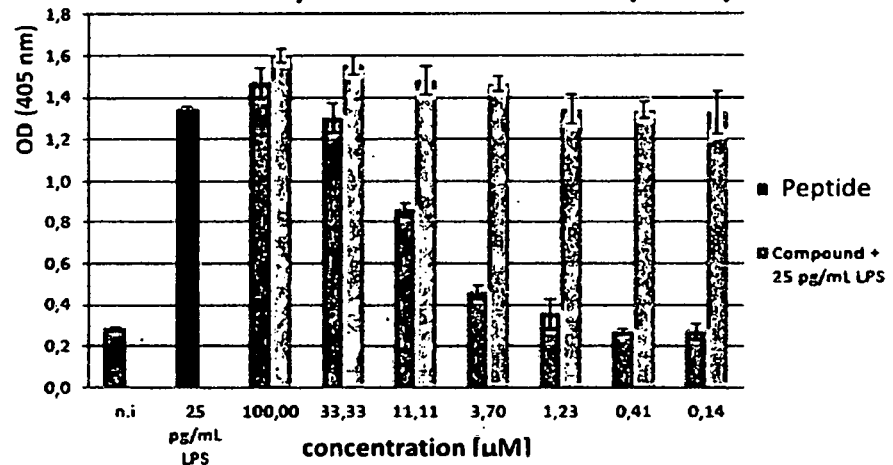
Figure 6A:
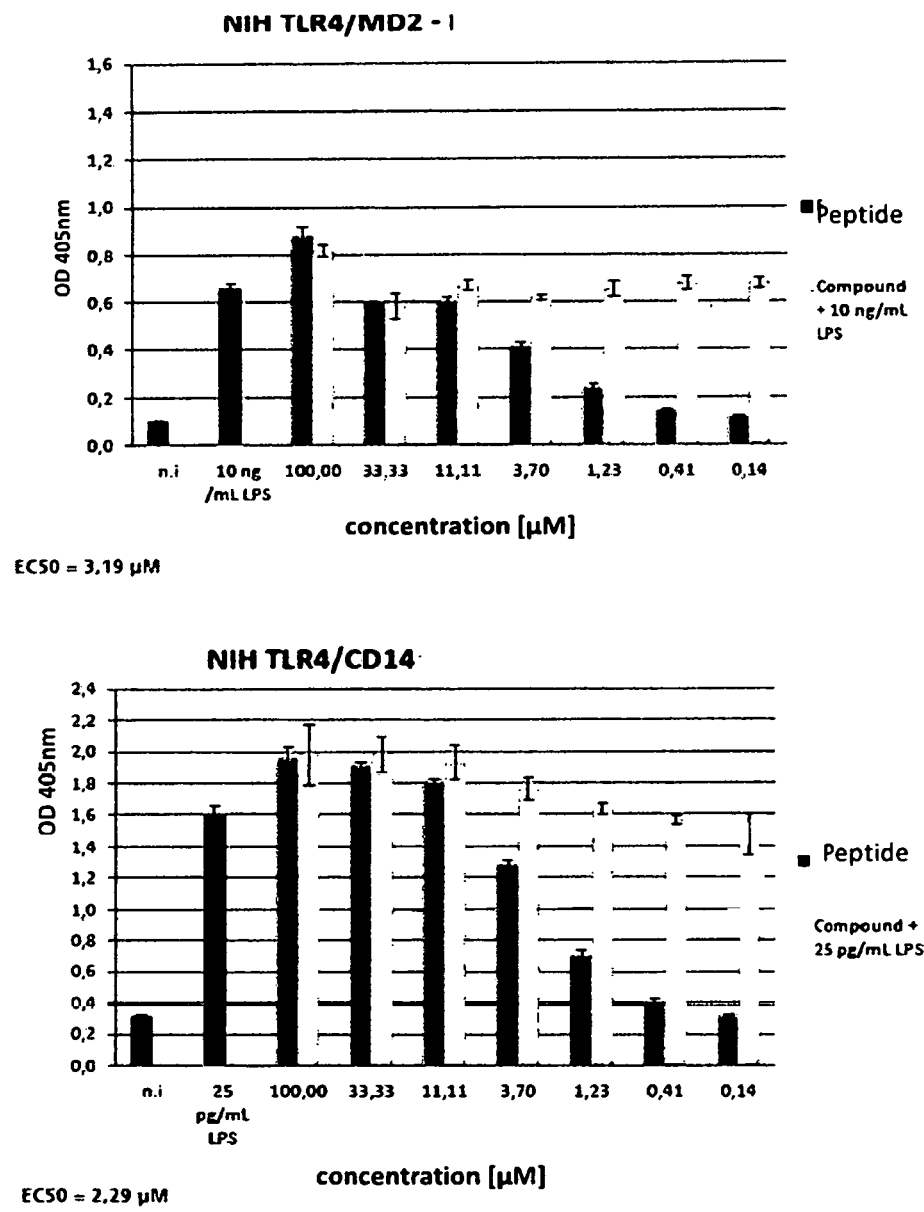
Figure 6A:
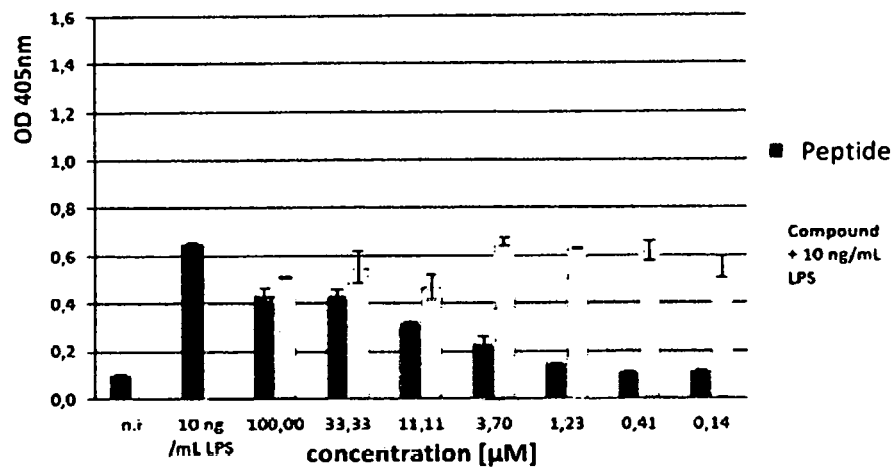
Figure 6A:
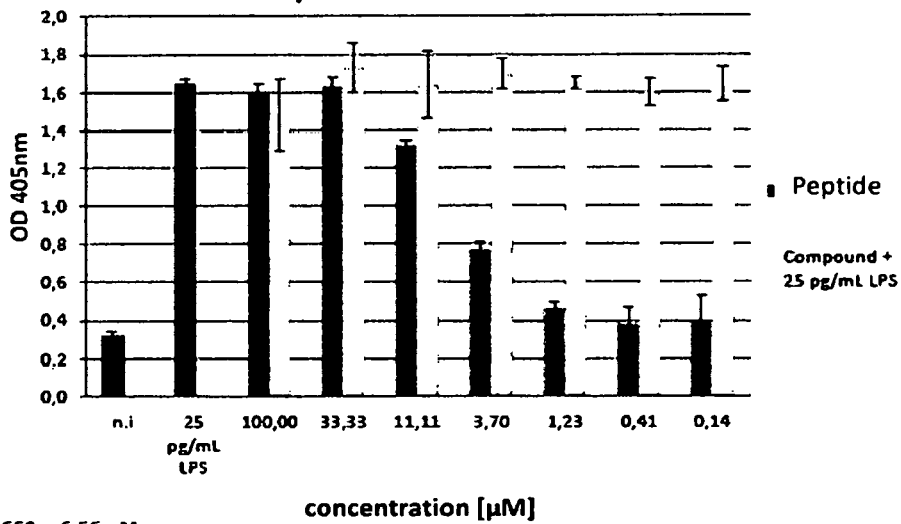
Figure 6B:
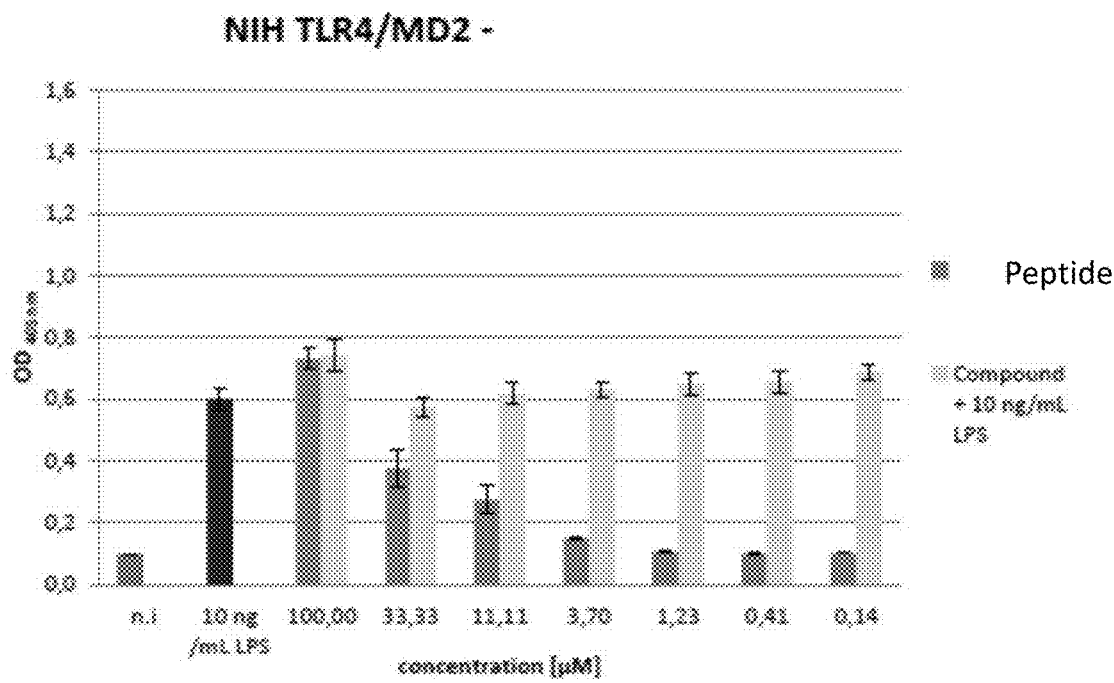
Figure 6B:
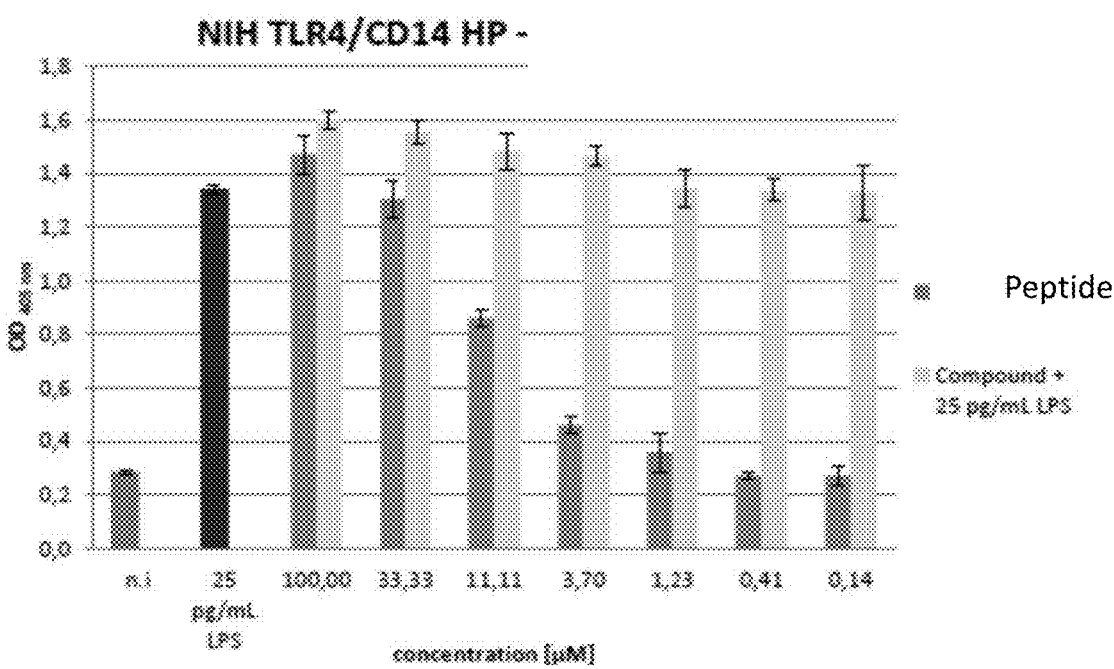
Figure 6C:
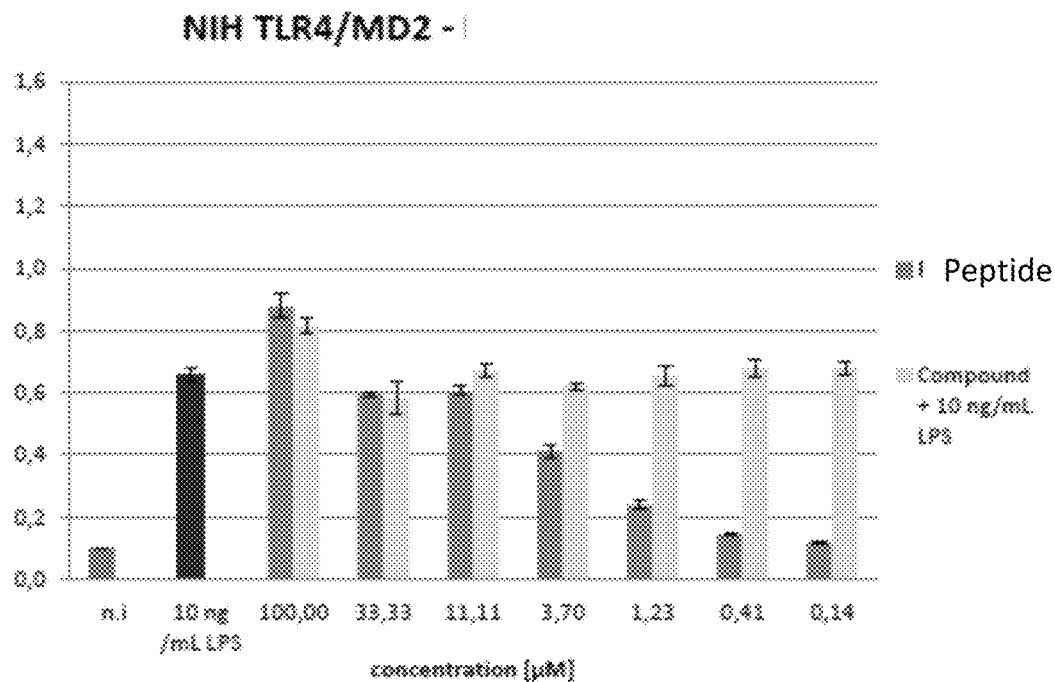
Figure 6C:
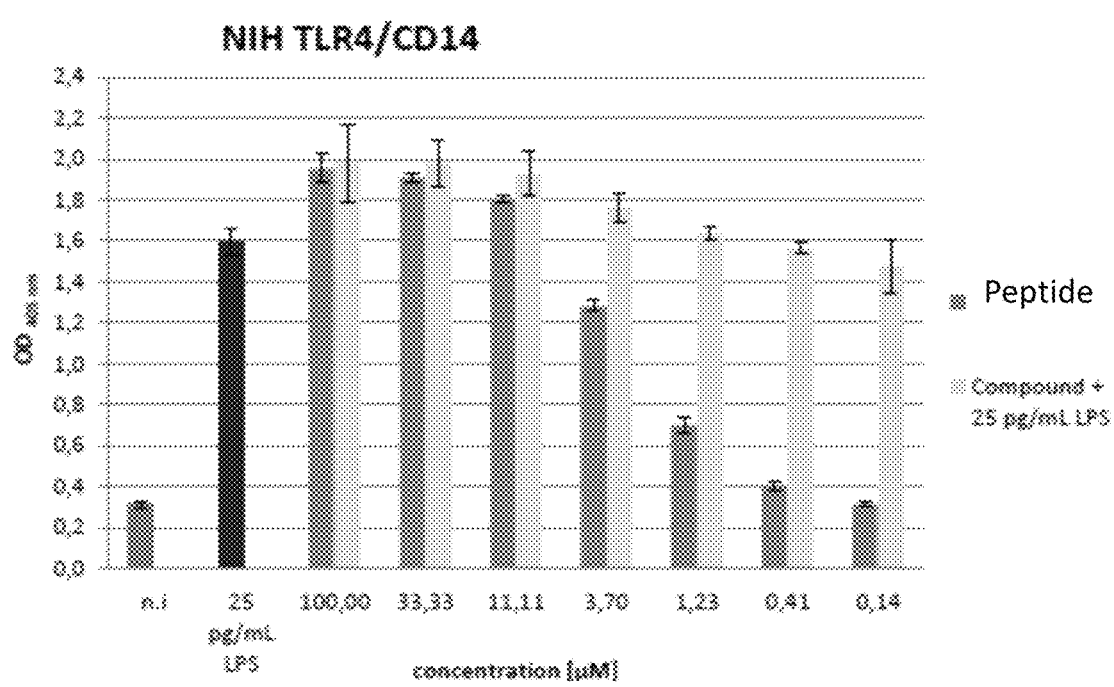
Figure 6D:
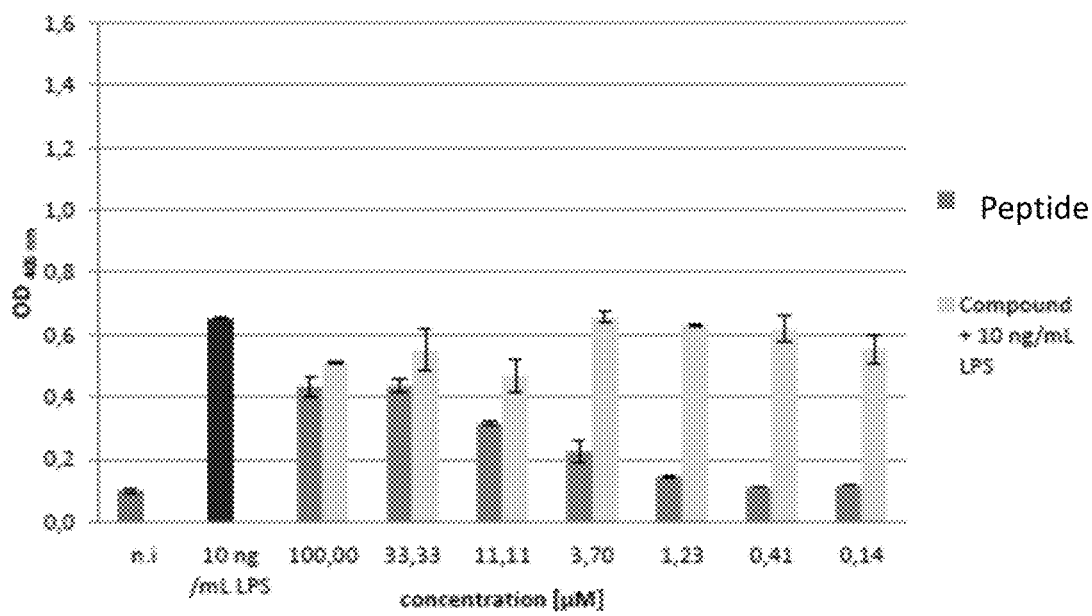
Figure 6D:
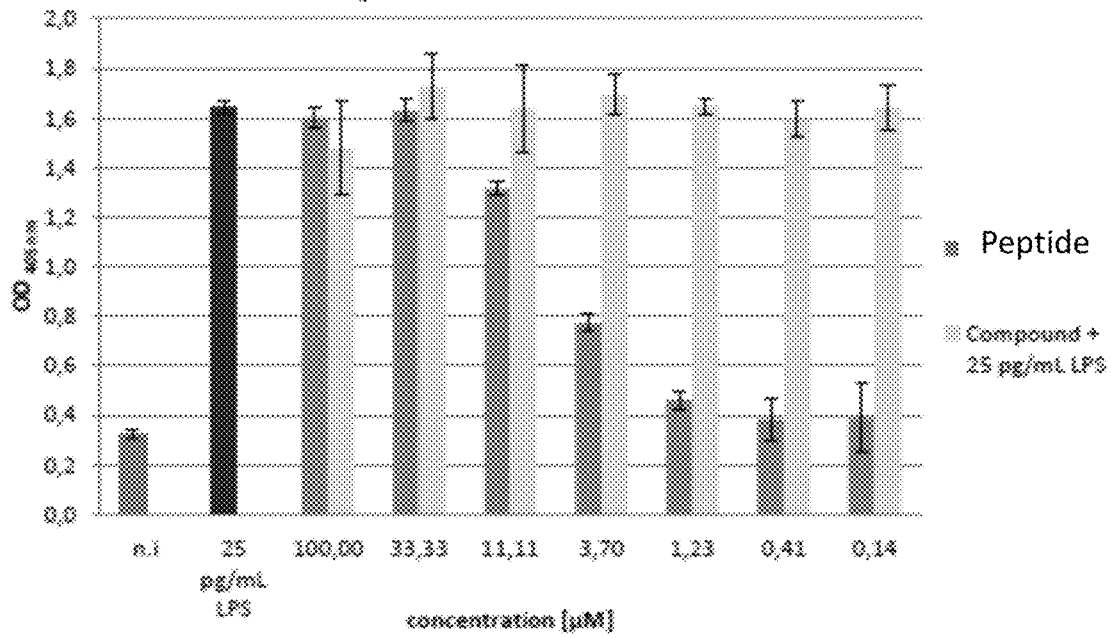

FIGS. 5C-5E show the incorporation of different amino-acid residues into the backbone of peptide SEQ ID No. 6 and their binding energy contribution. This is shown separately for MD2 and CD14. Alterations can be either used for the creation of a MD2/CD14 selective peptide or, as in the case of SEQ ID No. 6, a peptide which binds both. Position 1 is highly restricted in the binding of MD2, with only methionine and leucine showing a substantial binding contribution. In binding CD14, position 1 is more permissive, allowing isoleucine to also be used as a significant binding energy contributor, with other residues, including polar ones, also available, although with a reduced binding energy contribution. Position 2 is similar in both models, allowing for the accommodation of methionine, leucine and lysine as significant binding free energy contributors. Position 3 has optimal binding energy contributions for binding MD2 with the polar serine and threonine side-chains, while these are compatible with binding CD14, they are not optimal. The incorporation of methionine or lysine in this position would be optimal for binding CD14 while sacrificing MD2 binding. Position 4 is dominated by the aromatic residues phenylalanine and tyrosine for binding both MD2 and CD14. Position 5 contains hydrophobic and positive charges in the top contributing amino-acids for both CD14, dominated by isoleucine, methionine, histidine, arginine and lysine and MD2, dominated by arginine, lysine and leucine. Position 6 is dominated by methionine for as the optimal amino acid for binding both MD2 and CD14, leucine can also contribute significantly for binding both co-receptors. The backbone conformation varies significantly between the two binding modes; when bound to CD14, the backbone assumes a "closed" conformation, rich with internal hydrogen bonds whereas the binding of MD2 does not form internal hydrogen bonds and occurs in an "open" conformation. Peptides corresponding to substitutions according to the described possibilities, as well as other substitutions that maintain an overall similar total calculated binding energy are considered potential candidates for TLR4 binding peptides.

The data presented in FIGS. 5C-5D suggest the peptide having SEQ ID No. 24, i.e., $c[X_1X_2X_3X_4X_5X_6]$, with $X_1$=M, L or G, $X_2$=M, L, K, V, Q, T, R, C, N, A, E, S, D or G, $X_3$=T, S, C, A, V or G, $X_4$=Y, F, W, M, H, K, E, L, I, Q, V, T, R, C, S, N or G, $X_5$=R, K, L, T, M, I, V, Q, S, E, C, A, N, D or G, and $X_6$=M, I, L, V, Q, T, K, S or G—as binding to TLR4 with co-receptor MD2; and the peptide having SEQ ID No. 25, i.e., $c[X_1X_2X_3X_4X_5X_6]$, with $X_1$=I, L, M, V, T, K, Q, C, R, S, A, E, H or G, $X_2$=L, M, K, R, Q, T, C, N, S, A, E or G, $X_3$=M, K, V, T, C, Q, N, R, A, S, E or G, $X_4$=F, Y, K, H, R, E, L, Q, N, D, S, A or G, $X_5$=I, M, K, V, R, Q, E, C, T, S, A, N or G, and $X_6$=M, L, T, N, K, C, Q, S, A, D, R or G—as binding to TLR4 with co-receptor CD14. FIG.

5E further presents the backbone hydrogen bonds and binding conformation for peptides SEQ ID Nos. 24 and 25 for binding to TLR4 with MD2 and CD14, respectively. Any of these combinations may be considered a candidate for a TLR4 binding peptide. It is noted that the specific combinations may be selected with respect to delivery considerations of the peptide to the target tissue, e.g., with respect to the peptide's solubility and biological interactions that may be determined experimentally along the lines exemplified herein for specific peptide examples.

FIGS. 5F-5J show the residues that can be incorporated in each position of SEQ ID Nos. 26 and 27 which are derived from SEQ ID No. 8, and the individual binding energy contribution for every possible amino-acid incorporated in the relevant position. FIGS. 5F-5J show the contributed binding free energy for each possible amino acid in each position of SEQ ID No. 8 with respect to co-receptors MD2 and CD14. For the binding the MD2 co-receptor, there is a distinct residue attribute pattern: Position 2 of SEQ ID No. 8 can only accommodate glycine when binding MD2. Hydrophobic residues dominate positions 1, 3, 4, 5, 6 and 10. Positions 7 and 8 are dominated by positive residues and position 9 by negative residues. There is also a residue attribute pattern for the binding of CD14: As with MD2, position 2 can only accommodate glycine when binding CD14. With the exception of position 5, all of the other positions are dominated by hydrophobic residues. Position 5 contains no cardinal binding free energy contributors. Position 3 is dominated by phenylalanine both in CD14 and MD2 binding. Position 8 can be either hydrophobic or contain a positive residue. Position 9 can be negatively charged with glutamic acid or contain glutamine, although it can contain hydrophobic residues as well. Peptides corresponding to substitutions according to the described possibilities, as well as other substitutions that maintain an overall similar total calculated binding energy are considered potential candidates for TLR4 binding peptides.

The data presented in FIGS. 5F-5J suggest the peptide having SEQ ID No. 26, i.e., c[$X_1X_2X_3X_4X_5X_6X_7X_8X_9X_{10}$], with $X_1$=I, L, V, E, K, R, D, N, T, C, A, S, F, Y or G, $X_2$=G, $X_3$=F, M, L, H, K, N, C, Q, T, S, D, R, P, A, E or G, $X_4$=M, C, T, N, A, D, S or G, $X_5$=M, I, Q, L, C, E, A, S or G, $X_6$=M, T, H, S, Q, I, K, F, V, L, W, C, A or G, $X_7$=K, R or M, $X_8$=R, K, E, Q, N, T, D, S, A, I or Y, $X_9$=E, D, M, C, S, T or G and $X_{10}$=F, Y, H, M, T, S or G,—as binding to TLR4 with co-receptor MD2); and the peptide having SEQ ID No. 27, i.e., c[$X_1X_2X_3X_4X_5X_6X_7X_8X_9X_{10}$], with $X_1$=Y, F, M, H, I, R, K, Q, E, V, T, N, A or G, $X_2$=G, $X_3$=F, W, M, H, E, I, Q, V, N, T, L, K, C, D, S, A or G, $X_4$=W, K, H, M, E, I, R, V, Q, L, D, T, C, S, P, W, F, A, Y or G, $X_5$=Q, R, S, T, I, G or M, $X_6$=M, H, R, I, V, K, T, S, C, Q, A, Y or G, $X_7$=H, M, T, Y, Q, C, N, S, A, D, K or G, $X_8$=F, H, W, R, I, M, K, P, V, Q, T, C, N, S, L, A, E or G, $X_9$=L, M, I, Q, H, V, E, T, N, C, D, A, S or G and $X_{10}$=F, H, M, I, L, V, R, T, Q, D, N, K, C, W, S, A, E or G,—as binding to TLR4 with co-receptor CD14.

Any of these combinations may be considered a candidate for a TLR4 binding peptide. It is noted that the specific combinations may be selected with respect to delivery considerations of the peptide to the target tissue, e.g., with respect to the peptide's solubility and biological interactions that may be determined experimentally along the lines exemplified herein for specific peptide examples.

FIGS. 5K-5L show the contributed MD2 binding free energy for each possible amino acid in the first six positions of SEQ ID No. 12. The data presented in FIGS. 5K-5L suggests the peptide having SEQ ID No. 28, i.e., $X_1X_2X_3X_4X_5X_6X_7$, with $X_1$=M, K, H, Q, E, A, C, S, D, or G, $X_2$=W, E, K, D, P, N, R, M, Q, Y, V, I, L or G, $X_3$=W, F, Y, I, M, L, K, V, H, Q, D, E, T, R, P, C, N, A, S or G, $X_4$=M, W, I, H, V, C, F, S, Y or G, $X_5$=K, M, L, R, Q, H, I, N, V, W, Y, C, F or T, $X_6$=I, M, V, T, R, C, K, Q, S, N, A or G and $X_7$=F, I, L, M, H, V, R, T or G. Any of these combinations may be considered a candidate for a TLR4 binding peptide. It is noted that the specific combinations may be selected with respect to delivery considerations of the peptide to the target tissue, e.g., with respect to the peptide's solubility and biological interactions that may be determined experimentally along the lines exemplified herein for specific peptide examples.

The contributed MD2 binding free energy for each possible amino acid in the seven positions of SEQ ID Nos. 19 and 20 suggests the peptide having SEQ ID No 29, i.e. C[$X_1X_2X_3X_4X_5X_6X_7$] with $X_1$=a or G, $X_2$=w or G, $X_3$=w, l, a or G, $X_4$=w, a, or G, $X_5$=r, e, a or G, $X_6$=s, t, a or G and $X_7$=l, h, a or G. All sequences presented in lower case are of D-amino-acids. Any of these combinations may be considered a candidate for a TLR4 binding peptide. It is noted that the specific combinations may be selected with respect to delivery considerations of the peptide to the target tissue, e.g., with respect to the peptide's solubility and biological interactions that may be determined experimentally along the lines exemplified herein for specific peptide examples.

The contributed MD2 binding free energy for each possible amino acid in the seven positions of SEQ ID No. 22, suggests the peptide having SEQ ID No 30, i.e. c[$X_1X_2X_3X_4X_5X_6X_7X_8X_9X_{10}$] with $X_1$=a or G, $X_2$=f, a or G, $X_3$=w, a or G, $X_4$=s, t, c, a, or G, $X_5$=e, q, m, k, l, w, r, I, t, l, h, y, v, a or G, $X_6$=e, q, m, w, y, l, d, a or G, $X_7$=w, e, y, m, q, p, t, d, v, f, c, s, n or G, $X_8$=k, m, l, t, s or G, $X_9$=k, i, p, l, e, v, t, q, e, c, s or G and $X_{10}$=l, m, i, y, k, r, h, v, q, t, c, s, n, or G. All sequences presented in lower case are of D-amino-acids. Any of these combinations may be considered a candidate for a TLR4 binding peptide. It is noted that the specific combinations may be selected with respect to delivery considerations of the peptide to the target tissue, e.g., with respect to the peptide's solubility and biological interactions that may be determined experimentally along the lines exemplified herein for specific peptide examples.

The inventors provide peptides SEQ ID Nos. 23-30 as exemplary generalizations of SEQ ID Nos. 4, 5 and 9 (SEQ ID No. 23); 6 (SEQ ID Nos. 24 and 25); 8 (SEQ ID No. 26 and 27); 12 (SEQ ID No. 28); 19 and 20 (SEQ ID No. 29), and 22 (SEQ ID No. 30), respectively. Similar generalizations for peptides SEQ ID Nos. 1-3, 7, 10, 11 and 13-15 are considered part of the present disclosure as well.

FIGS. 6A-6D present peptide activity using NIH3T3 cells that express TLR4, with either the MD2 co-receptor (top) or CD14 co-receptor (bottom), for peptides of SEQ ID No. 1, 1(M1), 1(M2) and 1(M3), respectively, according to some embodiments of the invention. FIGS. 7A-7X present peptide activity using NIH3T3 cells that express TLR4, with either the MD2 co-receptor (top) or CD14 co-receptor (bottom), for peptides of SEQ ID Nos. 2-22, according to some embodiments of the invention. FIGS. 6A-6D and 7A-7X show the dose response inhibitor/activator effects of the designed peptides using a reporter gene assay. The reporter gene assay is composed of NIH3T3 cells transfected with either MD2 or CD14 along with TLR4 and the NF-κB-inducible reporter gene Secreted Alkaline Phosphatase (SEAP) to monitor TLR4 activation (Burger-Kentischer et al. 2010, A new cell-based innate immune receptor assay for the examination of receptor activity, ligand specificity, signaling pathways and the detection of pyrogens. *J Immunol*

*Methods.* 358(1-2): 93-103). The reporter gene is inactive when exposed to medium devoid of TLR4 activators (e.g., LPS) and responds with colorimetric signal upon activation. The receptors are coupled to for the detection of inhibitory activity, cells were treated with the peptide prior to exposure to LPS and the response to LPS is measured at variable peptide doses (as labeled). The detection of cell activation was performed using the peptide alone, at variable doses, as indicated in the respective graphs.

The following presents in more details the experimental procedures. Experimental setup: The cell-based Assay is performed with different NIH3T3 reporter cell lines (NIH 3T3 PRR SEAP-TLR4/CD14 or -TLR4/MD2) and the control cell line NIH 3T3 SEAP. The NIH3T3 SEAP cell line is used in order to determine the background of the alkaline phosphatase expression. It is a cell line stably transfected with only the reporter gene plasmid. For each assay a vial of the master cell bank is revitalized and seeded in a standard cell culture flask (75 cm$^2$ T-Flask) at day one. Cells are cultured in 20 ml culture media (DMEM supplemented with 10% FCS (heat inactivated), 50 units/ml penicillin, 0.05 mg/ml streptomycin and 2 mmol/L L-glutamine). The cells are cultured at 37° C. in a 5% $CO_2$ humidified atmosphere.

At Day 1: For the PAMP Assay cells are seeded in a 96-well plate at a density of 0.3·10$^5$ cells/well in a final volume of 100 μl culture media (DMEM, 10% FCS (heat inactivated)). To ensure equal culture conditions the 96-well cell culture plates are placed side by side and cultivated in a humidified $CO_2$ incubator (37° C. and 5% $CO_2$).

At Day 2: After a cultivation period of 24 h the media is removed and replaced with the respective volume of fresh media (DMEM, 0.5% FCS (heat inactivated)). The lyophilized peptides are stored in a freezer at −20° C. upon arrival. For the experiments they are dissolved in DMSO (to the highest possible concentration). Before opening the peptides are allowed to equilibrate to room temperature (in order to reduce the uptake of moisture). For each experiment the stock solution is diluted in DMEM to the appropriate working concentration. The peptides are diluted in such a way that the final DMSO concentration does not exceed 0.1%. Sonication was also used to help dissolve the peptides. Immediately after replacing the media, the diluted peptides are applied in a serial dilution to the cells and directly after that the agonist is added to the cells. After adding peptide and antagonist the final volume in each well of a 96 well plate amounts 100 μl/well. The culture medium containing 0.5% FCS is used as a negative reference item. The induction is performed for 18 h at 37° C. and 5% $CO_2$.

At Day 3: To determine the final SEAP value, 50 μl of the supernatant is carefully transferred in a new 96-well plate (Greiner-F-plate) and 50 μl of the substrate (pNPP; p-nitrophenyl phosphate) is added. SEAP catalyzes the hydrolysis of pNPP to the final product para-nitrophenol (yellow) which can be detected by a photometric analysis using an UV-VIS reader at 405 nm. The measurements are usually performed at t=0 min, 5 min, 10 min, 15 min, 20 min, 30 min, 40 min, 50 min and 60 min.

The results of FIGS. 6A-6D and 7A-7X with respect to peptide activity are summarized in Table 1 above with respect to the type of effect of the respective peptide (activation/inhibition) and with respect to the corresponding co-receptor (MD2/CD14). Data concerning SEQ ID No. 22 with respect to co-receptor CD14 is in preparation.

Figure 7A:
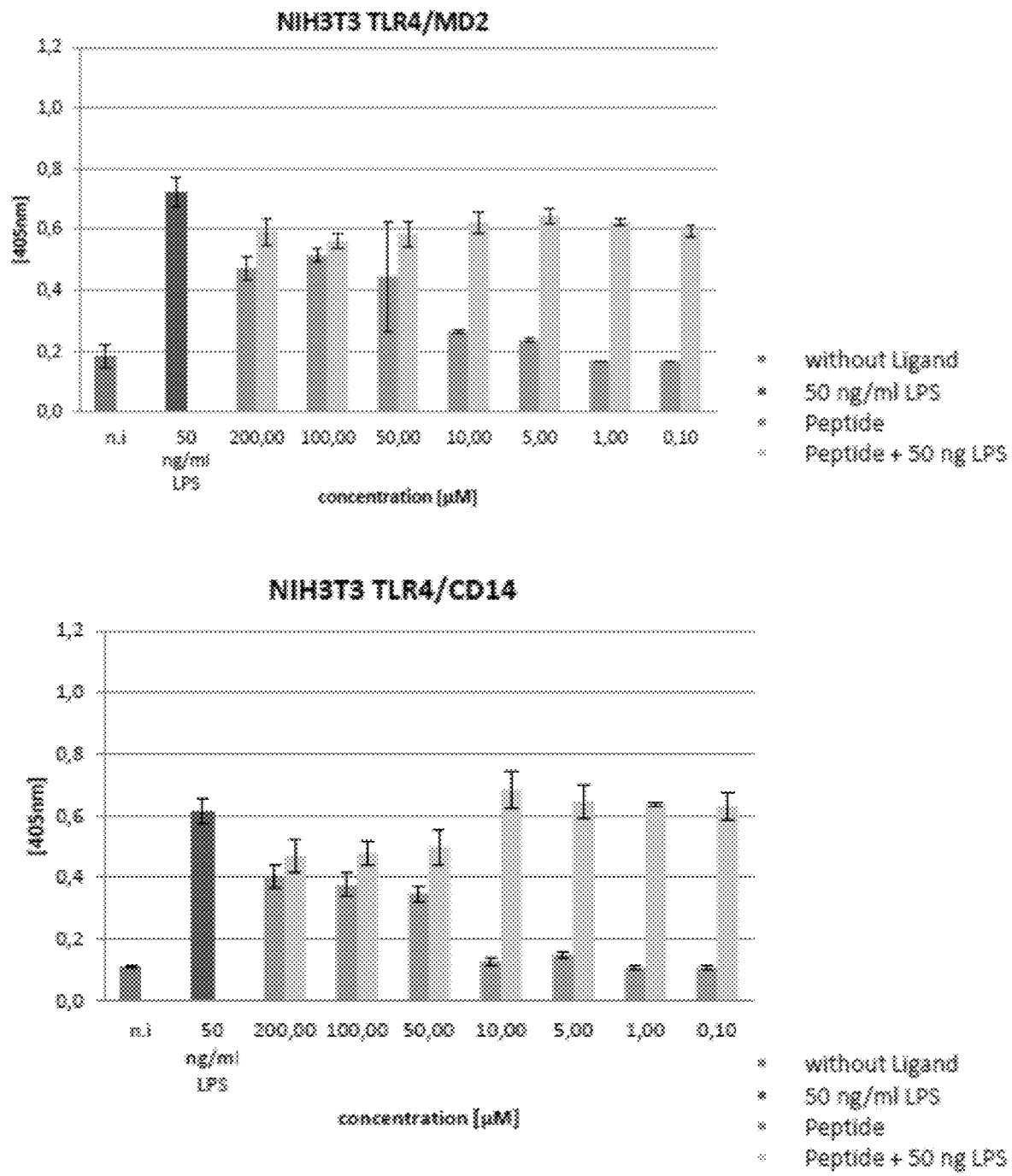
FIGS. 7A-7X present peptide activity using NIH3T3 cells that express TLR4, with either the MD2 co-receptor (top) or CD14 co-receptor (bottom), for peptides of SEQ ID Nos. 2-22, according to some embodiments of the invention.
Figure 7B:
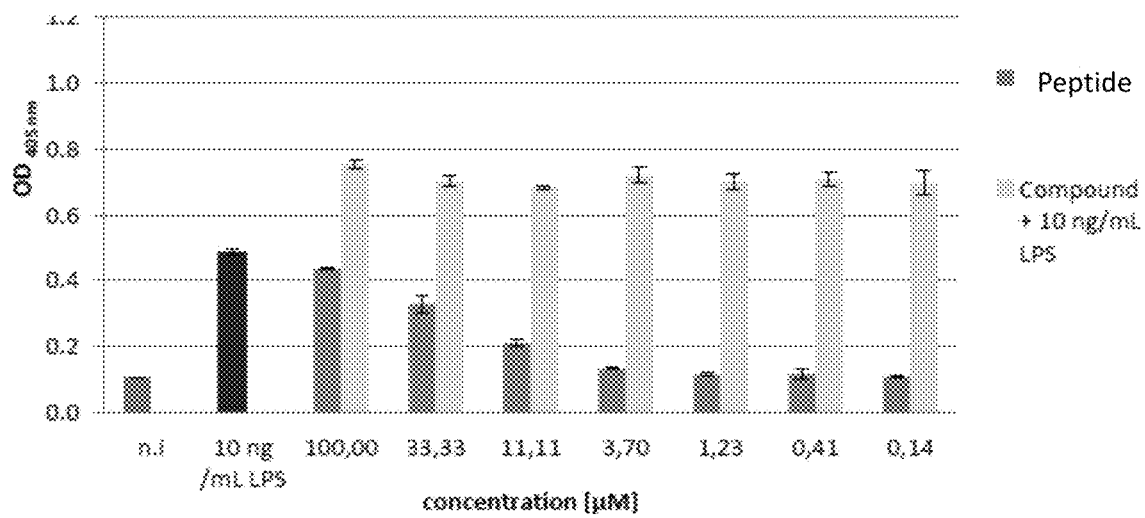
Figure 7B:
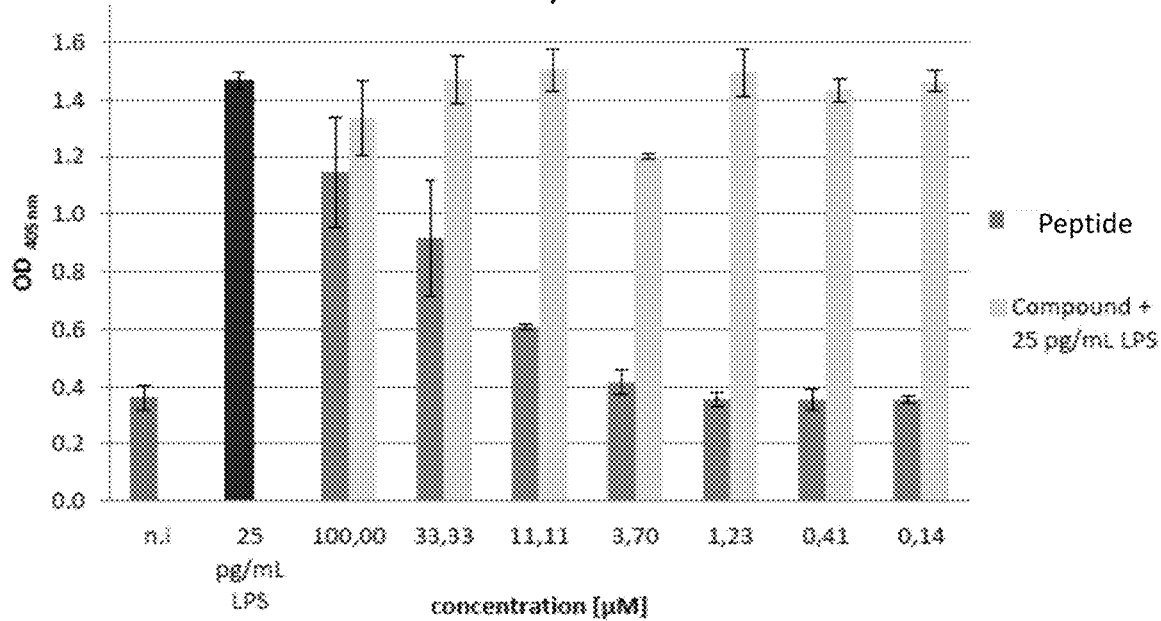
Figure 7C:
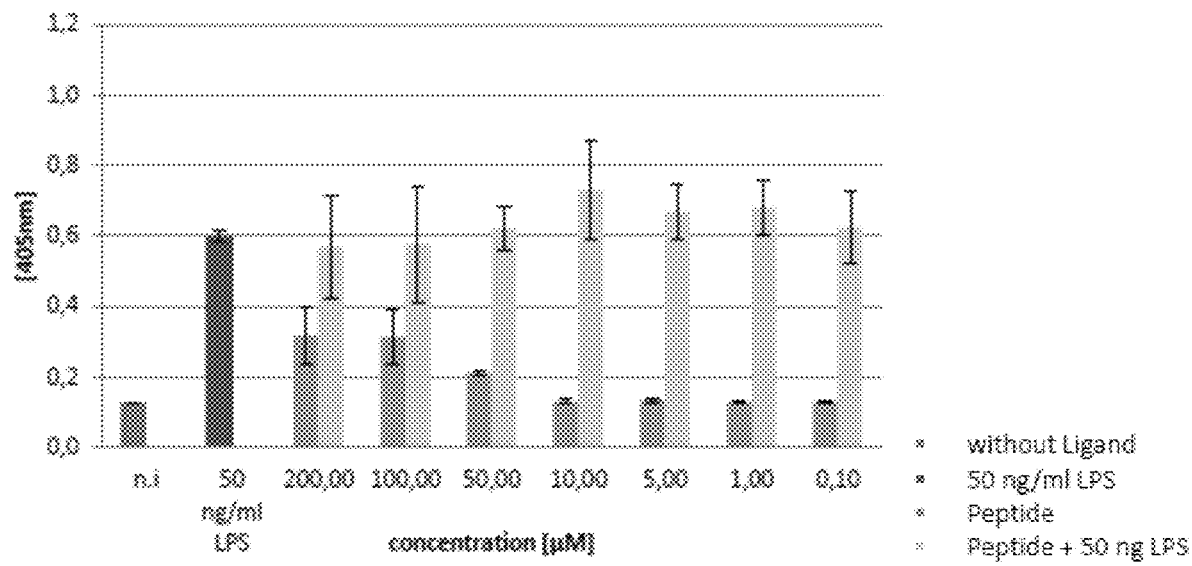
Figure 7C:
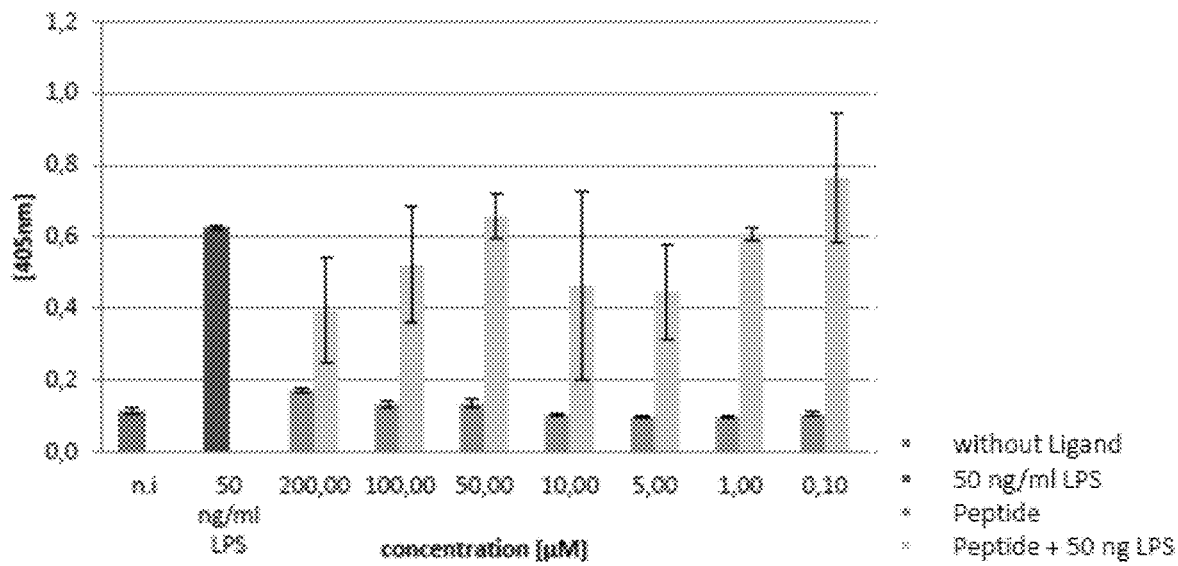
Figure 7D:
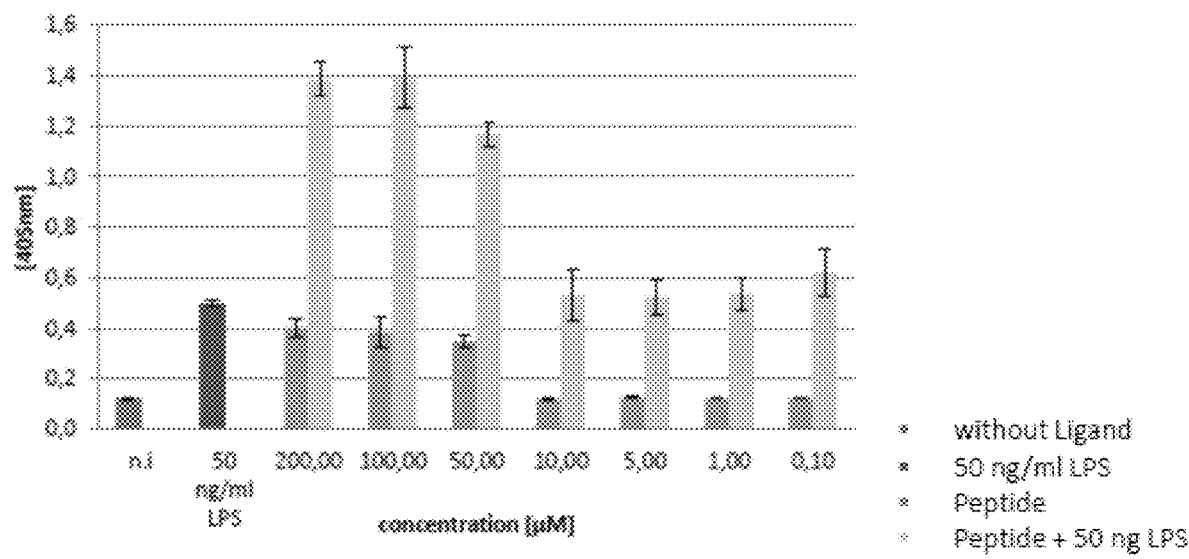
Figure 7D:
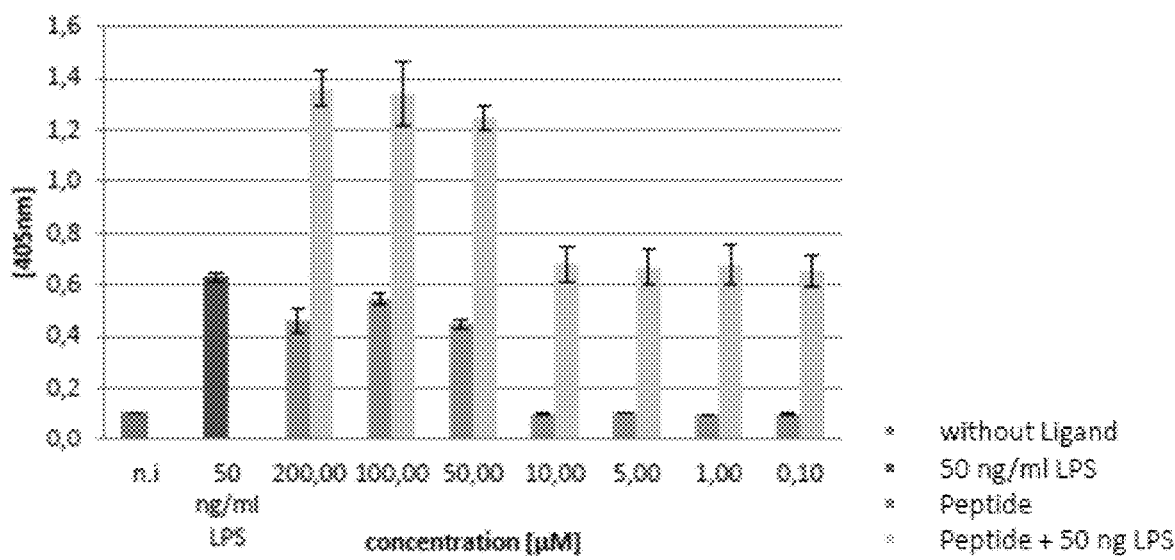
Figure 7E:
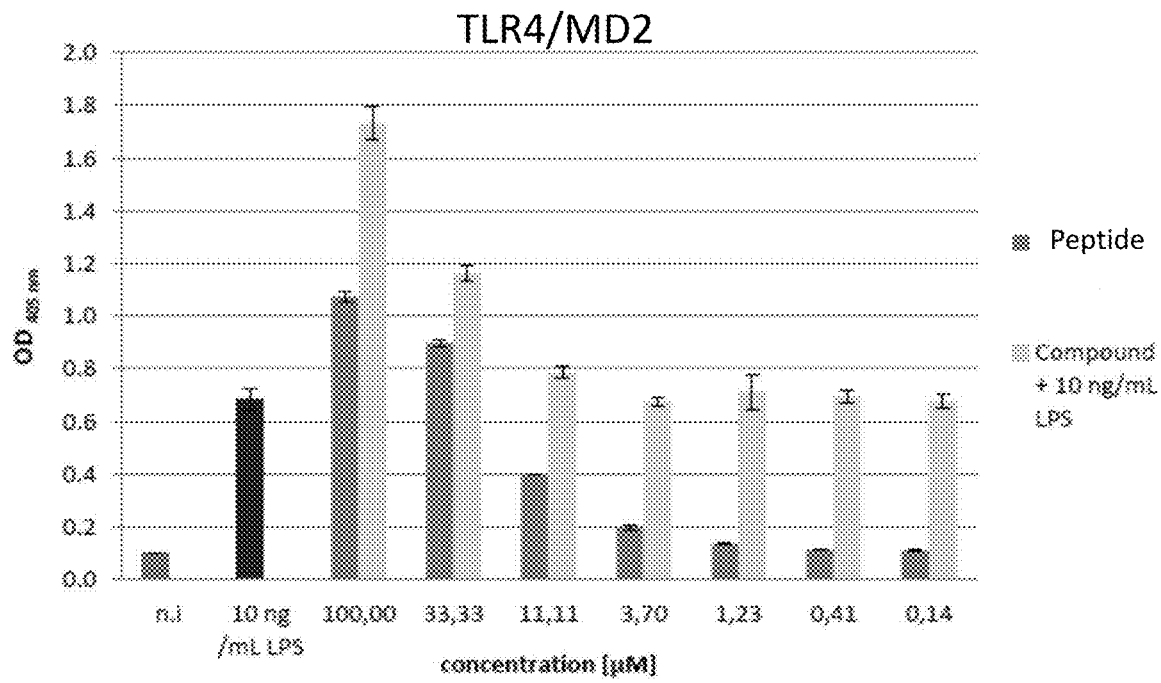
Figure 7E:
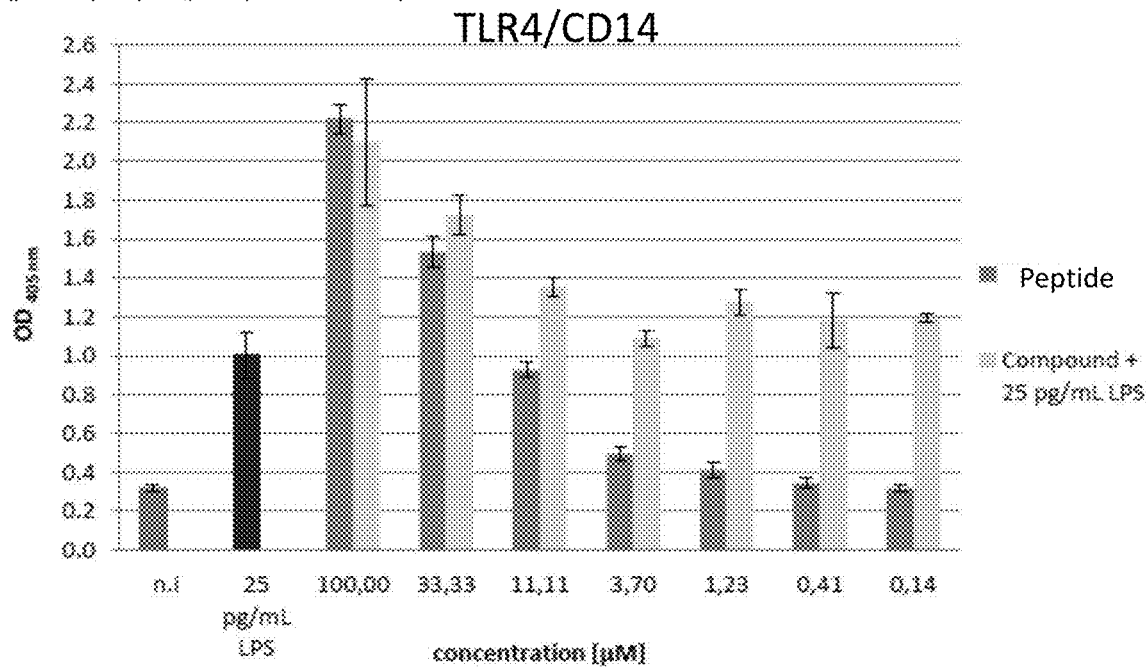
Figure 7F:
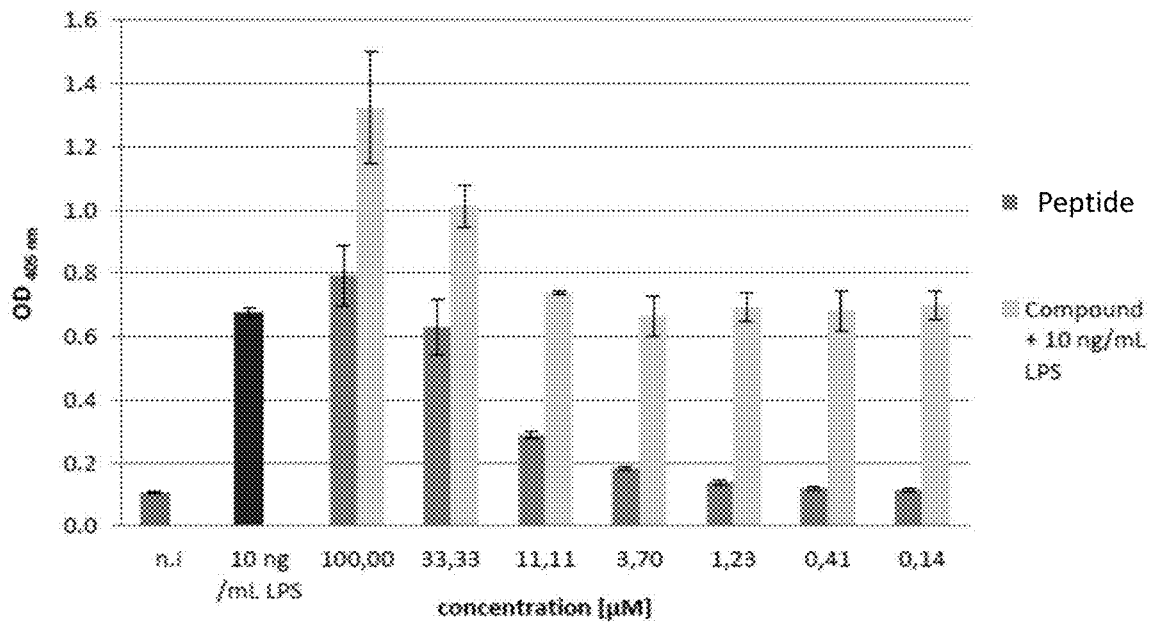
Figure 7F:
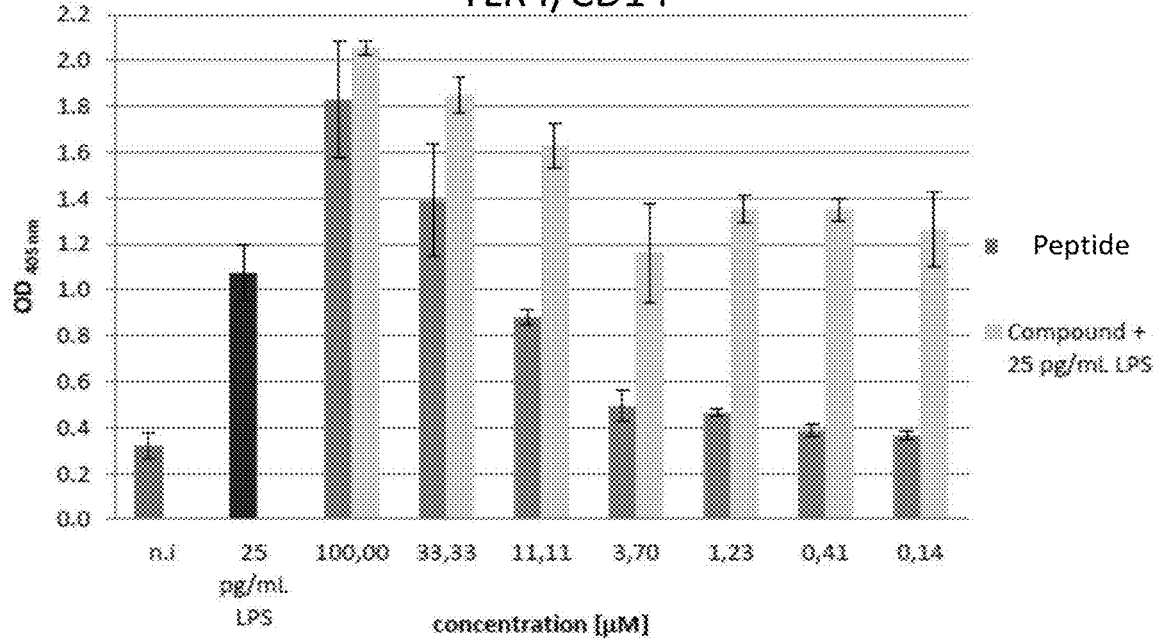
Figure 7G:
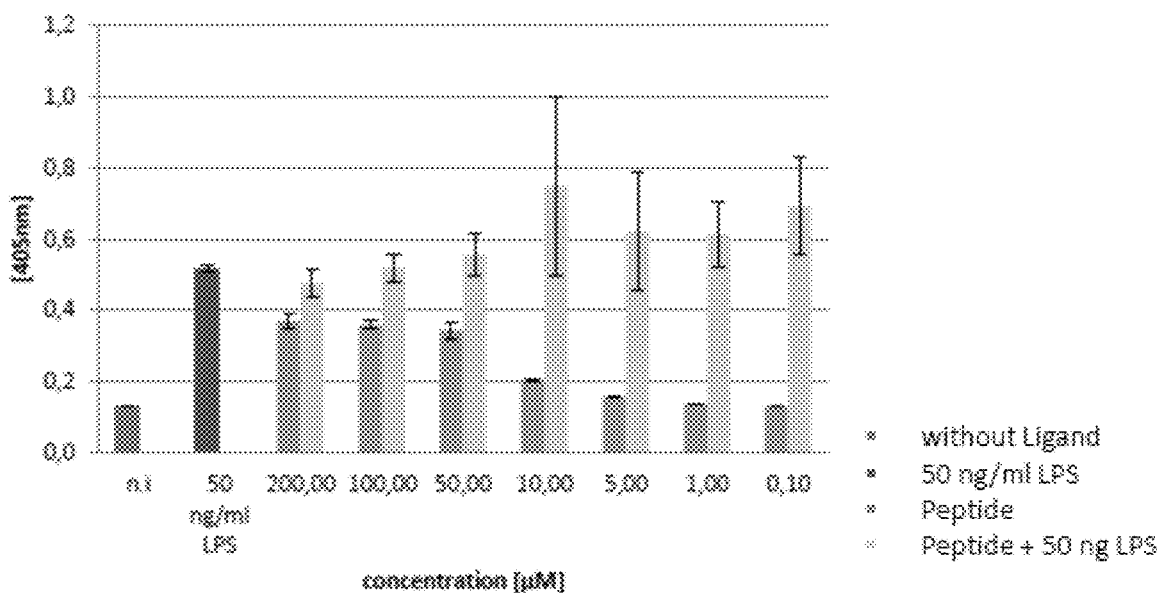
Figure 7G:
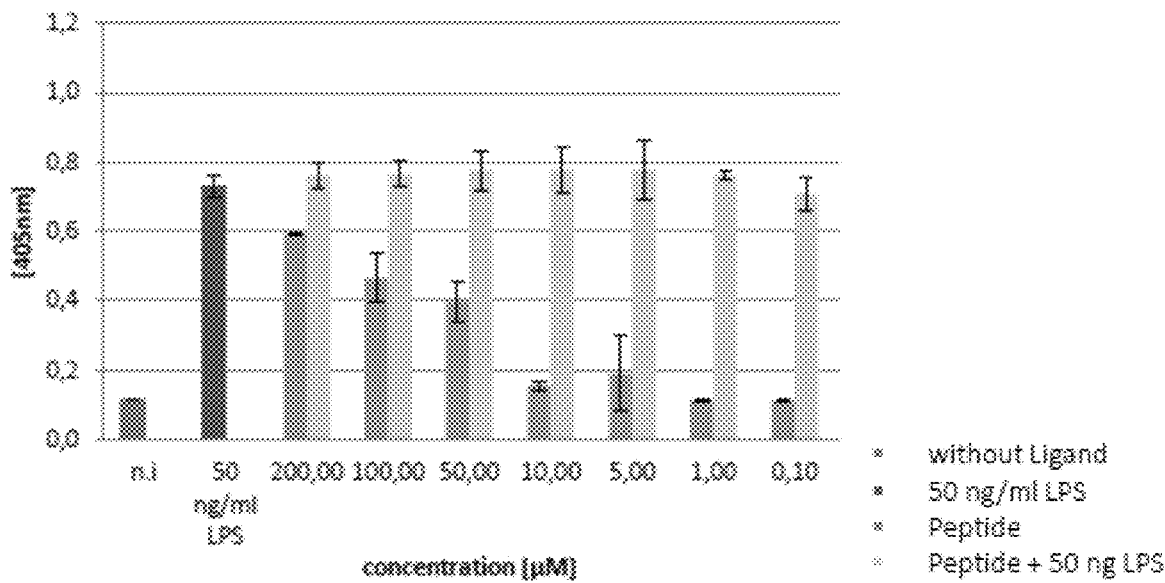
Figure 7H:
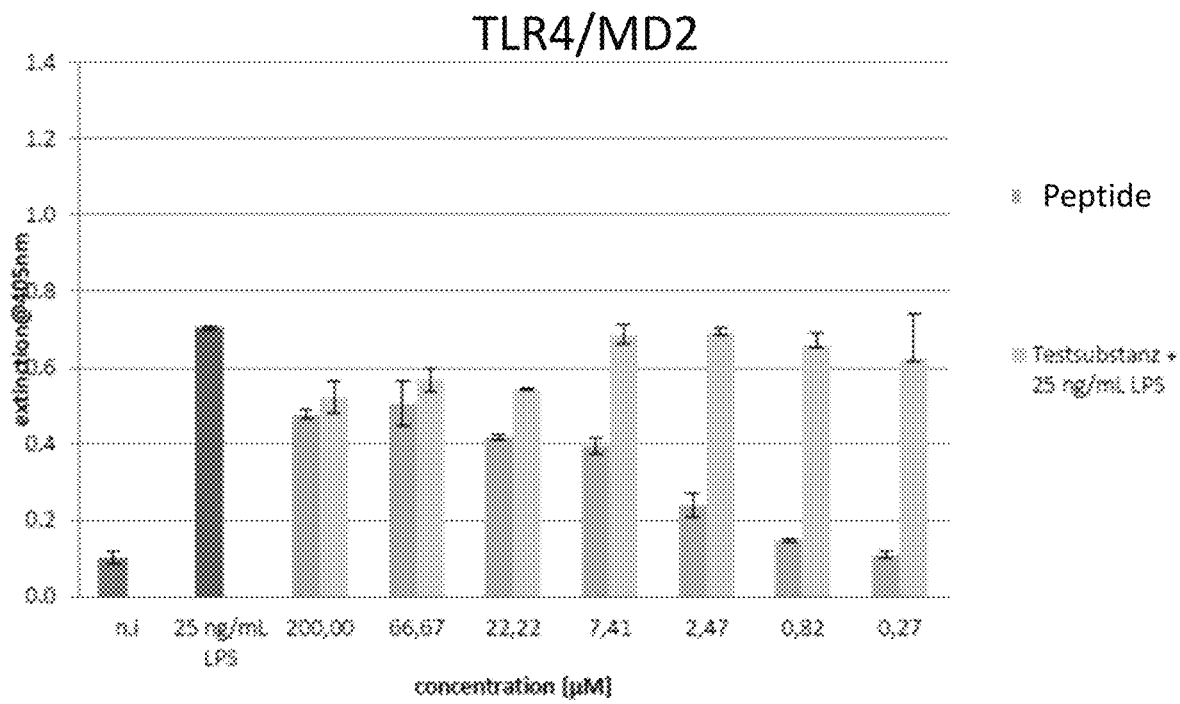
Figure 7H:
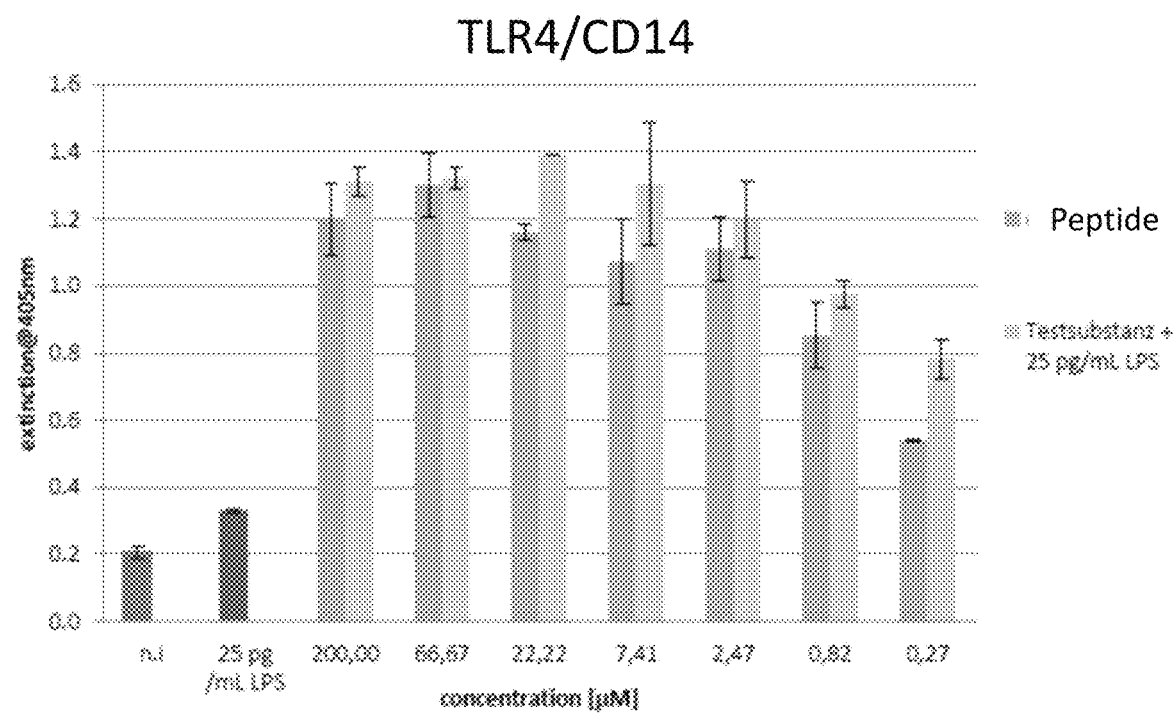
Figure 7I:
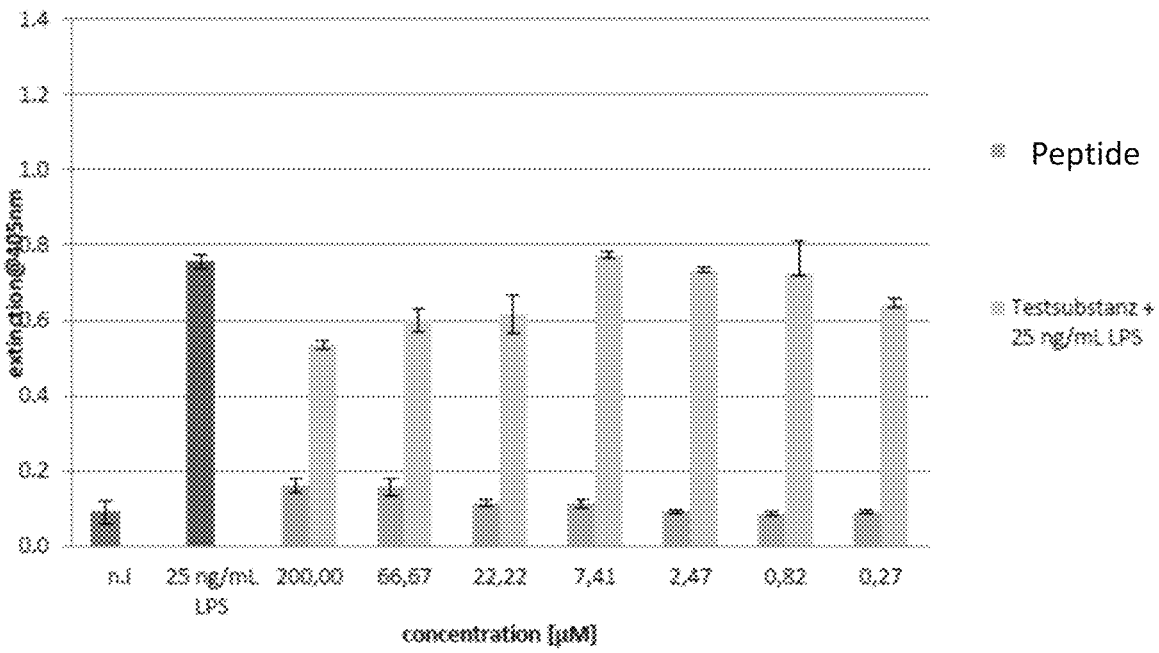
Figure 7I:
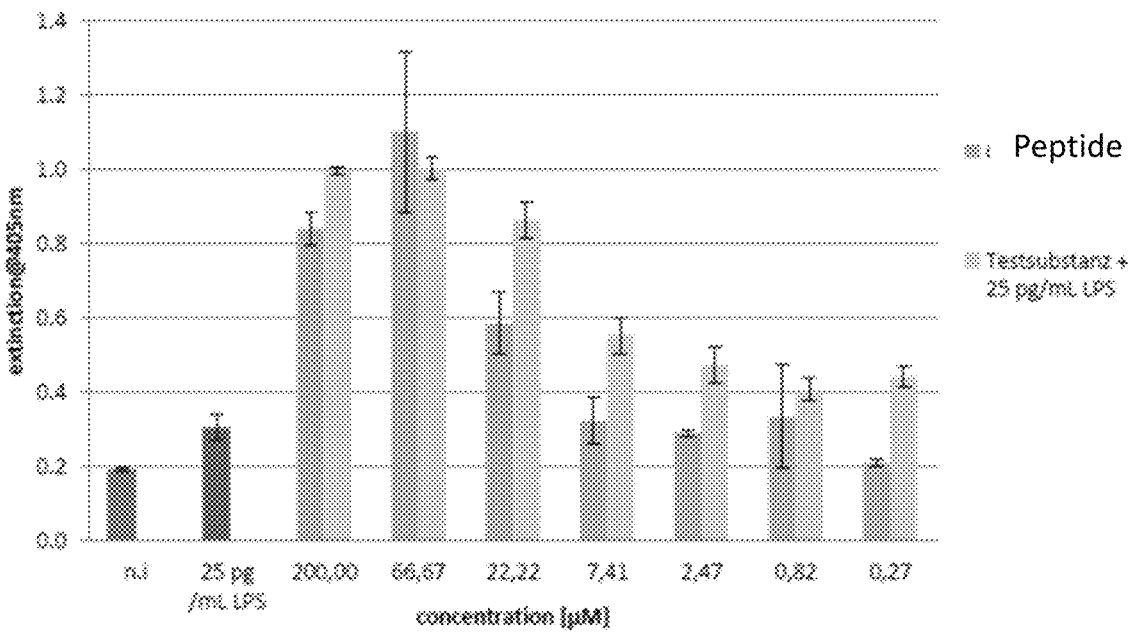
Figure 7J:
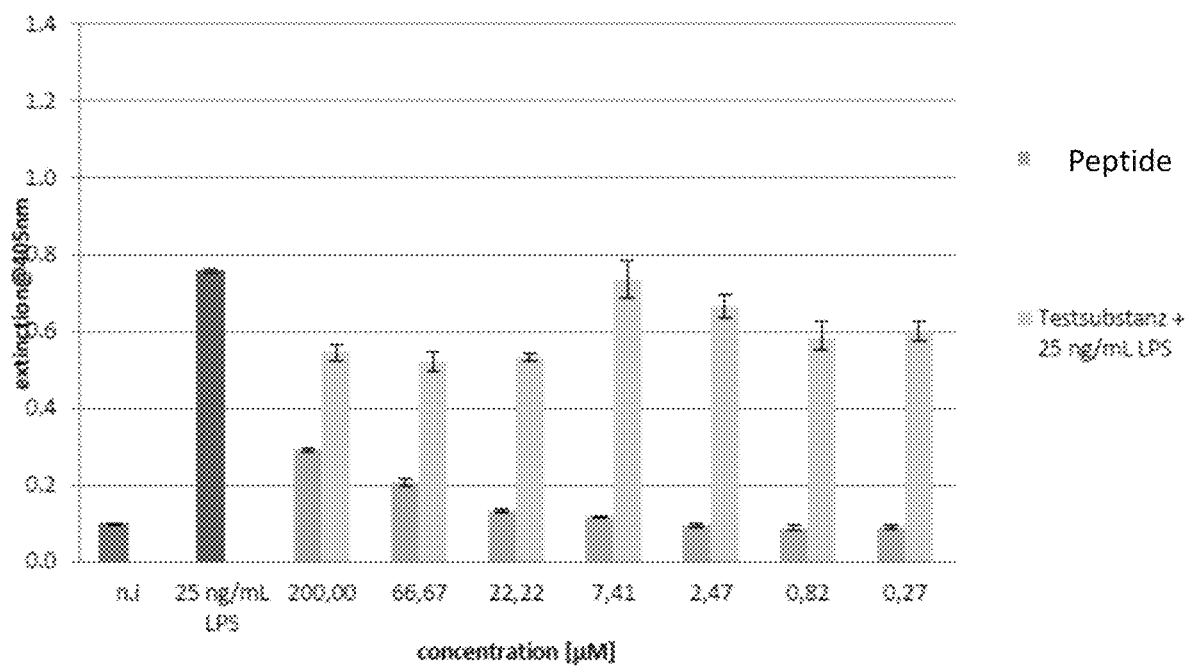
Figure 7J:
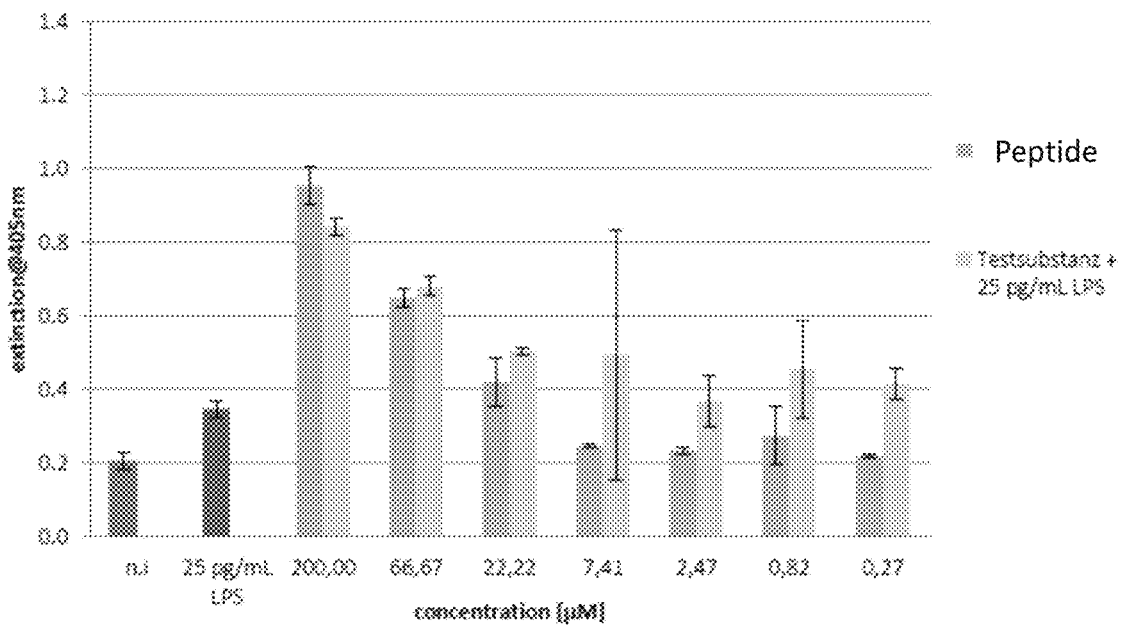
Figure 7K:
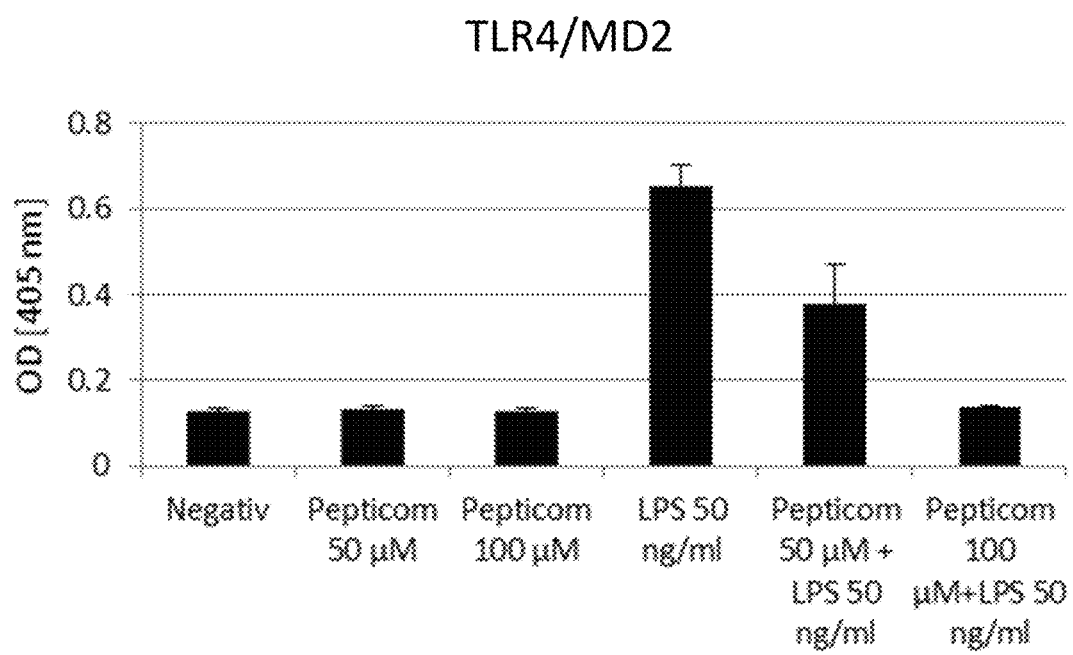
Figure 7K:
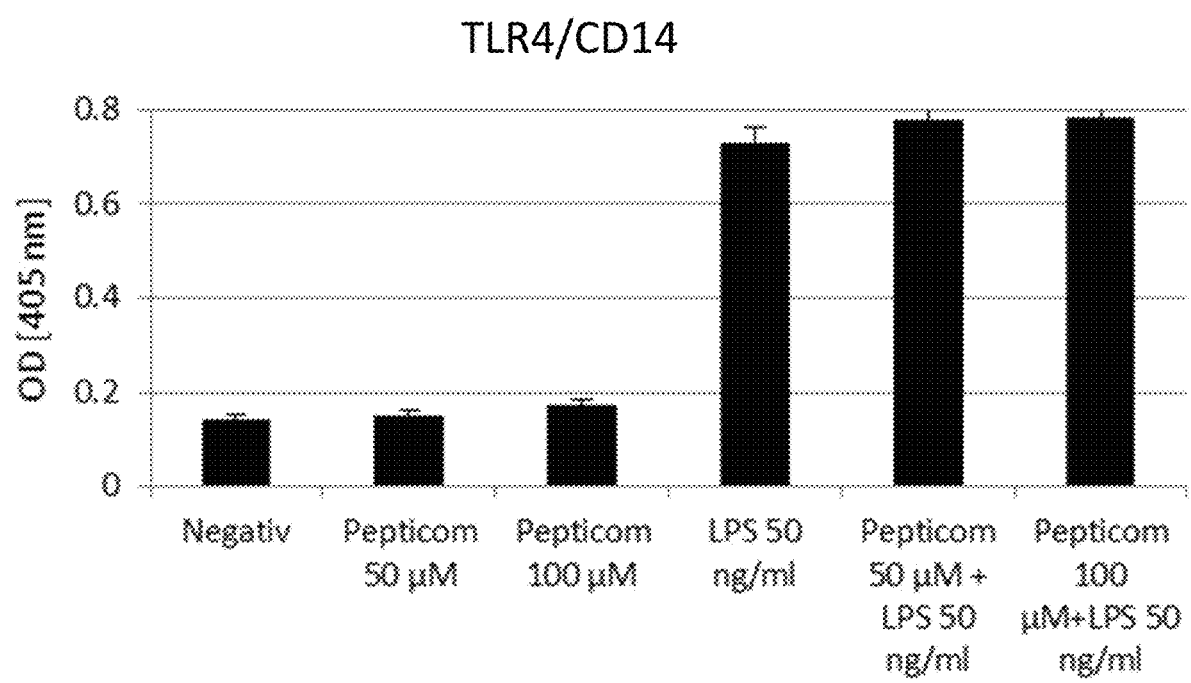
Figure 7L:
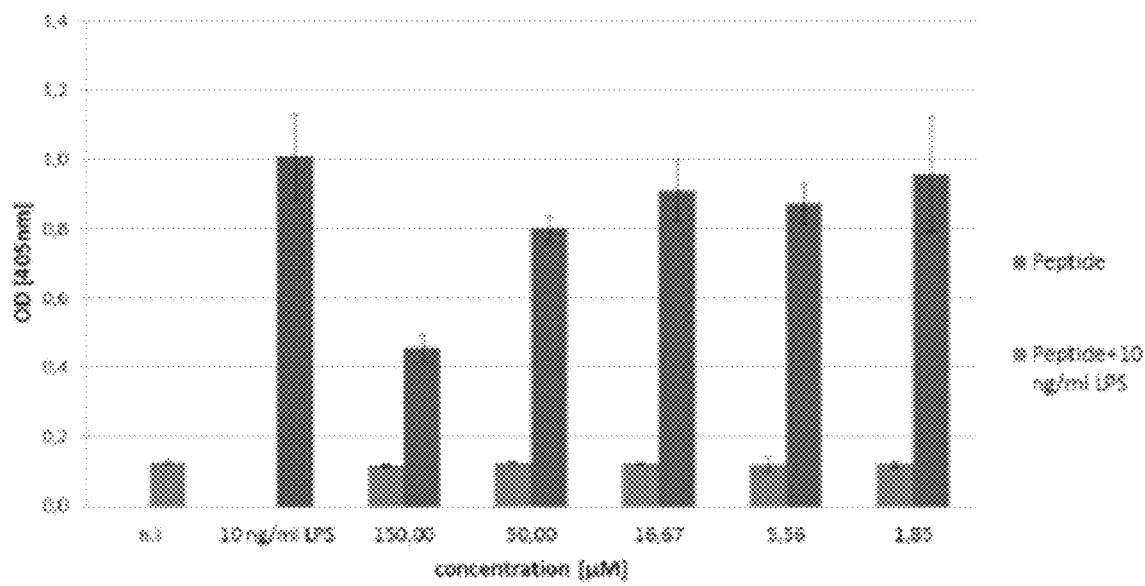
Figure 7L:
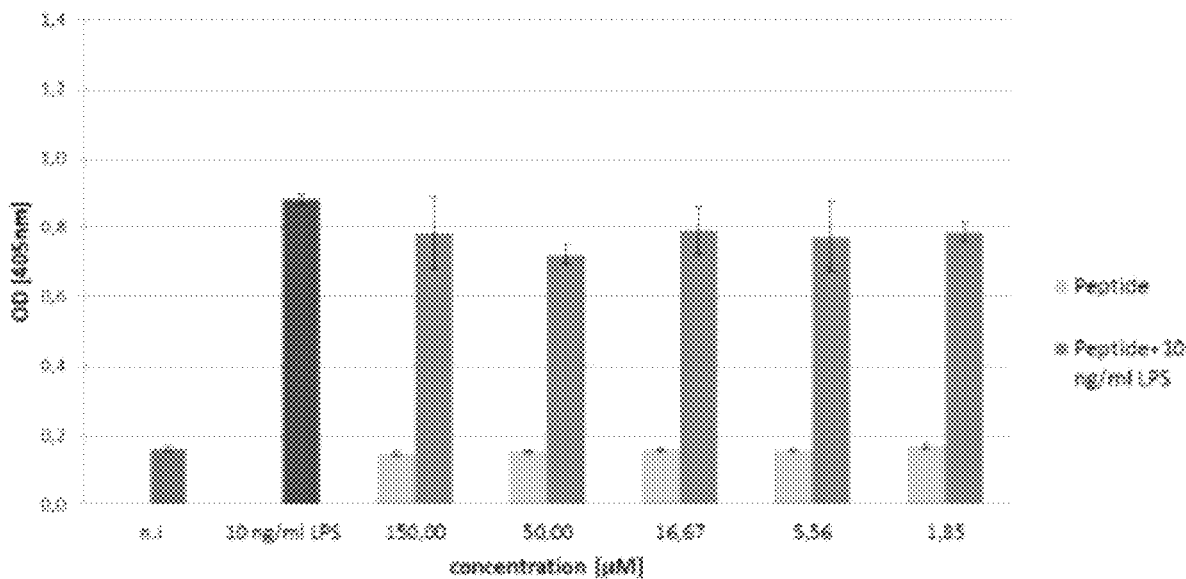
Figure 7M:
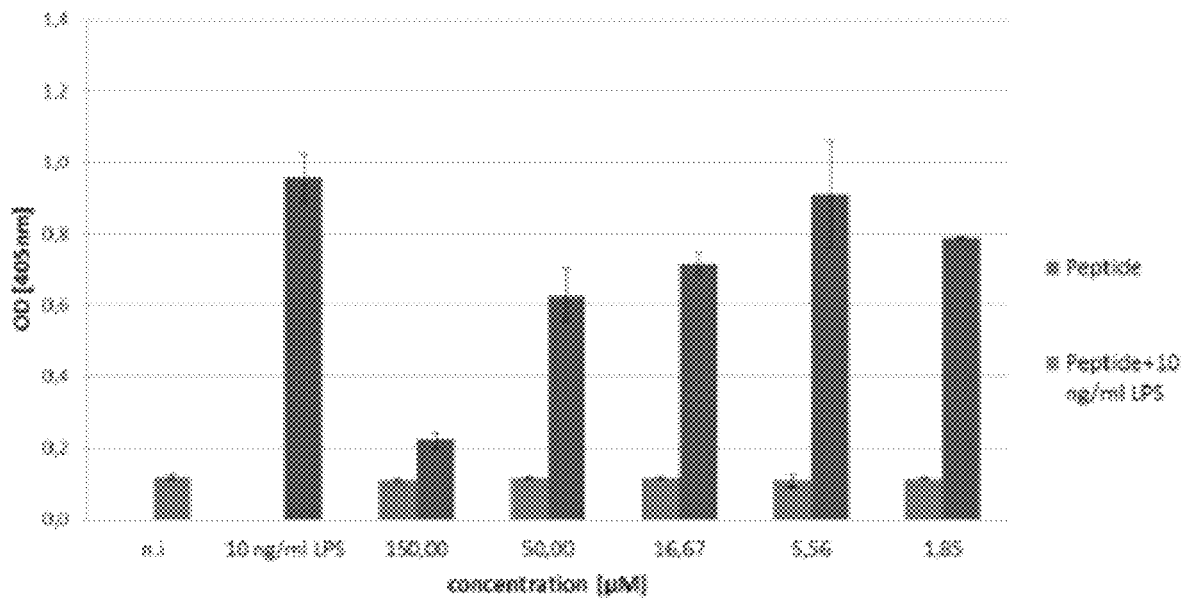
Figure 7M:
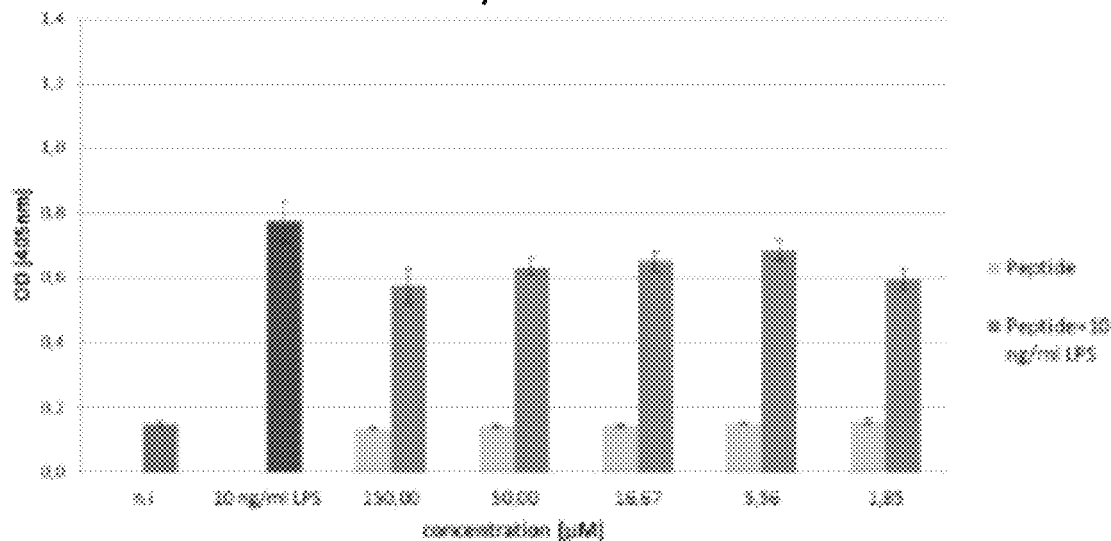
Figure 7N:
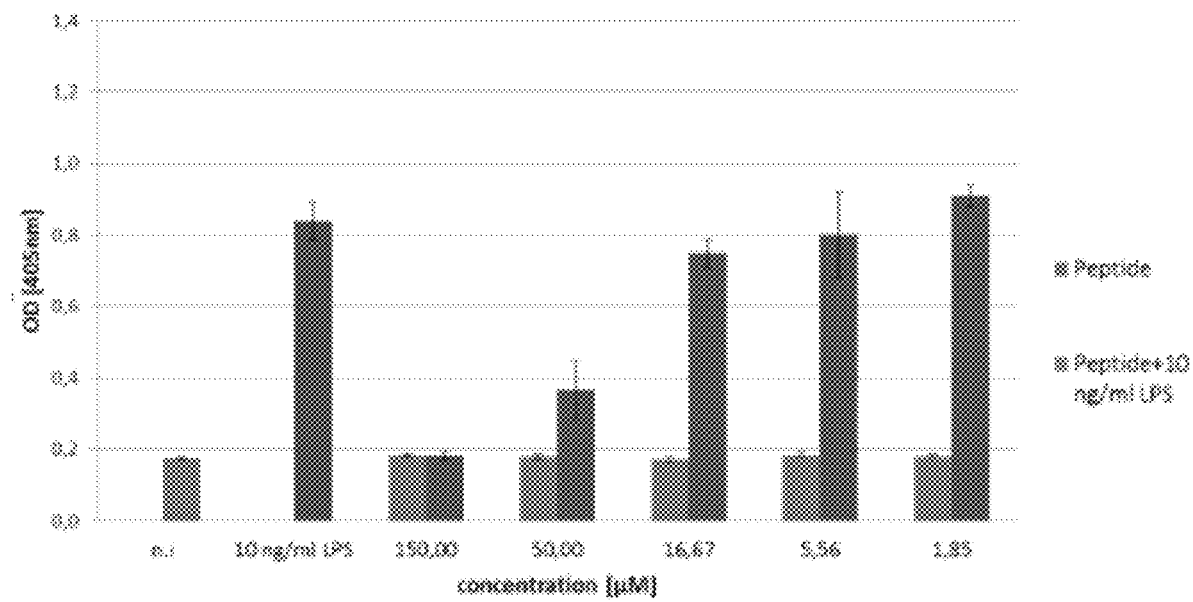
Figure 7N:
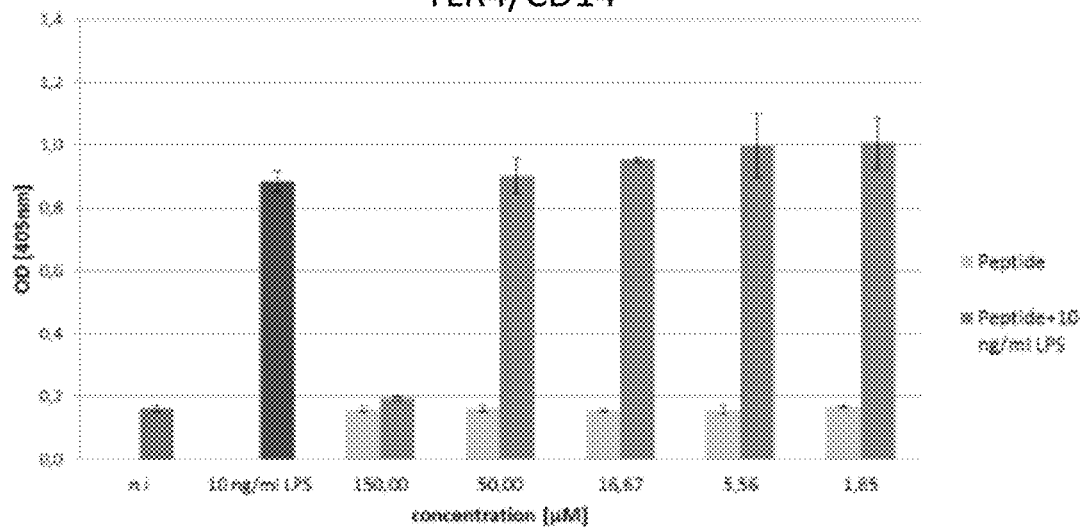
Figure 7O:
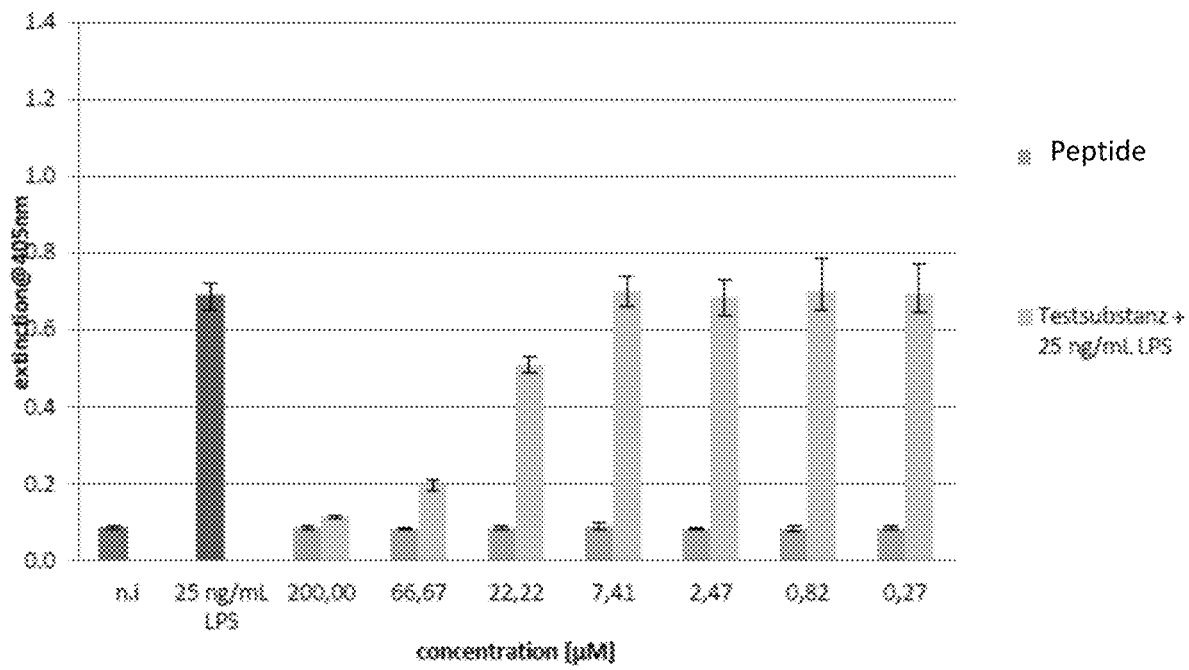
Figure 7O:
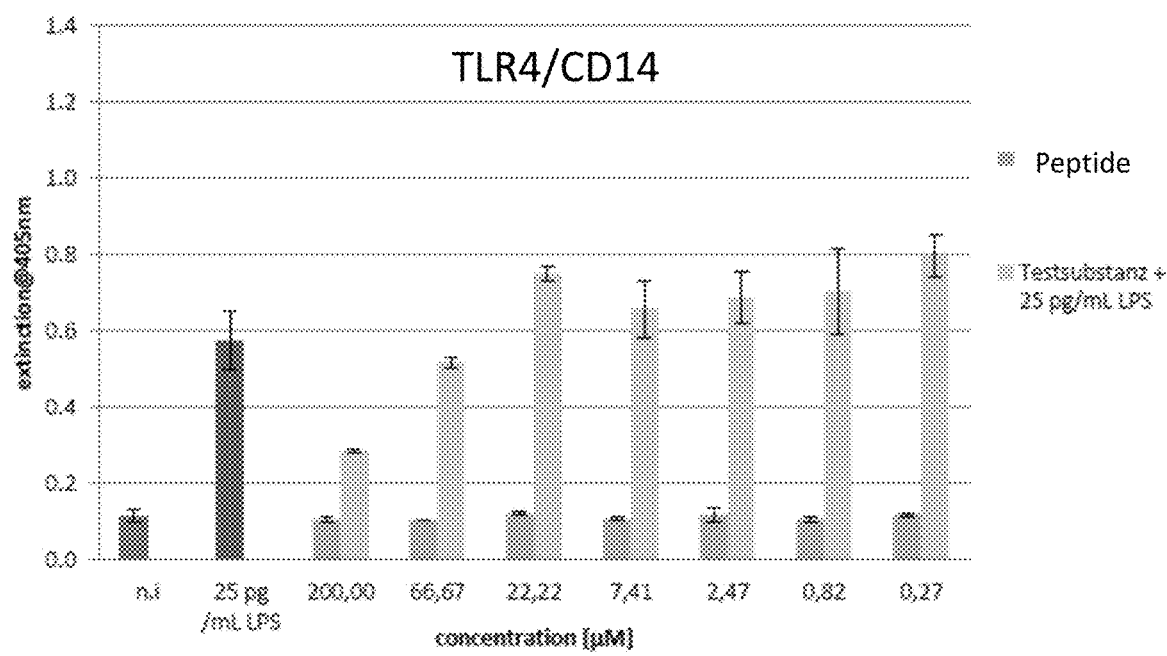
Figure 7P:
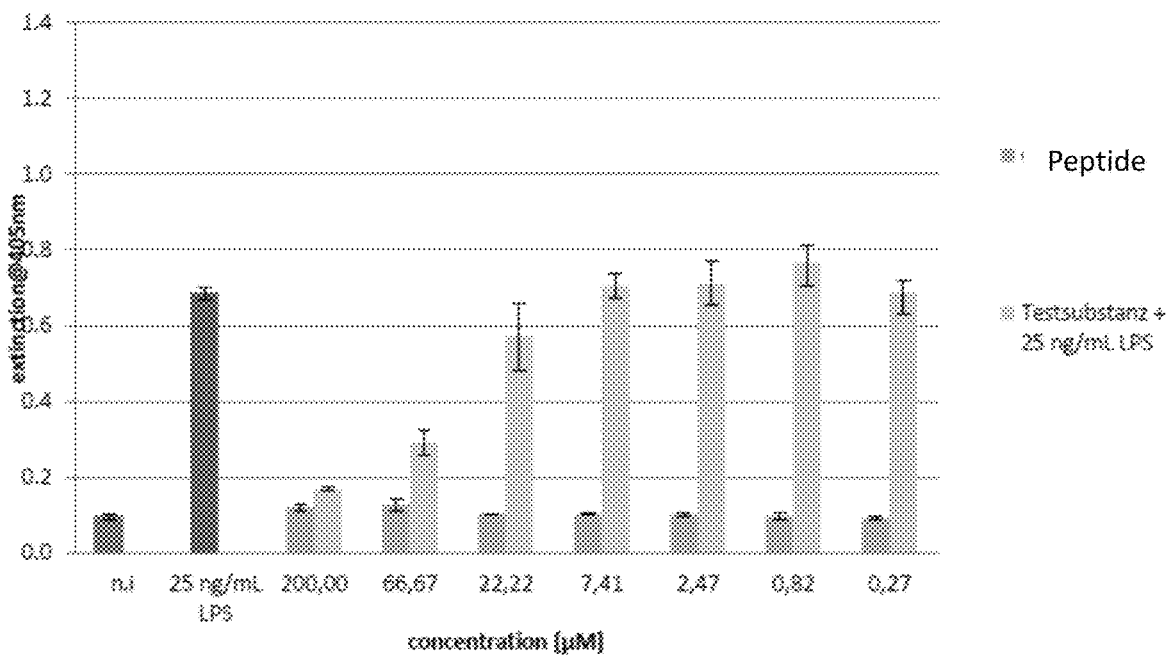
Figure 7P:
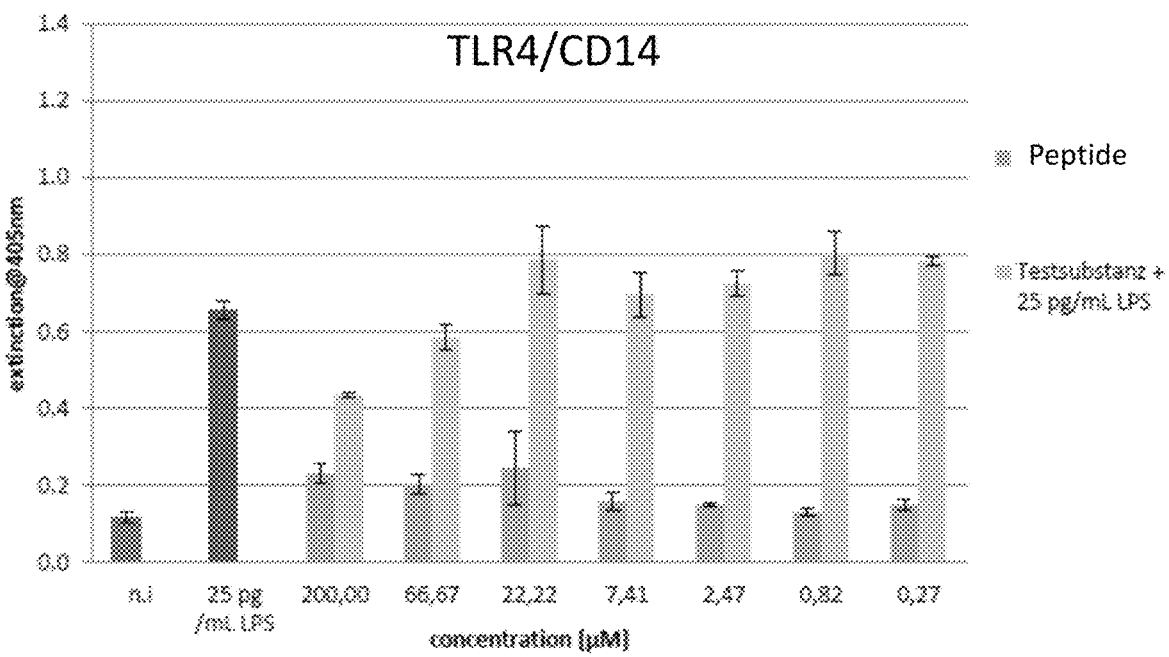
Figure 7Q:
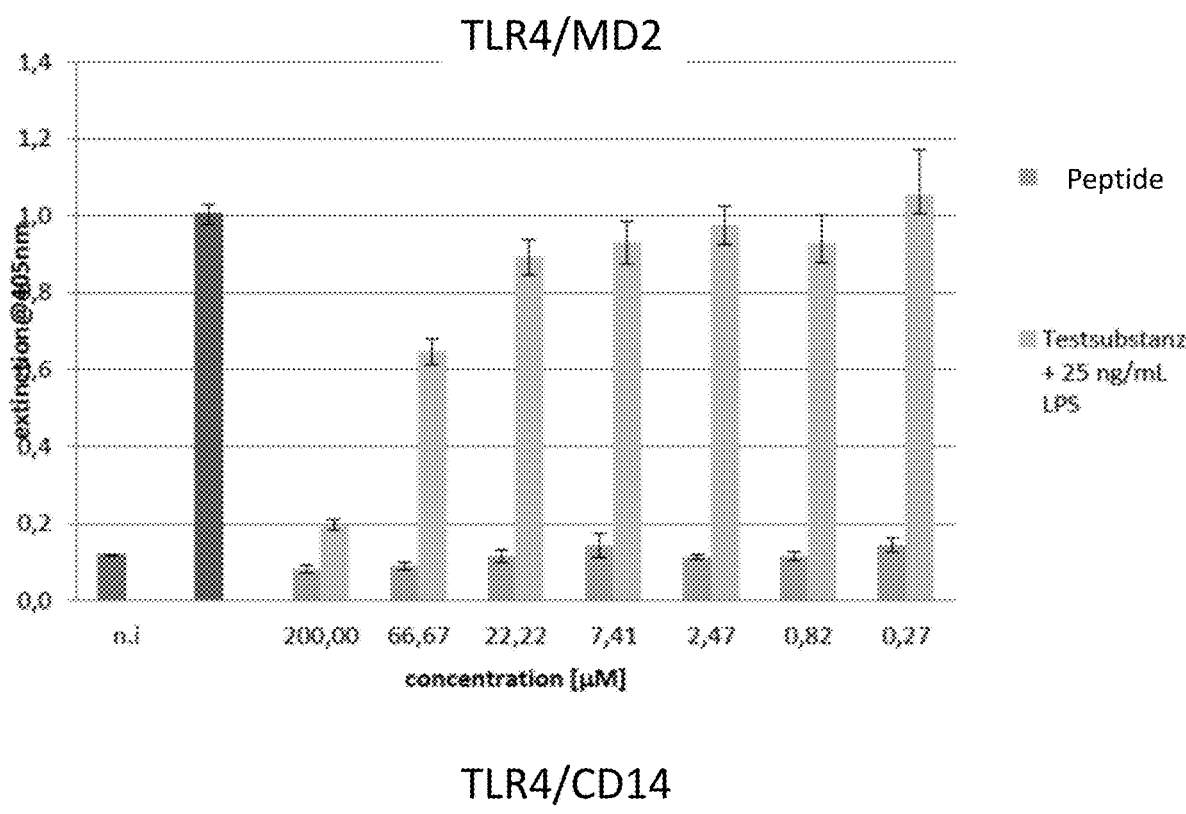
Figure 7R:
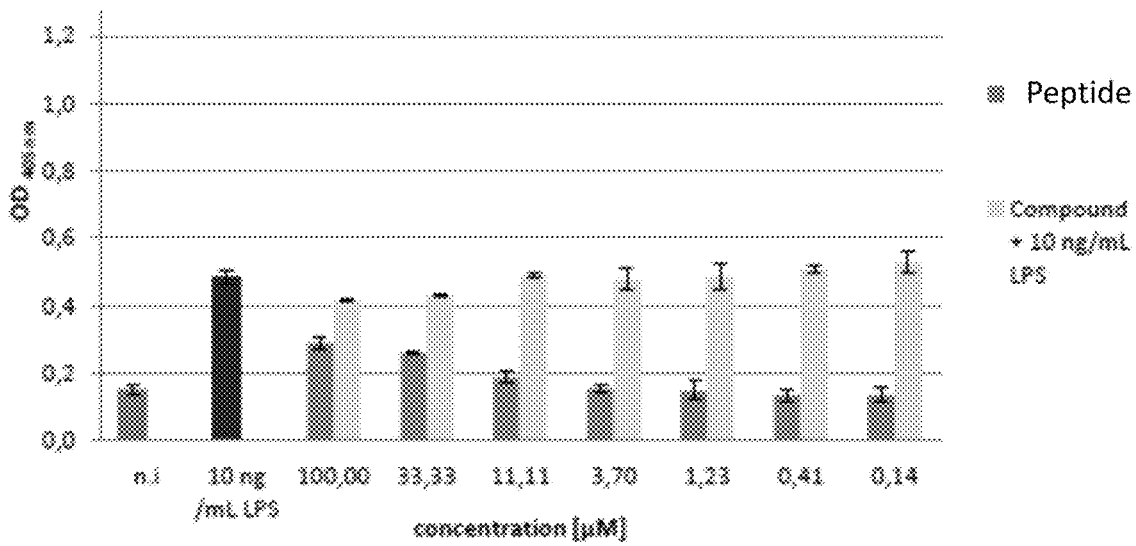
Figure 7R:
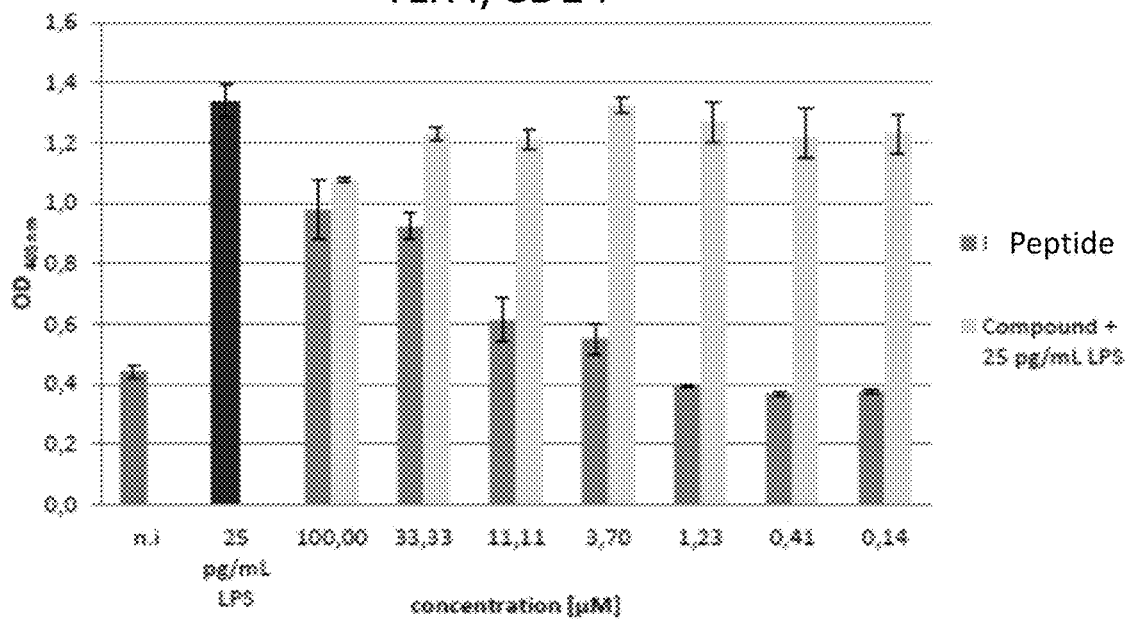
Figure 7S:
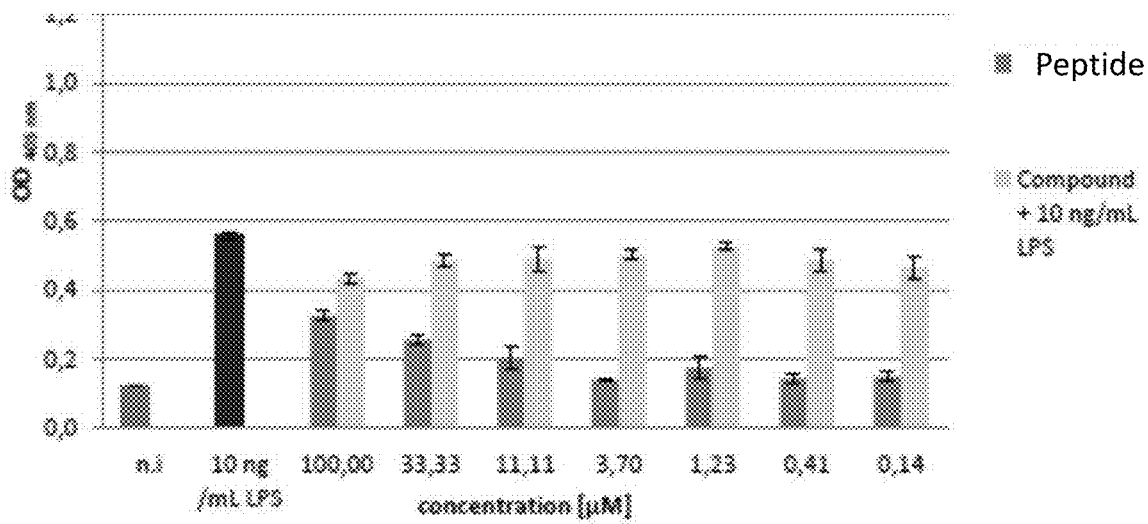
Figure 7S:
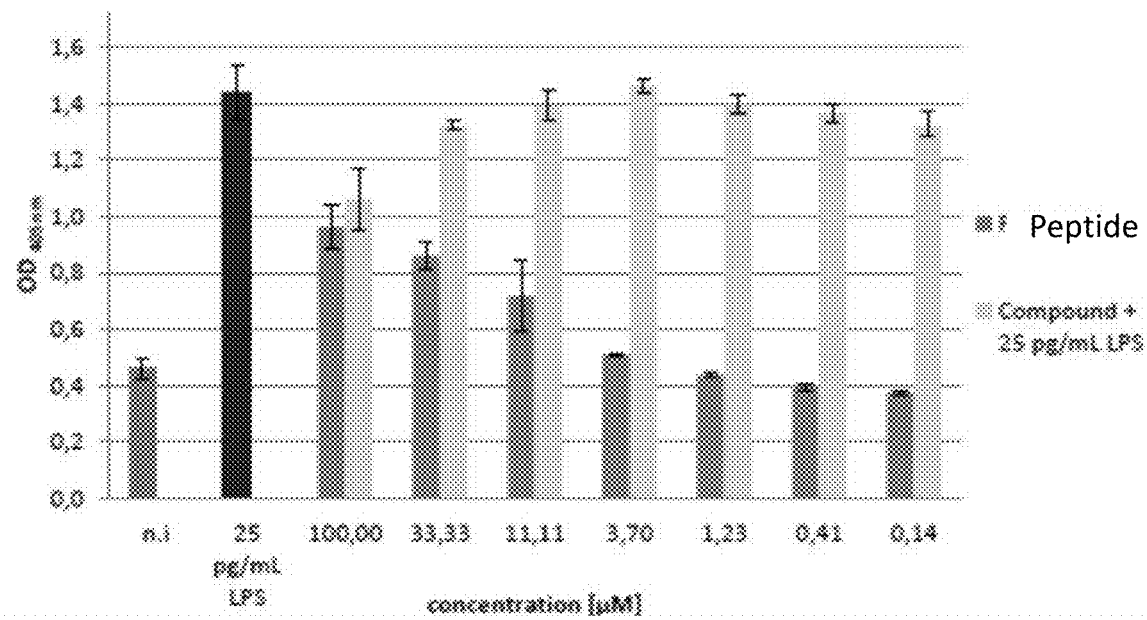
Figure 7T:
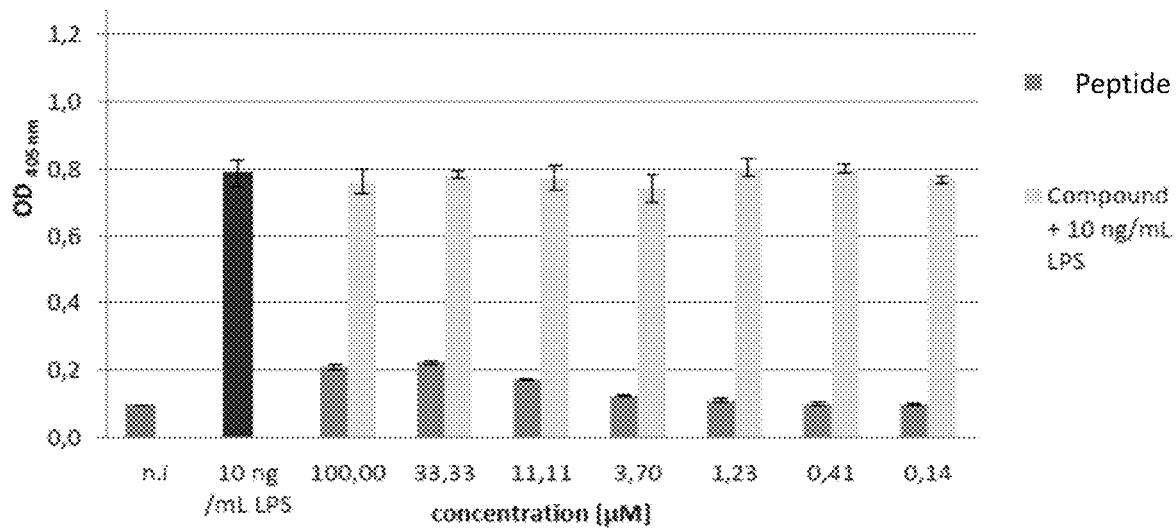
Figure 7T:
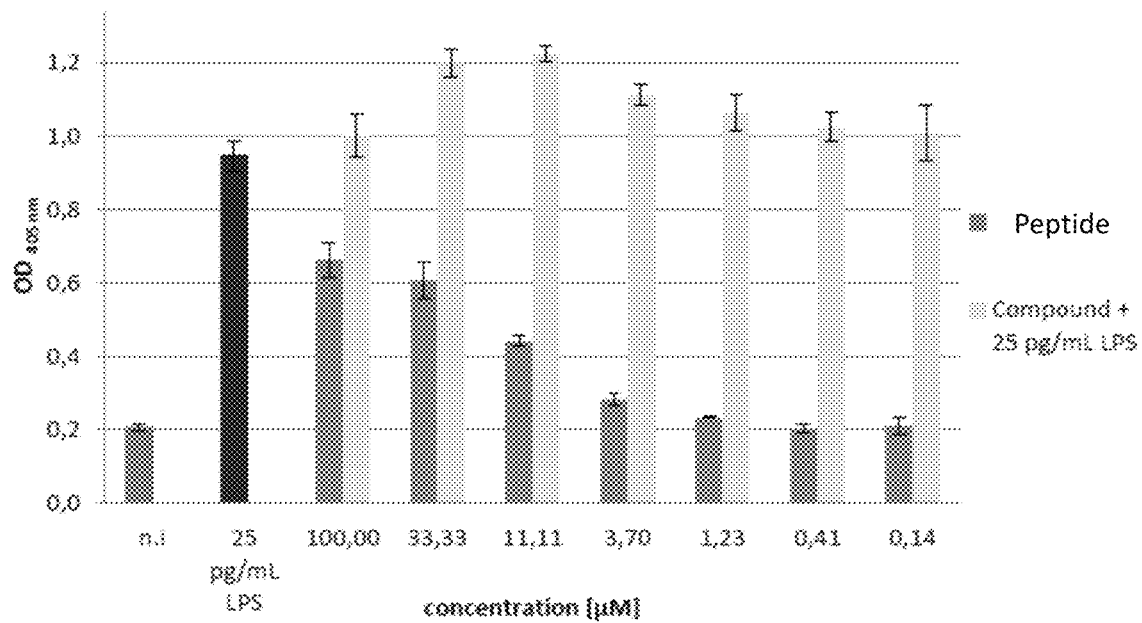
Figure 7U:
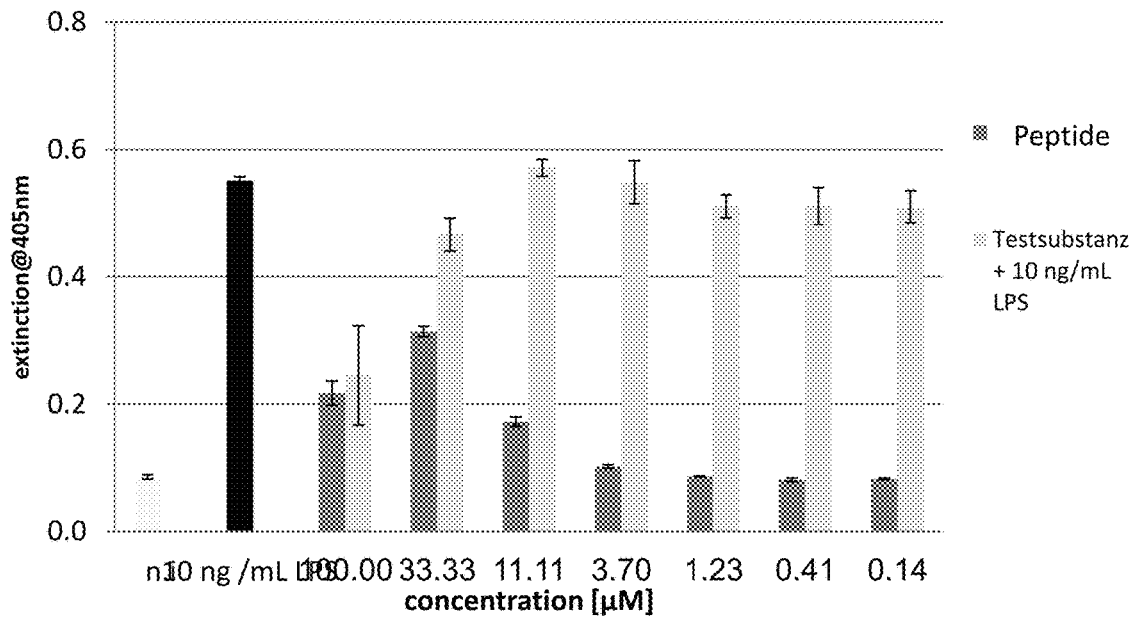
Figure 7U:
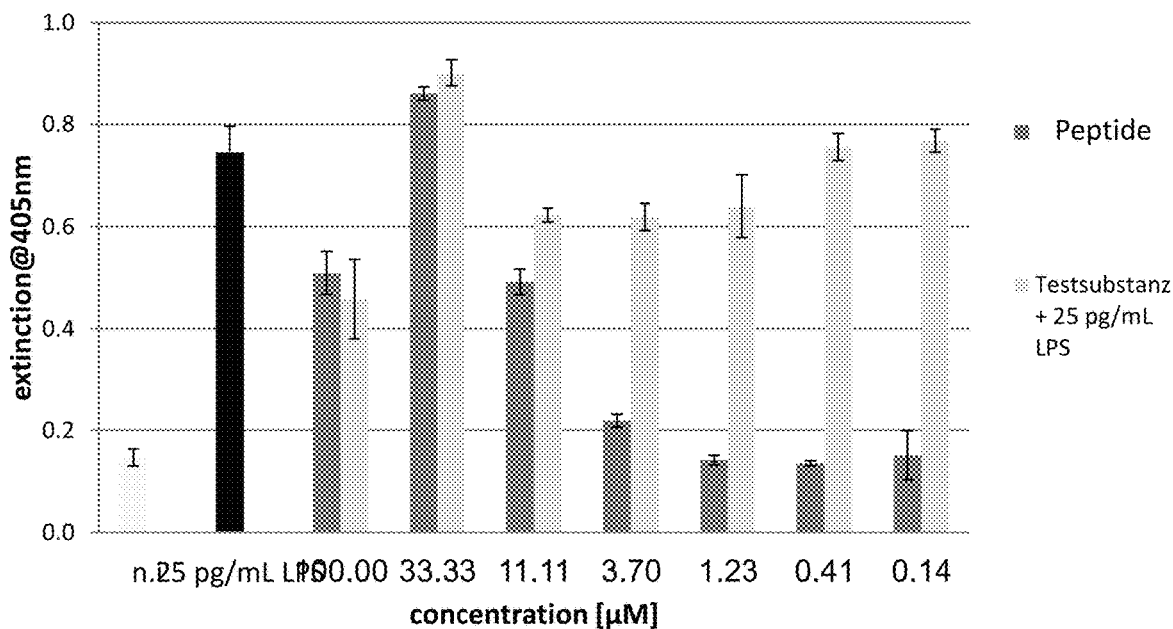
Figure 7V:
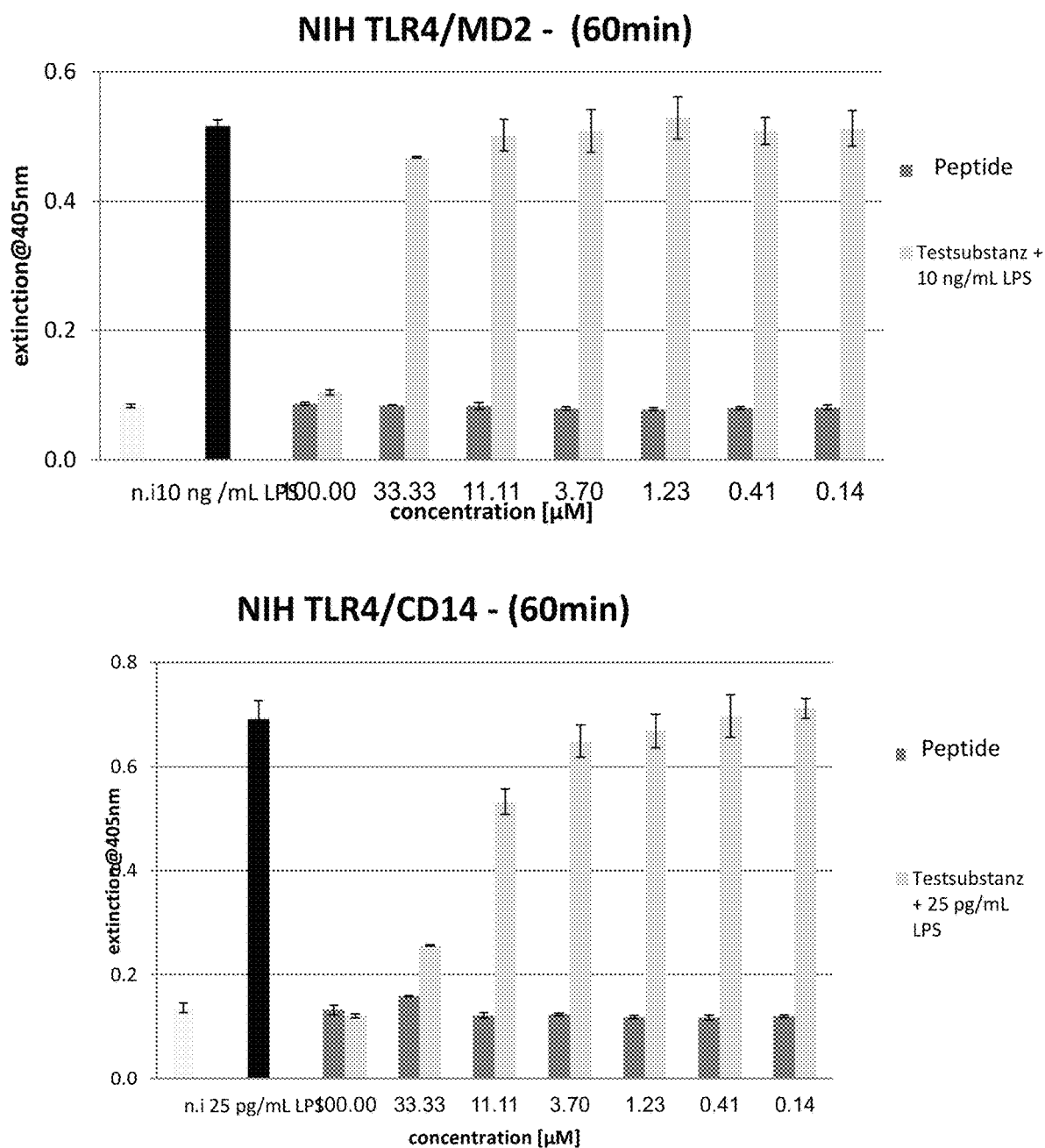
Figure 7W:
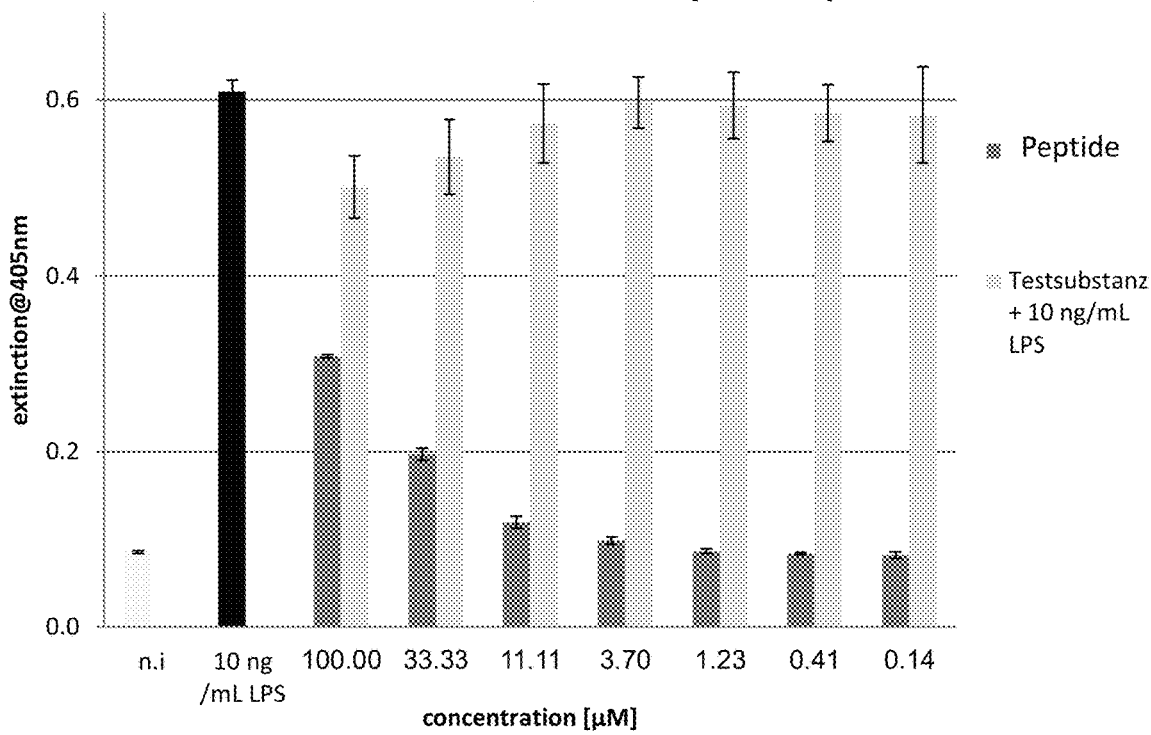
Figure 7W:
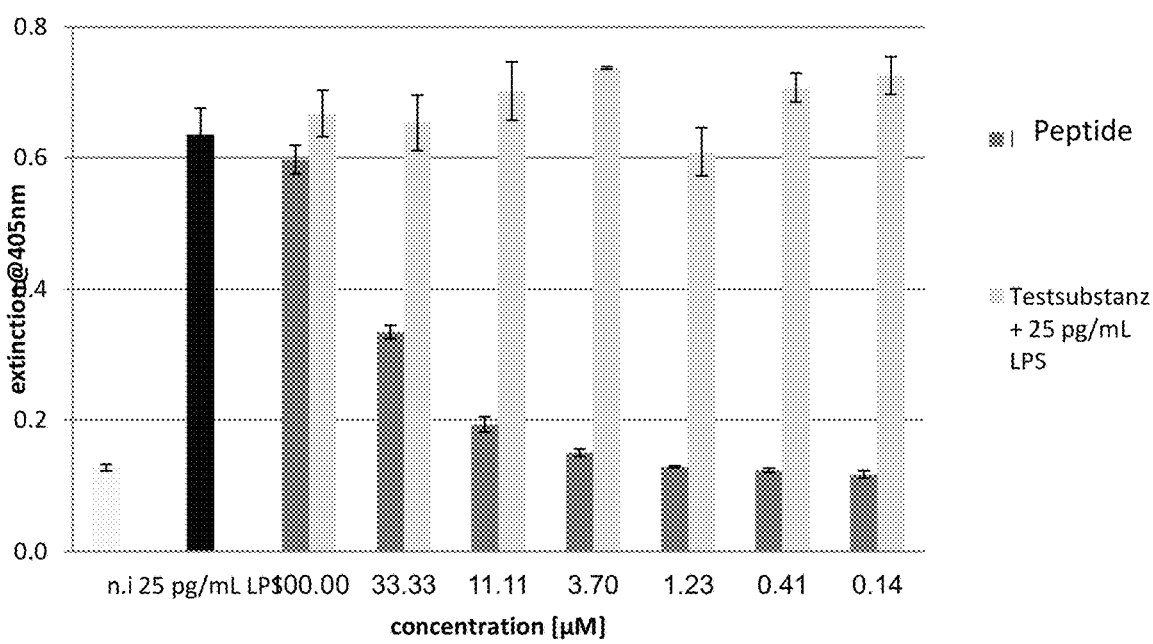
Figure 7X:
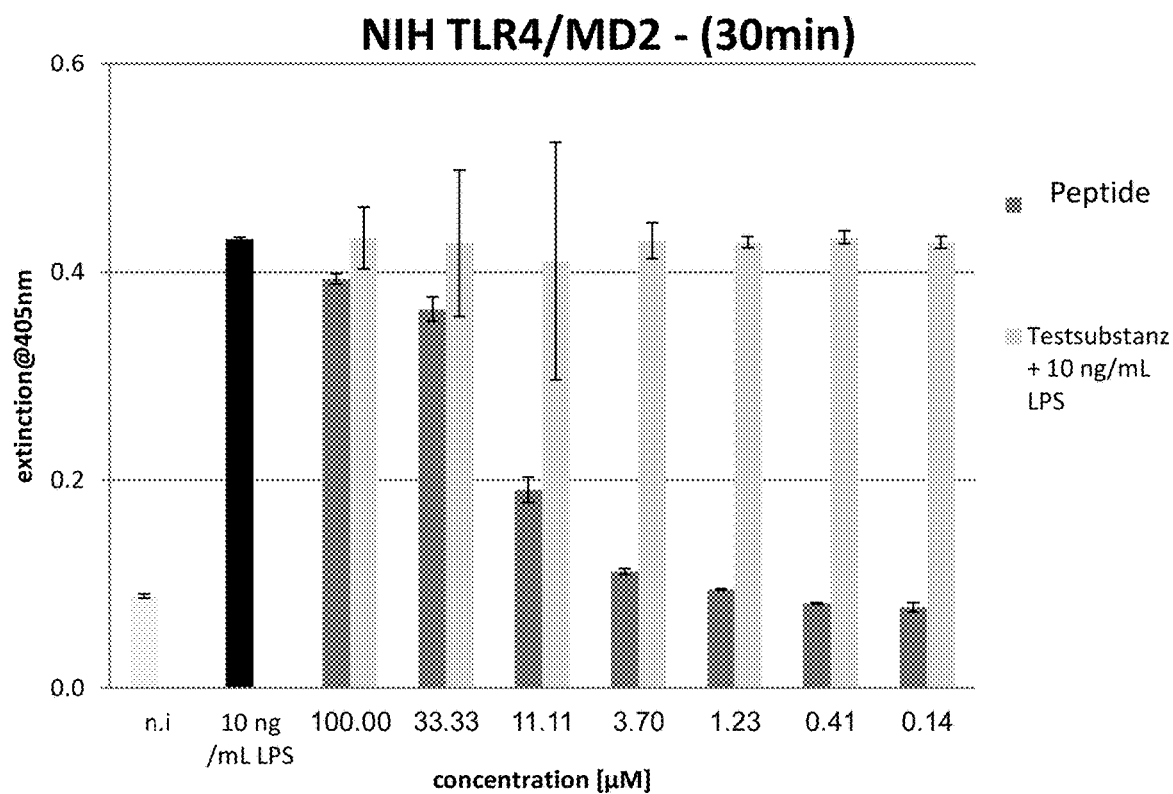
Figure 7X:
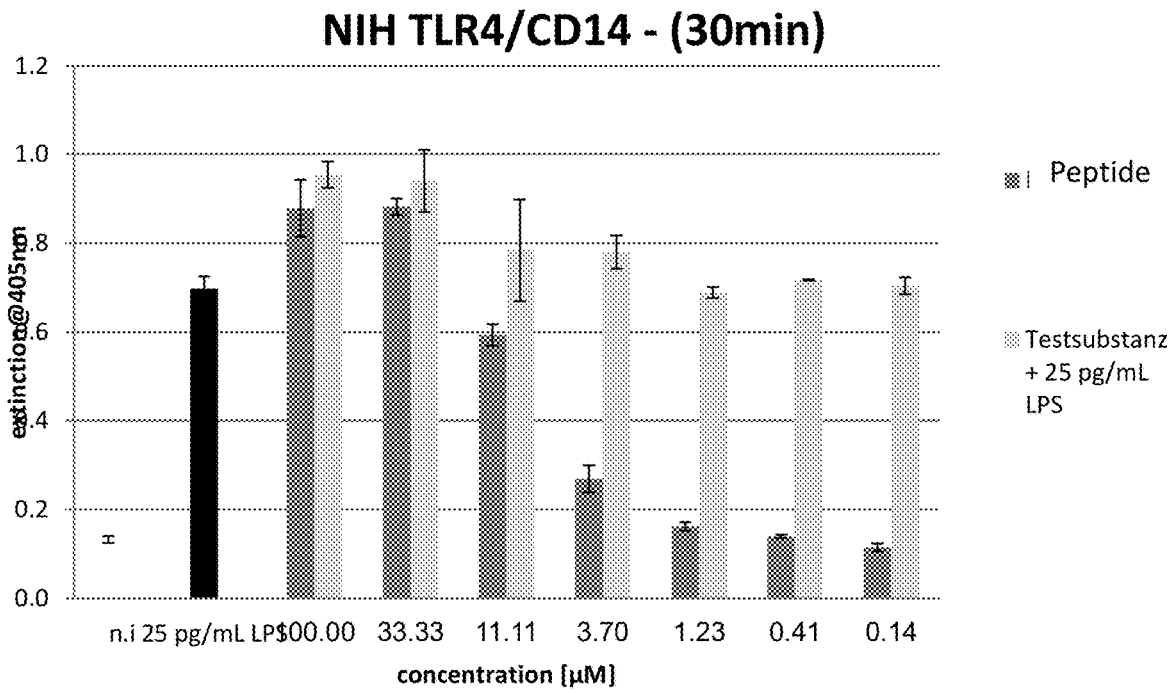
Figure 8:
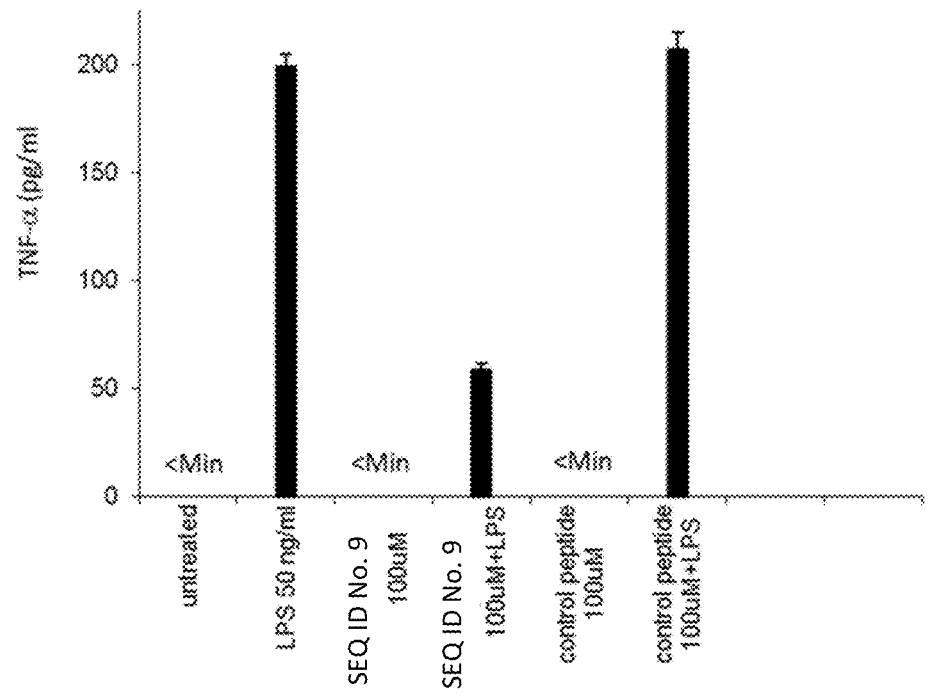
FIG. 8 presents an inhibitory effect of the peptide of SEQ ID No. 9 in the LPS-induced response, according to some embodiments of the invention.
Figure 8:
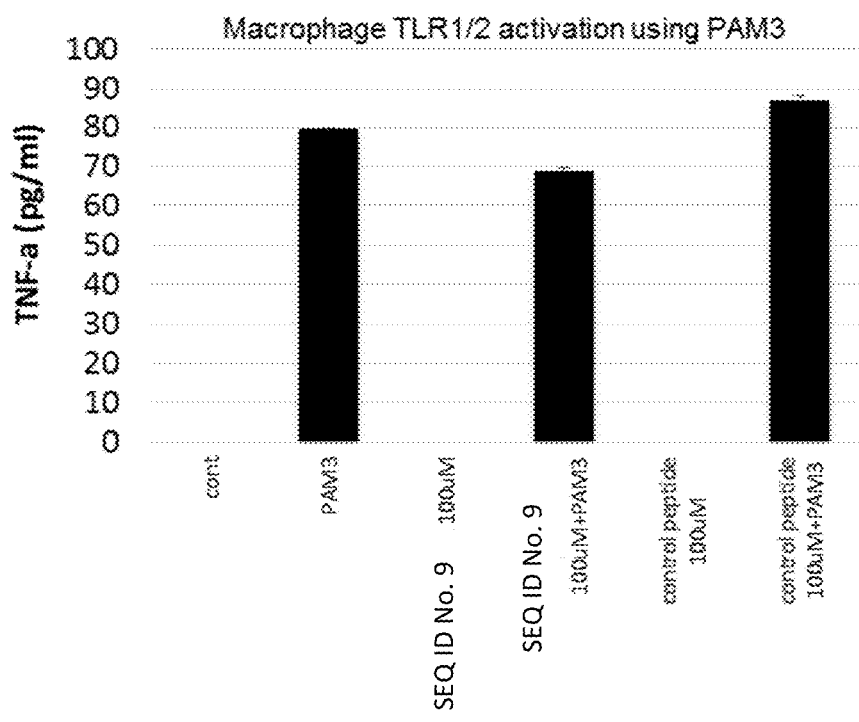

FIG. 8 presents an inhibitory effect of the peptide of SEQ ID No. 9 in the LPS-induced response, according to some embodiments of the invention. The top graph presents TNF-a release from primary mouse macrophages exposed to LPS treated with either peptide SEQ ID No. 9 or a control peptide while the bottom graph presents TNF-a release from primary mouse macrophages exposed to PAM3 treated with either peptide SEQ ID No. 9 or a control peptide. The inhibitory effect is observed in the LPS-induced response, with no significant effect on the PAM3 induced response. In FIG. 7K, peptide SEQ ID No. 9 shows inability of to inhibit an LPS mediated CD14-TLR4 activation of NIH3T3 cells (transfected with CD14, TLR4 and a reporter system to monitor TLR4 activation), a result which demonstrates the specificity of peptide SEQ ID No. 9 to inhibit MD2-TLR4 activation. In FIG. 8, primary mouse macrophages (expressing TLR4, MD2 and CD14) were treated with LPS and peptide SEQ ID No. 9, showing an inhibitory effect of macrophages activation, indicated by reduced tumor necrosis factor alpha (TNF-alpha) release to the extracellular medium triggered by LPS, in the presence of peptide SEQ ID No. 9. This method had been previously described (Lerner et al. 2011, Heparanase powers a chronic inflammatory circuit that promotes colitis-associated tumorigenesis in mice. J Clin Invest. 121(5): 1709-1721). FIG. 8 also shows the specificity of peptide SEQ ID No. 9 by not having any effect on TLR1/2 activation by PAM3 in mouse macrophages.

Additional testing was carried out to verify the activation levels if the peptides using expression level of activation markers. Raw cells were activated using the peptides of SEQ ID Nos. 1, 4 and 5 and a control peptide. The analysis of the activation level was done by examining the expression level of few activation markers. In order to verify the obtained results, two repeats were done. Standard Raw cells activation and FACS staining protocol were carried out.

The following describes the experimental design in detail. 5-7.5×10$^6$ Raw 264.7 cells were seeded in 6-well plates 24 h prior to the stimulation in 3 ml/well of DMEM containing 4 mmol/L glutamine and 10% heat-inactivated FCS. At the next day, cells were treated with bacterial LPS (10 or 100 ng/ml, *E. coli*, sigma) as positive control, and with peptides SEQ ID Nos. 1, 4, 5 and the control peptide (50, 100 and 200 μM for each peptide). Table 2 provides more details about the preparation of the peptides. The volume of the incubation was 1.5 ml for each well. After 24 or 48 h (two experiments), the concentrations of nitrite were measured in the culture supernatant by the Griess assay while absorbance was read at 550 nm. Simultaneously, the cells were stained for surface receptors: CD40, CD80, CD86 and MHC-II with the appropriate antibodies (biolegend) and analysed by flow cytometry using FSC express 3 software.

TABLE 2

Peptides preparation data.

| Peptide | Molecular weight | Dilution | | |
|---|---|---|---|---|
| | | DDW (ul) | DMSO (ul) | Total volume (ul) |
| SEQ ID No. 2 | 1657 | 80 | 40 | 120 |
| SEQ ID No. 11 | 1184 | 112 | 56 | 168 |
| SEQ ID No. 12 | 1181 | 113 | 56 | 169 |
| Control | 1535 | 87 | 44 | 131 |

Figure 9A:
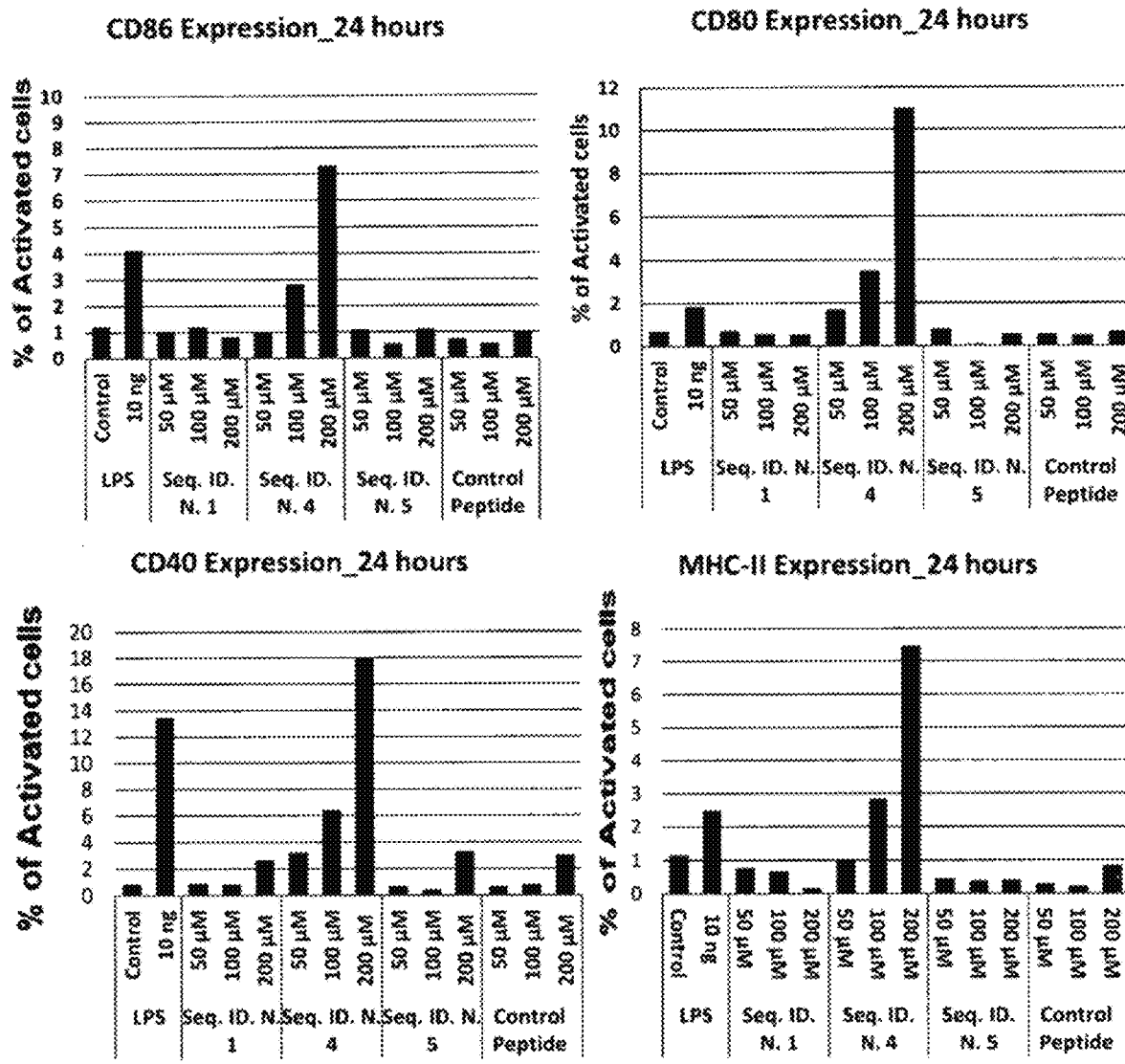
FIGS. 9A-9D present the percentages of expression of different activation markers (CD80, CD40, CD86, MHC-II) at the different setups (LPS, peptides SEQ ID Nos, 1, 4, 5 and the control peptide at different concentrations), according to some embodiments of the invention.
Figure 9B:
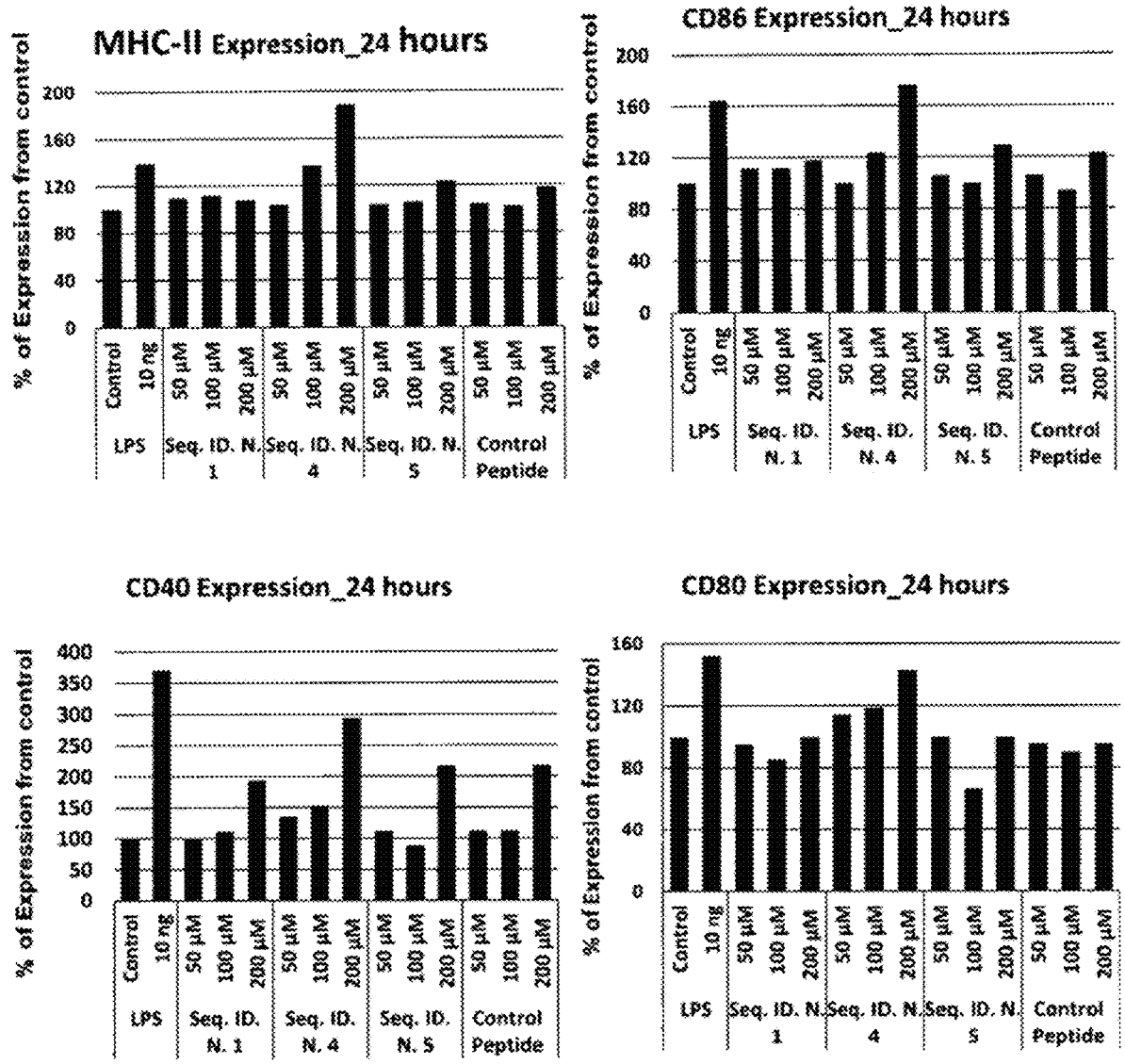
Figure 9C:
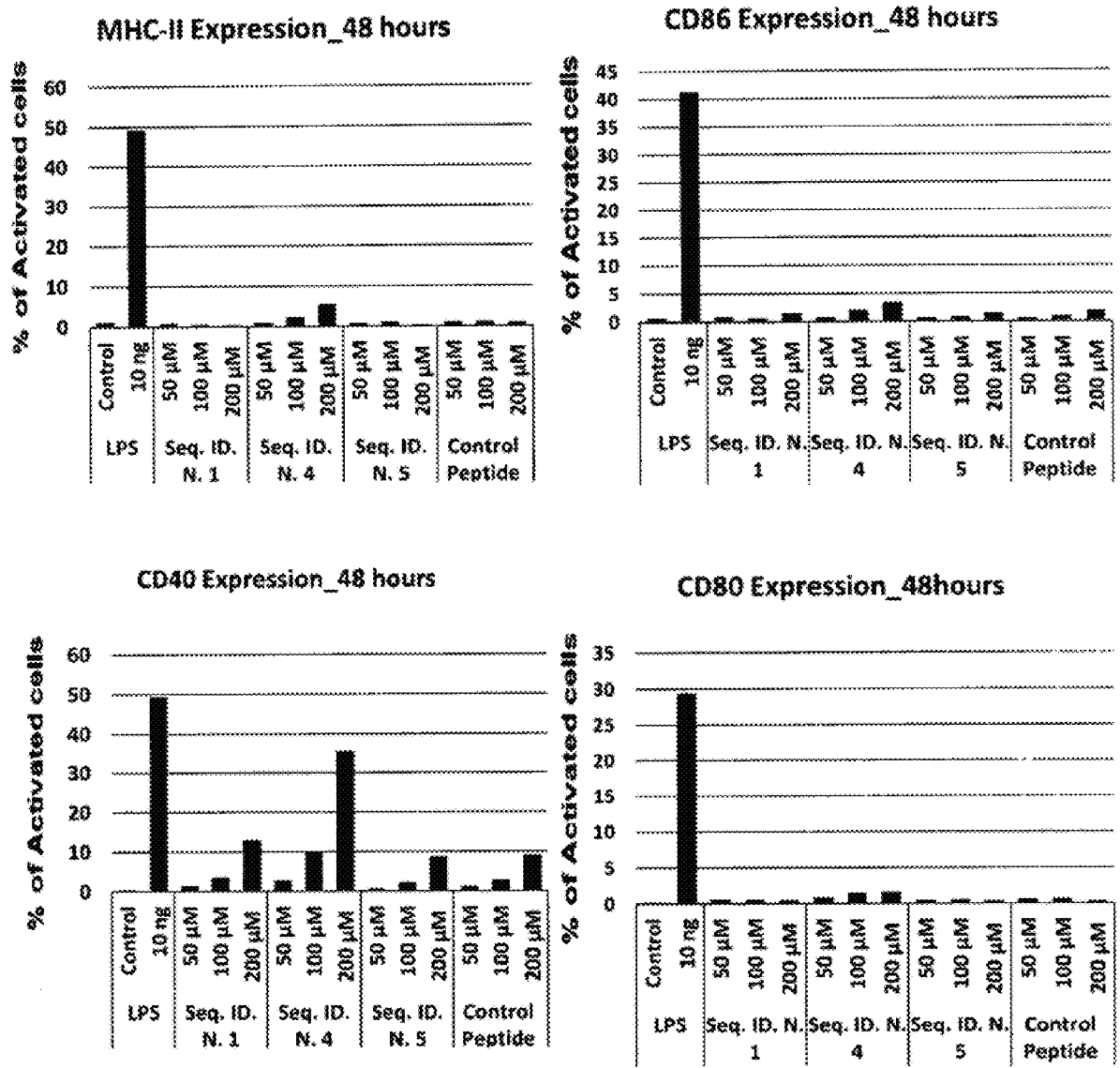
Figure 9D:
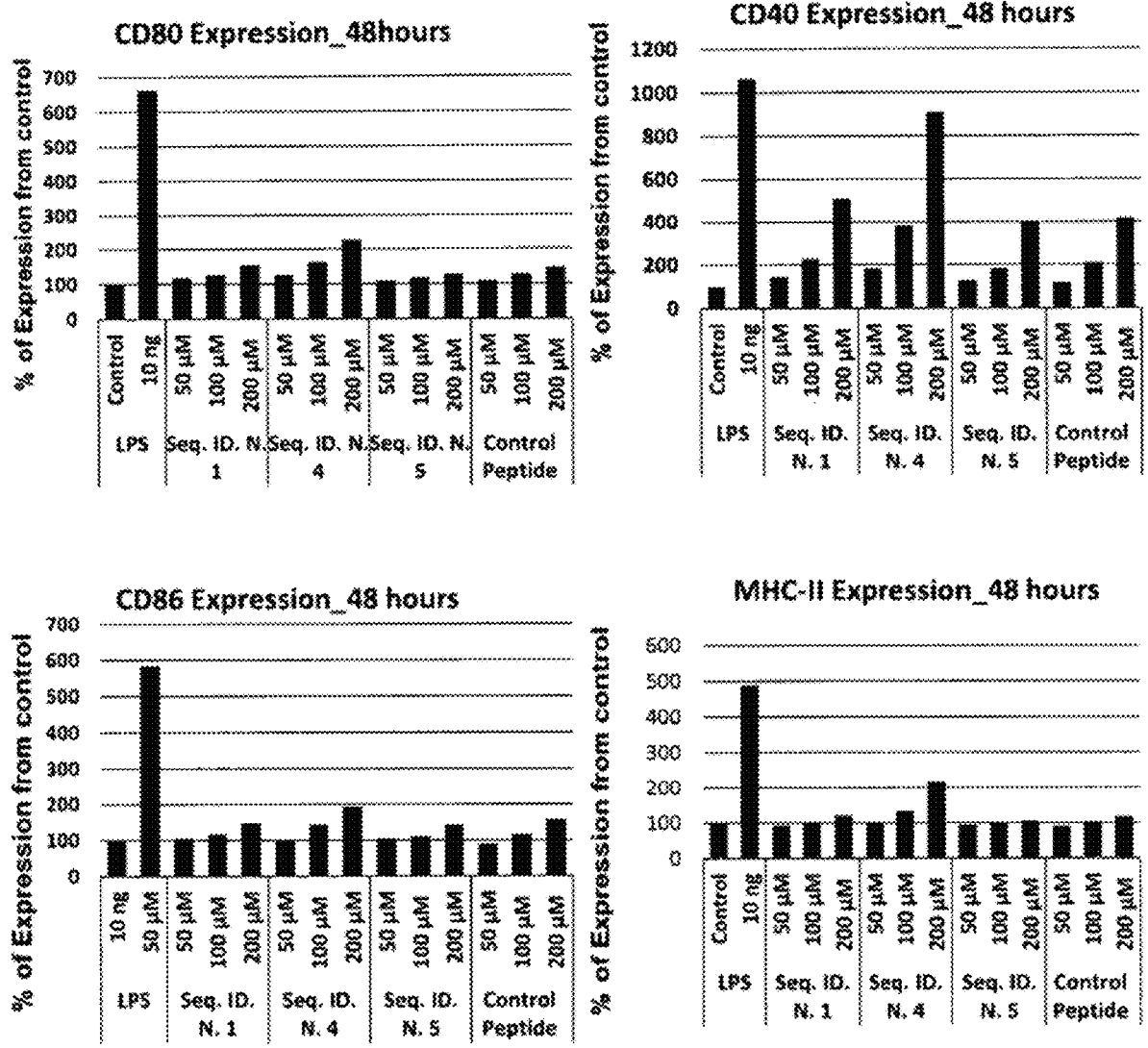

FIGS. 9A-9D present the percentages of expression of different activation markers (CD80, CD40, CD86, MHC-II) at the different setups (LPS, peptides SEQ ID Nos, 1, 4, 5 and the control peptide at different concentrations), according to some embodiments of the invention. FIGS. 9A and 9B relate to the 24 h experiment while FIGS. 9C and 9D relate to the 48 h experiment. According to data collected from both repetitions and as it emerges from the FACS analysis it appears that peptide SEQ ID No. 4 is the most promising stimulator for raw cells compared to the negative control and compared to the other peptides. Therefore, it is currently the most suitable candidate to serve as adjuvant and further research. Additional research is being carried out with respect to the other peptides, different concentrations, other effects, and activation measurements with peritoneal macrophages.

One attribute of TLR-4 activation is the release of the pro-inflammatory cytokine Interleukin-1β (IL1β). Several of our discovered peptides were tested for IL1β induction by ELISA following a 24-hour incubation with whole human blood. IL1β induction was measured with increasing dosage of the peptides alone, or with a fixed dosage of LPS (100 pg/ml). The results are shown in FIG. 10 and summarized in Table 3.

TABLE 3

IL1β induction in whole blood.

| | PAMP assay (NIH3T3 cells) | | IL-1β ELISA after blood activation | |
|---|---|---|---|---|
| Compound | Induction with compound alone | Induction with compound + LPS | Induction with compound alone | Induction with compound + LPS |
| SEQ ID. No. 6 | ++ | ++ | + | +++ |
| SEQ ID. No. 1 (M1) | + | + | ++ | +++ |
| SEQ ID. No. 1 (M2) | + | + | 0 | 0 |
| SEQ ID. No. 1 (M3) | + | + | 0 | 0 |
| SEQ ID. No. 4 (M1) | ++ | ++ | + | +++ |
| SEQ ID. No. 4 (M2) | ++ | ++ | + | +++ |
| SEQ ID. No. 4 | + | +++ | 0 | +++ |

0: no effect of the compound alone/no effect of the compound in addition to LPS alone.
+: small effect of the compound alone/small effect of the compound in addition to LPS alone.
++: intermediate effect of the comp. alone/intermediate effect of the comp. in add. to LPS alone.
+++: strong effect of the compound alone/strong effect of the compound in addition to LPS alone.

In certain embodiments, possible usage for peptides of SEQ ID Nos. 9-16 and 20 and/or their molecular derivatives are: (i) In the pharmaceutical industry, as drugs for immunomodulation of the innate immune system. These applications may be used in a wide variety of clinical settings, as well as for diagnostics and imaging applications. Non-limiting examples comprise protection from influenza mortality and treatment of sepsis; and (ii) In research, the peptides may be used e.g., as molecules blocking the MD2-TLR4 interaction, for inhibition of TLR4 activation, for labeling (fluorescent or other). Non-limiting examples are: labeling of MD2 for experimental use and in virto/in vivo use as specific inhibitor for basic research (in immunology, cancer, pharmacology and others).

In certain embodiments, possible usage for peptide of SEQ ID Nos. 1-8, 16, 17, 19, 21 and 22 and/or their molecular derivatives are: (i) In the pharmaceutical industry, both human and veterinary, as drugs for immunomodulation of the innate immune system. These applications may be used in a wide variety of clinical settings, as well as for diagnostics and imaging applications. Non-limiting examples comprise implementations as vaccine adjuvants, allowing accelerating antigen-specific immune responses; (ii) In research, peptides that activate both CD-14 TLR4 and MD2-TLR4 or one receptor/co-receptor pair but not the other, are important and useful for several research applications. Research applications may vary from activation of TLR4 to labeling (fluorescent or other). Non-limiting examples comprise labeling of MD2 for experimental use and in vitro or in vivo use as specific inhibitor for basic research (in immunology, cancer, pharmacology and others). Additionally, the availability of both co-receptor specific and non-specific activators can be cardinal in understanding the mechanisms of innate immune responses and autoimmune disease.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A peptide that binds Toll Like Receptor 4 (TLR4) with at least one of co-receptors myeloid differentiation factor 2 (MD2) and cluster of differentiation 14 (CD14), wherein the peptide is selected from: a peptide comprising the sequence of SEQ ID NO: 1; and a peptide consisting of a sequence selected from SEQ ID NOs: 6, 19, 21, and 22.

2. The peptide of claim 1, wherein the peptide is an activator of TLR4.

3. The peptide of claim 1, wherein said peptide consists of SEQ ID NO: 6 and binds TLR4 with co-receptor MD2.

4. The peptide of claim 1, wherein said peptide is selected from a peptide comprising SEQ ID NO: 1 and a peptide consisting of a sequence selected from SEQ ID NOs: 19, 21, and 22, wherein the peptide binds TLR4 with the co-receptor CD14.

5. The peptide of claim 1, wherein the peptide comprises the sequence set forth in SEQ ID NO: 1.

6. The peptide of claim 5, wherein the peptide further comprises an addition at the N-terminus or at the C-terminus of the sequence.

7. The peptide of claim 6, wherein the addition consists of at least one of: an amino acid, a peptide, a protein and an antigen.

8. A composition comprising a peptide of claim 1.

9. The composition of claim 8, wherein the composition is in the form of a vaccine adjuvant.

10. The peptide of claim 1 wherein the peptide is cyclic and selected from the group consisting of SEQ ID NOS: 6, 19, 21 and 22.

* * * * *

SEQUENCE LISTING

```
<160> NUMBER OF SEQ ID NOS: 30

<210> SEQ ID NO 1
<211> LENGTH: 15
<212> TYPE: PRT
<213> ORGANISM: Artificial Sequence
<220> FEATURE:
<223> OTHER INFORMATION: Activator
<220> FEATURE:
<221> NAME/KEY: MISC_FEATURE
<222> LOCATION: (15)..(15)
<223> OTHER INFORMATION: Xaa is an amino acid residue selected from Gly
      and Tyr
<220> FEATURE:
<221> NAME/KEY: MOD_RES
<222> LOCATION: (15)..(15)
<223> OTHER INFORMATION: The C-terminus is optionally modified

<400> SEQUENCE: 1

Arg Tyr Glu Thr Met Ser Ile Met Ile Lys Ser Gly Gly Lys Xaa
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: Activator

<400> SEQUENCE: 2

Glu Trp Gly Trp Arg Met Ile Ile
1               5

<210> SEQ ID NO 3
<211> LENGTH: 17
<212> TYPE: PRT
<213> ORGANISM: Artificial Sequence
<220> FEATURE:
<223> OTHER INFORMATION: Activator

<400> SEQUENCE: 3

Pro Leu Trp Met Met Ile Lys Ser Met Gly Ser Met Met Glu Met Lys
1               5                   10                  15

Lys

<210> SEQ ID NO 4
<211> LENGTH: 9
<212> TYPE: PRT
<213> ORGANISM: Artificial Sequence
<220> FEATURE:
<223> OTHER INFORMATION: Activator

<400> SEQUENCE: 4

Ile Leu Tyr Met Ser Leu Lys Trp Met
1               5

<210> SEQ ID NO 5
<211> LENGTH: 9
<212> TYPE: PRT
<213> ORGANISM: Artificial Sequence
<220> FEATURE:
<223> OTHER INFORMATION: Activator

<400> SEQUENCE: 5

Ile Leu Tyr Lys Ser Leu Lys Trp Met
1               5
```

```
<210> SEQ ID NO 6
<211> LENGTH: 6
<212> TYPE: PRT
<213> ORGANISM: Artificial Sequence
<220> FEATURE:
<223> OTHER INFORMATION: Activator, cyclic

<400> SEQUENCE: 6

Met Leu Ser Phe Arg Met
1               5

<210> SEQ ID NO 7
<211> LENGTH: 8
<212> TYPE: PRT
<213> ORGANISM: Artificial Sequence
<220> FEATURE:
<223> OTHER INFORMATION: Activator, cyclic

<400> SEQUENCE: 7

Trp Met Leu Gly Met Glu Ser Ile
1               5

<210> SEQ ID NO 8
<211> LENGTH: 10
<212> TYPE: PRT
<213> ORGANISM: Artificial Sequence
<220> FEATURE:
<223> OTHER INFORMATION: Activator, cyclic

<400> SEQUENCE: 8

Ile Gly Phe Met Met Met Lys Lys Glu Phe
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Inhibitor

<400> SEQUENCE: 9

Ile Leu Phe Met Gly Met Lys Trp Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Inhibitor

<400> SEQUENCE: 10

Met Ile Pro Tyr Gly Met Arg Met Met
1               5

<210> SEQ ID NO 11
<211> LENGTH: 11
<212> TYPE: PRT
<213> ORGANISM: Artificial Sequence
<220> FEATURE:
<223> OTHER INFORMATION: Inhibitor

<400> SEQUENCE: 11

Leu Ala Trp Tyr Phe Gly Arg Lys Ile Lys Glu
1               5                   10

<210> SEQ ID NO 12
```

```
<211> LENGTH: 7
<212> TYPE: PRT
<213> ORGANISM: Artificial Sequence
<220> FEATURE:
<223> OTHER INFORMATION: Inhibitor
<220> FEATURE:
<221> NAME/KEY: VARIANT
<222> LOCATION: (7)..(7)
<223> OTHER INFORMATION: CH3 replaces COOH

<400> SEQUENCE: 12

Lys Lys Leu Met Leu Ile Ile
1               5

<210> SEQ ID NO 13
<211> LENGTH: 6
<212> TYPE: PRT
<213> ORGANISM: Artificial Sequence
<220> FEATURE:
<223> OTHER INFORMATION: Inhibitor, cyclic

<400> SEQUENCE: 13

Ser Trp Glu Phe Leu Trp
1               5

<210> SEQ ID NO 14
<211> LENGTH: 7
<212> TYPE: PRT
<213> ORGANISM: Artificial Sequence
<220> FEATURE:
<223> OTHER INFORMATION: Inhibitor, cyclic

<400> SEQUENCE: 14

Ser Ile Trp Asp Thr Met Trp
1               5

<210> SEQ ID NO 15
<211> LENGTH: 6
<212> TYPE: PRT
<213> ORGANISM: Artificial Sequence
<220> FEATURE:
<223> OTHER INFORMATION: Inhibitor, cylic

<400> SEQUENCE: 15

Ile Trp Ser Arg Ser Trp
1               5

<210> SEQ ID NO 16
<211> LENGTH: 5
<212> TYPE: PRT
<213> ORGANISM: Artificial Sequence
<220> FEATURE:
<223> OTHER INFORMATION: Activator
<220> FEATURE:
<221> NAME/KEY: VARIANT
<222> LOCATION: (1)..(5)
<223> OTHER INFORMATION: All D-amino acids
<220> FEATURE:
<221> NAME/KEY: VARIANT
<222> LOCATION: (5)..(5)
<223> OTHER INFORMATION: CH3 group replaces C-terminus

<400> SEQUENCE: 16

Arg Met Met Met Trp
1               5

<210> SEQ ID NO 17
<211> LENGTH: 5
<212> TYPE: PRT
```

```
<213> ORGANISM: Artificial Sequence
<220> FEATURE:
<223> OTHER INFORMATION: Activator
<220> FEATURE:
<221> NAME/KEY: VARIANT
<222> LOCATION: (1)..(5)
<223> OTHER INFORMATION: All D-amino acids
<220> FEATURE:
<221> NAME/KEY: VARIANT
<222> LOCATION: (3)..(3)
<223> OTHER INFORMATION: both isoleucine chiral centers in D-enantiomer

<400> SEQUENCE: 17

Trp Trp Ile Lys Asp
1               5

<210> SEQ ID NO 18
<211> LENGTH: 10
<212> TYPE: PRT
<213> ORGANISM: Artificial Sequence
<220> FEATURE:
<223> OTHER INFORMATION: Activator
<220> FEATURE:
<221> NAME/KEY: VARIANT
<222> LOCATION: (1)..(10)
<223> OTHER INFORMATION: All D-amino acids
<220> FEATURE:
<221> NAME/KEY: VARIANT
<222> LOCATION: (2)..(2)
<223> OTHER INFORMATION: Both isoleucine chiral centers in D-enantiomer

<400> SEQUENCE: 18

Thr Ile Tyr Met Met Met Thr Met Lys Gly
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Activator, cyclic
<220> FEATURE:
<221> NAME/KEY: VARIANT
<222> LOCATION: (1)..(7)
<223> OTHER INFORMATION: All D-amino acids

<400> SEQUENCE: 19

Gly Trp Leu Trp Arg Ser Leu
1               5

<210> SEQ ID NO 20
<211> LENGTH: 7
<212> TYPE: PRT
<213> ORGANISM: Artificial Sequence
<220> FEATURE:
<223> OTHER INFORMATION: Inhibitor, cyclic
<220> FEATURE:
<221> NAME/KEY: VARIANT
<222> LOCATION: (1)..(7)
<223> OTHER INFORMATION: All D-amino acids

<400> SEQUENCE: 20

Gly Trp Trp Trp Arg Ala Leu
1               5

<210> SEQ ID NO 21
<211> LENGTH: 8
<212> TYPE: PRT
<213> ORGANISM: Artificial Sequence
<220> FEATURE:
<223> OTHER INFORMATION: Activator, cyclic
```

```
<220> FEATURE:
<221> NAME/KEY: VARIANT
<222> LOCATION: (1)..(8)
<223> OTHER INFORMATION: All D-amino acids

<400> SEQUENCE: 21

Gly Glu Leu Asp Lys Phe Thr Met
1               5

<210> SEQ ID NO 22
<211> LENGTH: 10
<212> TYPE: PRT
<213> ORGANISM: Artificial Sequence
<220> FEATURE:
<223> OTHER INFORMATION: Activator, cyclic
<220> FEATURE:
<221> NAME/KEY: VARIANT
<222> LOCATION: (1)..(10)
<223> OTHER INFORMATION: All D-amino acids

<400> SEQUENCE: 22

Gly Phe Trp Ser Glu Glu Glu Lys Ser Leu
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Activator or Inhibitor
<220> FEATURE:
<221> NAME/KEY: MISC_FEATURE
<222> LOCATION: (1)..(9)
<223> OTHER INFORMATION: Xaa can be any naturally occuring amino acidd

<400> SEQUENCE: 23

Xaa Xaa Xaa Xaa Xaa Xaa Xaa Xaa Xaa
1               5

<210> SEQ ID NO 24
<211> LENGTH: 6
<212> TYPE: PRT
<213> ORGANISM: Artificial Sequence
<220> FEATURE:
<223> OTHER INFORMATION: Activator, cyclic
<220> FEATURE:
<221> NAME/KEY: MISC_FEATURE
<222> LOCATION: (1)..(6)
<223> OTHER INFORMATION: Xaa can be any naturally occuring amino acid

<400> SEQUENCE: 24

Xaa Xaa Xaa Xaa Xaa Xaa
1               5

<210> SEQ ID NO 25
<211> LENGTH: 6
<212> TYPE: PRT
<213> ORGANISM: Artificial Sequence
<220> FEATURE:
<223> OTHER INFORMATION: Activator, cyclic
<220> FEATURE:
<221> NAME/KEY: MISC_FEATURE
<222> LOCATION: (1)..(6)
<223> OTHER INFORMATION: Xaa can be any naturally occuring amino acid

<400> SEQUENCE: 25

Xaa Xaa Xaa Xaa Xaa Xaa
1               5
```

```
<210> SEQ ID NO 26
<211> LENGTH: 10
<212> TYPE: PRT
<213> ORGANISM: Artificial Sequence
<220> FEATURE:
<223> OTHER INFORMATION: Activator, cyclic
<220> FEATURE:
<221> NAME/KEY: MISC_FEATURE
<222> LOCATION: (1)..(10)
<223> OTHER INFORMATION: Xaa can be any naturally occuring amino acid

<400> SEQUENCE: 26

Xaa Xaa Xaa Xaa Xaa Xaa Xaa Xaa Xaa Xaa
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Activator, cyclic
<220> FEATURE:
<221> NAME/KEY: MISC_FEATURE
<222> LOCATION: (1)..(10)
<223> OTHER INFORMATION: Xaa can be any naturally occuring amino acid

<400> SEQUENCE: 27

Xaa Xaa Xaa Xaa Xaa Xaa Xaa Xaa Xaa Xaa
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Inhibitor
<220> FEATURE:
<221> NAME/KEY: MISC_FEATURE
<222> LOCATION: (1)..(7)
<223> OTHER INFORMATION: Xaa can be any naturally occuring amino acid

<400> SEQUENCE: 28

Xaa Xaa Xaa Xaa Xaa Xaa Xaa
1               5

<210> SEQ ID NO 29
<211> LENGTH: 7
<212> TYPE: PRT
<213> ORGANISM: Artificial Sequence
<220> FEATURE:
<223> OTHER INFORMATION: Activator or inhibitor, cyclic
<220> FEATURE:
<221> NAME/KEY: MISC_FEATURE
<222> LOCATION: (1)..(7)
<223> OTHER INFORMATION: Xaa can be any naturally occuring amino acid

<400> SEQUENCE: 29

Xaa Xaa Xaa Xaa Xaa Xaa Xaa
1               5

<210> SEQ ID NO 30
<211> LENGTH: 10
<212> TYPE: PRT
<213> ORGANISM: Artificial Sequence
<220> FEATURE:
<223> OTHER INFORMATION: Activator, cyclic
<220> FEATURE:
<221> NAME/KEY: MISC_FEATURE
<222> LOCATION: (1)..(10)
<223> OTHER INFORMATION: Xaa can be any naturally occuring amino acid
```

```
<400> SEQUENCE: 30

Xaa Xaa Xaa Xaa Xaa Xaa Xaa Xaa Xaa Xaa
1               5                   10
```